US009145363B2

(12) United States Patent
Yabunouchi et al.

(10) Patent No.: US 9,145,363 B2
(45) Date of Patent: Sep. 29, 2015

(54) AROMATIC AMINE DERIVATIVE AND ORGANIC ELECTROLUMINESCENT ELEMENT

(75) Inventors: Nobuhiro Yabunouchi, Chiba (JP); Tomoki Kato, Chiba (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 442 days.

(21) Appl. No.: 13/201,785

(22) PCT Filed: Feb. 16, 2010

(86) PCT No.: PCT/JP2010/052292
§ 371 (c)(1),
(2), (4) Date: Aug. 16, 2011

(87) PCT Pub. No.: WO2010/095621
PCT Pub. Date: Aug. 26, 2010

(65) Prior Publication Data
US 2011/0297924 A1 Dec. 8, 2011

(30) Foreign Application Priority Data
Feb. 18, 2009 (JP) .................. 2009-035387

(51) Int. Cl.
| H01L 51/50 | (2006.01) |
| C07D 209/86 | (2006.01) |
| C07D 405/04 | (2006.01) |
| C07D 405/10 | (2006.01) |
| C07D 405/14 | (2006.01) |
| C07D 409/04 | (2006.01) |
| C07D 409/10 | (2006.01) |
| C07D 409/14 | (2006.01) |
| H01L 51/00 | (2006.01) |

(52) U.S. Cl.
CPC ............ *C07D 209/86* (2013.01); *C07D 405/04* (2013.01); *C07D 405/10* (2013.01); *C07D 405/14* (2013.01); *C07D 409/04* (2013.01); *C07D 409/10* (2013.01); *C07D 409/14* (2013.01); *H01L 51/006* (2013.01); *H01L 51/0061* (2013.01); *H01L 51/0081* (2013.01); *H01L 51/5048* (2013.01); *H01L 51/5088* (2013.01)

(58) Field of Classification Search
USPC .................. 428/690, 917; 313/504, 505, 506; 257/40, E51.05, E51.026, E51.032; 548/304.1, 418, 440; 564/26, 426, 434
See application file for complete search history.

(56) References Cited

U.S. PATENT DOCUMENTS

| 2004/0062950 A1* | 4/2004 | Iwanaga ........................ 428/690 |
| 2004/0113547 A1* | 6/2004 | Son et al. ...................... 313/504 |
| 2004/0265630 A1* | 12/2004 | Suh et al. ..................... 428/690 |
| 2005/0142379 A1* | 6/2005 | Juni et al. ..................... 428/690 |
| 2007/0018569 A1* | 1/2007 | Kawamura et al. ........... 313/504 |
| 2009/0017330 A1* | 1/2009 | Iwakuma et al. ............. 428/690 |

FOREIGN PATENT DOCUMENTS

| EP | 2 301 921 A1 | 3/2011 | |
| JP | 11-167990 | 6/1999 | |
| JP | 2005-112765 | 4/2005 | |
| JP | 2006-56841 | 3/2006 | |
| JP | 2007-171808 | 7/2007 | |
| JP | 2008-78362 | 4/2008 | |
| JP | 2008-294161 | * 12/2008 | .............. H01L 51/50 |
| WO | WO 2006/025290 A1 | 3/2006 | |
| WO | WO 2008/072596 A1 | 6/2008 | |
| WO | WO 2009/008099 A1 | 1/2009 | |
| WO | WO 2009/008100 A1 | 1/2009 | |
| WO | WO 2009/061156 A1 | 5/2009 | |
| WO | WO 2010/021524 A2 | 2/2010 | |

OTHER PUBLICATIONS

U.S. Appl. No. 13/435,965, filed Mar. 30, 2012, Kato.
U.S. Appl. No. 13/399,412, filed Feb. 17, 2012, Kato.
U.S. Appl. No. 13/509,681, filed May 14, 2012, Kato.
International Search Report issued Apr. 20, 2010, in Patent Application No. PCT/JP2010/052292.
Zhong Hui Li, et al., "Synthesis and Functional Properties of End-Dendronized Oligo(9,9-diphenyl)fluorenes", Organic Letters, 2006, vol. 8, No. 7, pp. 1499-1502.
Sebastian Scholz, et al., "Analysis of Complete Organic Semiconductor Devices by Laser Desorption/Ionization Time-of-Flight Mass Spectrometry", Advanced Functional Materials, 2008, vol. 18, No. 17, pp. 2541-2547.
Mo Jun Xiong, et al., "End-Capped Terfluorene Derivatives: Synthesis and Structure-Functional Property Relationships", Australian Journal of Chemistry, 2007, vol. 60, No. 8, pp. 608-614.
Jianping Lu, et al., "Synthesis and Properties of Multi-Triarylamine-Substituted Carbazole-Based Dendrimers with an Oligothiophene Core for Potential Applications in Organic Solar Cells and Light-Emitting Diodes", Chemistry of Materials, 2006, vol. 18, No. 26, pp. 6194-6203.

(Continued)

Primary Examiner — Gregory Clark
(74) Attorney, Agent, or Firm — Oblon, McClelland, Maier & Neustadt, L.L.P.

(57) ABSTRACT

Provided are a long-lifetime organic electroluminescence device which can be fabricated in an improved yield owing to suppressed crystallization of molecules, and an aromatic amine derivative that realizes the device, i.e., a novel aromatic amine derivative having a specific structure. Specifically provided are an organic electroluminescence device, including an organic thin film layer formed of one or more layers including at least a light emitting layer, the organic thin film layer being interposed between a cathode and an anode, and an aromatic amine derivative for at least one layer of the organic thin film layer, in particular, a hole transporting layer, the derivative having at least one such structure that a substituent in which two or more specific heterocycles are linked to each other, in particular, a substituent in which two or more specific heterocycles are linked through an aryl group is bonded to an amine through an aryl group.

23 Claims, No Drawings

(56) References Cited

OTHER PUBLICATIONS

Ping Fang Xia, et al., "Synthesis and Properties of Monodisperse Multi-Triarylamine-Substituted Oligothiophenes and 4,7-Bis(2'-oligothienyl)-2,1,3-benzothiadiazoles for Organic Solar Cell Applications", Journal of Polymer Science, Part A: Polymer Chemistry, 2009, vol. 47, No. 1, pp. 137-148.

Ying Lin, et al., "Conjugated Copolymers Comprised Cyanophenyl-Substituted Spirobifluorene and Tricarbazole-Triphenylamine Repeat Units for Blue-Light-Emitting Diodes", Journal of Polymer Science, Part A: Polymer Chemistry, vol. 48, No. 2, pp. 292-301.

U.S. Appl. No. 13/979,075, filed Jul. 17, 2013, Kato.

Extended European Search Report issued Jul. 27, 2012 in Patent Application No. 10743747.7.

\* cited by examiner ical amine derivative having a
AROMATIC AMINE DERIVATIVE AND ORGANIC ELECTROLUMINESCENT ELEMENT This application is a 371 of PCT/JP10/52292 filed Feb. 16, 2010. Priority to Japanese patent application 2009-035387, filed Feb. 18, 2009, is claimed.

TECHNICAL FIELD

The present invention relates to an aromatic amine derivative and an organic electroluminescence (hereinafter, abbreviated as organic EL) device using the same, and more particularly, to an aromatic amine derivative capable of increasing a lifetime of the organic EL device even at high temperatures by using an aromatic amine derivative having a specific structure as a hole transporting material.

BACKGROUND ART

An organic EL device is a spontaneous light emitting device which utilizes such a principle that a fluorescent substance emits light by virtue of recombination energy of holes injected from an anode and electrons injected from a cathode by an application of an electric field. Since an organic EL device of the laminate type capable of being driven under low electric voltage has been reported by C. W. Tang et al. of Eastman Kodak Company (C. W. Tang and S. A. Vanslyke, Applied Physics Letters, Volume 51, Page 913, 1987, or the like), many studies have been conducted for an organic EL device using an organic material as a constituent material. Tang et al. used tris(8-quinolinolato)aluminum for a light emitting layer and a triphenyldiamine derivative for a hole transporting layer. Advantages of the laminate structure include the followings: an efficiency of the hole injection into the light emitting layer can be increased; an efficiency of forming excitons which are formed by blocking and recombining electrons injected from the cathode can be increased; and excitons formed within the light emitting layer can be enclosed. As described above, for the device structure of the organic EL device, a two-layered structure having a hole transporting (injecting) layer and an electron transporting light emitting layer and a three-layered structure having a hole transporting (injecting) layer, a light emitting layer, an electron transporting (injecting) layer, and the like are widely known. In order to increase the efficiency of recombination of injected holes and electrons in such devices of the laminate type, the device structure and the process of forming the device have been studied.

In general, when an organic EL device is driven or stored in an environment of high temperature, there occur adverse affects such as a change in luminescent color, a decrease in emission efficiency, an increase in driving voltage, and a decrease in a lifetime of light emission. In order to prevent the adverse affects, it has been necessary that the glass transition temperature (Tg) of the hole transporting material be elevated. Therefore, it is necessary that many aromatic groups be held within a molecule of the hole transporting material (for example, an aromatic diamine derivative of Patent Literature 1 and an aromatic fused ring diamine derivative of Patent Literature 2), and in general, a structure having 8 to 12 benzene rings is preferably used.

However, in the case of a highly symmetrical compound and a compound high in flatness each having a large number of aromatic groups in a molecule, crystallization is liable to occur upon fabrication of the organic EL device through the formation of a thin film by using those hole transporting materials. As a result, there arises a problem such as clogging of an outlet of a crucible to be used in vapor deposition or a reduction in yields of the organic EL device due to generation of defects of the thin film resulting from the crystallization. In addition, a compound having a large number of aromatic groups in any one of its molecules generally has a high glass transition temperature (Tg), but has a high sublimation temperature. Accordingly, there arises a problem in that the lifetime of the compound is short probably because a phenomenon such as decomposition at the time of the vapor deposition or the formation of a nonuniform deposition film occurs.

Meanwhile, Patent Literature 3 reports such an amine compound that heterocycles linked to each other are bonded to an amine, but the compound does not show sufficient performance when used in an organic EL device.

In addition, Patent Literatures 4 and 5 each report such an amine compound that heterocycles directly linked to each other are bonded to an amine through an aryl group, but the compound does not show sufficient performance when used in an organic EL device. In addition, Patent Literature 5 merely gives examples of such compound, and describes neither an example in which the synthesis of the compound is performed nor an example in which the compound is used in an organic EL device. In addition, Patent Literature 6 reports such a diamine compound that two amines are each bonded through an aryl group to a substituent to which a heterocycle is directly linked, but the compound does not show sufficient performance when used in an organic EL device. In addition, Patent Literature 7 reports such a diamine compound that two amines are directly bonded to a substituent to which two heterocycles are each linked through an aryl group, but the compound does not show sufficient performance when used in an organic EL device. Patent Literature 8 reports such an amine compound that heterocycles linked to each other through an aryl group are bonded to an amine through an aryl group, but the amine compound does not show sufficient performance when used in an organic EL device.

As described above, high-efficiency, long-lifetime organic EL devices have been reported, but none of them provides sufficient performance, and hence the development of an organic EL device having additionally excellent performance has been strongly desired.

CITATION LIST

Patent Literature

[PTL 1] U.S. Pat. No. 4,720,432 A
[PTL 2] U.S. Pat. No. 5,061,569 A
[PTL 3] JP 2008-127290 A
[PTL 4] JP 2003-267972 A
[PTL 5] WO 2008/062636 A1
[PTL 6] JP 2003-133075 A
[PTL 7] WO 2008/072596 A1
[PTL 8] JP 11-167990 A

SUMMARY OF INVENTION

Technical Problem

The present invention has been made to solve the problems, and an object of the present invention is to provide an organic electroluminescence device having a long lifetime even at high temperatures, and an aromatic amine derivative that realizes the device.

Solution to Problem

The inventors of the present invention have made extensive studies to achieve the object. As a result, the inventors have found that the use of a novel aromatic amine derivative having a specific substituent as a material for an organic EL device, in particular, as a hole injecting material or a hole transporting material can solve the problems.

In addition, an interaction between molecules of an amine compound having, as a substituent, an aryl group having such a unit that two or more heterocycles are linked to each other is small because the compound has steric hindrance property. As a result, the crystallization of the molecules is suppressed, and hence the yield in which an organic EL device is fabricated can be increased. In addition, the following fact has been found. In particular, an amine compound having, as a substituent, an aryl group having such a unit that two or more heterocycles are linked to each other through an aryl group has a large energy gap (Eg), and hence can effectively block electrons from a light emitting layer. As a result, the injection of the electrons into a hole transporting layer is suppressed, and hence a lifetime-lengthening effect is exerted. In particular, a significant lifetime-lengthening effect is obtained by combining the compound with a blue light emitting device. The inventors of the present invention have completed the present invention on the basis of those findings.

That is, the present invention provides:

(1) an aromatic amine derivative, including a substituent represented by the following general formula (1):

[Chem. 1]

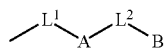

(1)

where:

(i) $L^1$ represents a substituted or unsubstituted arylene group having 6 to 50 ring carbon atoms;

(ii) $L^2$ represents a single bond, or a substituted or unsubstituted arylene group having 6 to 50 ring carbon atoms, provided that an arbitrary substituent for each of $L^1$ and $L^2$ includes a linear or branched alkyl group having 1 to 10 carbon atoms, a cycloalkyl group having 3 to 10 ring carbon atoms, a trialkylsilyl group having 3 to 30 carbon atoms, a triarylsilyl group whose aryl groups each have 6 to 10 ring carbon atoms, an alkylarylsilyl group having 8 to 24 carbon atoms whose aryl portion has 6 to 14 ring carbon atoms, a substituted or unsubstituted aryl group having 6 to 30 ring carbon atoms, a halogen atom, or a cyano group, and a plurality of substituents may be identical to or different from each other;

(iii) A represents a linking group represented by any one of the following general formulae (2) to (5):

[Chem. 2]

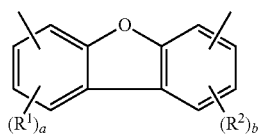

(2)

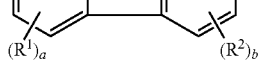

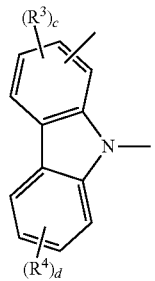

(3)

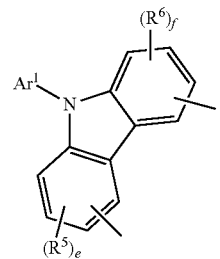

(4)

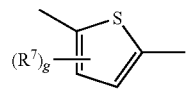

(5)

where:
$R^1$ to $R^7$ each independently represent the same substituent as the arbitrary substituent for each of the $L^1$ and the $L^2$, or a general formula -$L^2$-B where $L^2$ has the same meaning as that described above, and B has the same meaning as meaning of B to be described below; and
a plurality of $R^1$'s, $R^2$'s, $R^3$'s, $R^4$'s, $R^5$'s, $R^6$'s or $R^7$'s adjacent to each other may be bonded to each other to form a saturated or unsaturated ring, d represents an integer of 0 to 4, a, b, c, e, and f each independently represent an integer of 0 to 3, g represents an integer of 0 to 2, and $Ar^1$ represents a substituted or unsubstituted aryl group having 6 to 14 ring carbon atoms,
provided that substituents for $Ar^1$ each independently include the same substituent as the arbitrary substituent for each of the $L^1$ and the $L^2$; and (iv) B represents a substituent represented by any one of the following general formulae (6) to (9):

[Chem. 3]

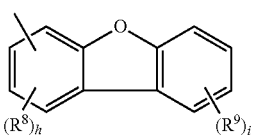

(6)

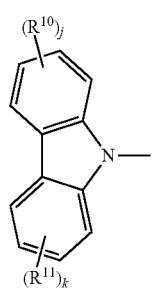

(7)

-continued (8)

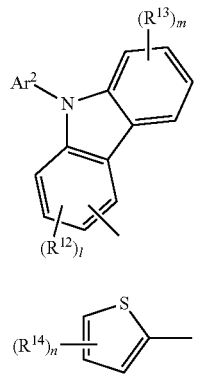

(9)

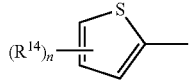

where:

$R^8$ to $R^{14}$ each independently represent the same substituent as the arbitrary substituent for each of the $L^1$ and the $L^2$, or a general formula -$L^2$-B where $L^2$ and B each have the same meaning as that described above; and a plurality of $R^8$'s, $R^9$'s, $R^{10}$'s, $R^{11}$'s, $R^{12}$'s, $R^{13}$'s, or $R^{14}$'s adjacent to each other may be bonded to each other to form a saturated or unsaturated ring, i, j, k, and m each independently represent an integer of 0 to 4, h, l, and n each independently represent an integer of 0 to 3, and $Ar^2$ represents a substituted or unsubstituted aryl group having 6 to 14 ring carbon atoms, provided that substituents for $Ar^2$ each independently include any one of the same substituent as the arbitrary substituent for each of the $L^1$ and the $L^2$ except an aryl group, and a phenyl group, a biphenyl group, a naphthyl group, and a phenanthryl group, and when the A represents a linking group represented by the general formula (5), B represents a substituent represented by the general formula (6);

(2) the aromatic amine derivative according to the above-mentioned item (1), in which the A represents a linking group represented by any one of the general formulae (2) to (4), and the B represents a substituent represented by any one of the general formulae (6) to (8);

(3) the aromatic amine derivative according to the above-mentioned item (1), in which:

the $L^1$ represents a linking group represented by any one of the following general formulae (10) to (12):

[Chem. 4]

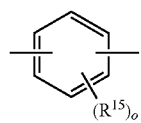
(10)

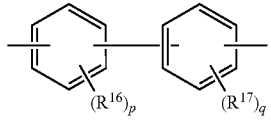
(11)

-continued (12)

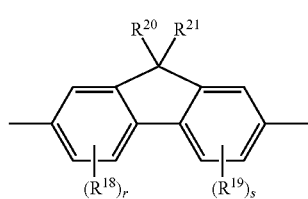

where:

$R^{15}$ to $R^{19}$ each independently represent the same substituent as the arbitrary substituent for each of the $L^1$ and the $L^2$, $R^{20}$ and $R^{21}$ each independently represent a linear or branched alkyl group formed of a hydrocarbon having 1 to 10 carbon atoms, or a cycloalkyl group having 3 to 10 ring carbon atoms, and a plurality of $R^{15}$'s, $R^{16}$'s, $R^{17}$'s, $R^{18}$'s, or $R^{19}$'s adjacent to each other may be bonded to each other to form a saturated or unsaturated ring; and o, p, and q each independently represent an integer of 0 to 4, and r and s each independently represent an integer of 0 to 3; and the $L^2$ represents a single bond, or a linking group represented by any one of the general formulae (10) to (12);

(4) the aromatic amine derivative according to any one of the above-mentioned items (1) to (3), in which the $L^1$ represents a linking group represented by any one of the general formulae (10) to (12), and the $L^2$ represents a single bond;

(5) the aromatic amine derivative according to any one of the above-mentioned items (1) to (4), in which the $L^1$ represents any one of a phenylene group, a biphenylene group, and a 9,9-dimethylfluorenylene group, and the $L^2$ represents a single bond;

(6) the aromatic amine derivative according to any one of the above-mentioned items (1) to (5), in which the A represents a linking group represented by the general formula (2);

(7) the aromatic amine derivative according to any one of the above-mentioned items (1) to (5), in which the A represents a linking group represented by the general formula (3);

(8) the aromatic amine derivative according to any one of the above-mentioned items (1) to (5), in which the A represents a linking group represented by the general formula (4);

(9) the aromatic amine derivative according to any one of the above-mentioned items (1) to (5), in which the A represents a linking group represented by the general formula (5);

(10) the aromatic amine derivative according to any one of the above-mentioned items (1) to (9), in which the B represents a substituent represented by the general formula (6);

(11) the aromatic amine derivative according to any one of the above-mentioned items (1) to (9), in which the B represents a substituent represented by the general formula (7);

(12) the aromatic amine derivative according to any one of the above-mentioned items (1) to (9), in which the B represents a substituent represented by the general formula (8);

(13) the aromatic amine derivative according to any one of the above-mentioned items (1) to (9), in which the B represents a substituent represented by the general formula (9);

(14) the aromatic amine derivative according to any one of the above-mentioned items (1) to (13), in which the aromatic amine derivative is represented by any one of the following general formulae (13) to (17):

[Chem. 5]

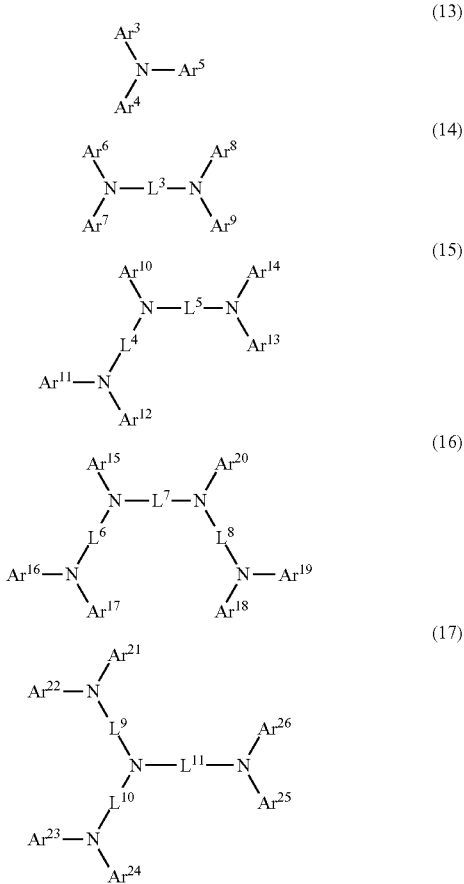

where at least one of Ar$^3$ to Ar$^5$, at least one of Ar$^6$ to Ar$^9$, at least one of Ar$^{10}$Ar$^{14}$, at least one of Ar$^{15}$ to Ar$^{20}$, and at least one of Ar$^{21}$ to Ar$^{26}$ are each represented by the general formula (1), and L$^3$ to L$^{11}$ each represent the same linking group as the linking group represented by the L$^2$;

(15) the aromatic amine derivative according to the above-mentioned item (14), in which the aromatic amine derivative is represented by the general formula (13);

(16) the aromatic amine derivative according to the above-mentioned item (15), in which at least one of the Ar$^3$, the Ar$^4$, and the Ar$^5$ is represented by the general formula (1), and the others each represent a substituted or unsubstituted aryl group having 6 to 50 ring carbon atoms;

(17) the aromatic amine derivative according to the above-mentioned item (14), in which the substituted or unsubstituted aryl group having 6 to 50 ring carbon atoms includes any one of a naphthyl group, a biphenyl group, and a terphenyl group;

(18) the aromatic amine derivative according to any one of the above-mentioned items (1) to (17), in which the aromatic amine derivative is used as a material for an organic electroluminescence device;

(19) the aromatic amine derivative according to any one of the above-mentioned items (1) to (17), in which the aromatic amine derivative is used as a hole transporting material for an organic electroluminescence device;

(20) an organic electroluminescence device, including an organic thin film layer formed of one or more layers including a light emitting layer, the organic thin film layer being interposed between a cathode and an anode, in which at least one layer of the organic thin film layer contains the aromatic amine derivative according to any one of the above-mentioned items (1) to (17);

(21) the organic electroluminescence device according to the above-mentioned item (20), in which: the organic thin film layer has a hole transporting layer and/or a hole injecting layer; and the aromatic amine derivative according to any one of the above-mentioned items (1) to (17) is incorporated into the hole transporting layer and/or the hole injecting layer;

(22) the organic electroluminescence device according to the above-mentioned item (21), in which: the organic thin film layer has a hole transporting zone including a hole transporting layer and/or a hole injecting layer; and the aromatic amine derivative according to any one of the above-mentioned items (1) to (17) is incorporated into a layer out of direct contact with the light emitting layer in the hole transporting zone;

(23) the organic electroluminescence device according to the above-mentioned item (21), in which the aromatic amine derivative according to any one of the above-mentioned items (1) to (17) is incorporated as a main component into the hole transporting layer and/or the hole injecting layer;

(24) the organic electroluminescence device according to any one of the above-mentioned items (20) to (23), in which the light emitting layer contains a styrylamine compound and/or an arylamine compound;

(25) the organic electroluminescence device according to any one of the above-mentioned items (20) to (23), in which a layer in contact with the anode out of layers for forming the hole injecting layer and/or the hole transporting layer includes a layer containing an acceptor material; and

(26) the organic electroluminescence device according to any one of the above-mentioned items (20) to (23), in which the organic electroluminescence device emits blue light.

Advantageous Effects of Invention

The aromatic amine derivative of the present invention hardly crystallizes, and the use of the derivative as a material for an organic EL device provides a device having a long lifetime even at high temperatures.

DESCRIPTION OF EMBODIMENTS

An aromatic amine derivative of the present invention is a compound having a substituent represented by the general formula (1).

First, L$^1$ and L$^2$ are described.

In the general formula (1), L$^1$ represents a substituted or unsubstituted arylene group having 6 to 50, preferably 6 to 15 ring carbon atoms, and L$^2$ represents a single bond, or a substituted or unsubstituted arylene group having 6 to 50, preferably 6 to 15 ring carbon atoms.

Cases where the L$^1$ represents any one of the general formulae (10) to (12), and the L$^2$ represents a single bond or any one of the general formulae (10) to (12) are preferred. Of those, the case where L$^1$ represents any one of a phenylene group, a biphenylene group, and a 9,9-dimethylfluorenylene group, and L$^2$ represents a single bond is preferred from the viewpoint of ease of synthesis.

Specific examples of the arylene group include arylene groups such as a phenylene group, a biphenylene group, a terphenylene group, a tetrafluorophenylene group, a dimethylphenylene group, a naphthylene group, an anthranylene group, a phenanthrylene group, a pyrenylene group, a naphthacenylene group, a quarterphenylene group, a pentacenylene group, a perylenylene group, a pyrenylene group, a coronylene group, a fluorenylene group, and an acenaphthofluorenylene group.

A substituent for each of $L^1$ to $L^2$ is a linear or branched alkyl group having 1 to 10, preferably 1 to 6 carbon atoms, a cycloalkyl group having 3 to 10, preferably 5 to 7 ring carbon atoms, a trialkylsilyl group having 3 to 10, preferably 3 to 6 carbon atoms, a triarylsilyl group having 18 to 30, preferably 18 to 24 ring carbon atoms, an alkylarylsilyl group having 8 to 24, preferably 8 to 12 carbon atoms (its aryl portion has 6 to 14, preferably 6 to 10 ring carbon atoms), an aryl group having 6 to 30, preferably 6 to 10 ring carbon atoms, a halogen atom, or a cyano group.

Specific examples of the alkyl group include a methyl group, an ethyl group, a propyl group, an isopropyl group, an n-butyl group, an isobutyl group, a sec-butyl group, a tert-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, and a 1,2,3-trihydroxypropyl group. Preferred are a methyl group, an ethyl group, a propyl group, an isopropyl group, an n-butyl group, an isobutyl group, a sec-butyl group, and a tert-butyl group.

Specific examples of the cycloalkyl group include a cyclopropyl group, a cyclobutyl group, a cyclopentyl group, a cyclohexyl group, a cyclopentylmethyl group, a cyclohexylmethyl group, a cyclohexylethyl group, a 4-fluorocyclohexyl group, a 1-adamantyl group, a 2-adamantyl group, a 1-norbornyl group, and a 2-norbornyl group. Preferred are a cyclopentyl group and a cyclohexyl group.

Specific examples of the trialkylsilyl group include a trimethylsilyl group, a vinyldimethylsilyl group, a triethylsilyl group, a tripropylsilyl group, a propyldimethylsilyl group, a tributylsilyl group, a t-butyldimethylsilyl group, a tripentylsilyl group, a triheptylsilyl group, and a trihexylsilyl group. Preferred are a trimethylsilyl group and a triethylsilyl group. A silyl group may be substituted with alkyl groups identical to or different from each other.

Specific examples of the triarylsilyl group include a triphenylsilyl group, a trinaphthylsilyl group, and a trianthrylsilyl group. Preferred is a triphenylsilyl group. A silyl group may be substituted with aryl groups identical to or different from each other.

Specific examples of the alkylarylsilyl group include a dimethylphenylsilyl group, a diethylphenylsilyl group, a dipropylphenylsilyl group, a dibutylphenylsilyl group, a dipentylphenylsilyl group, a diheptylphenylsilyl group, a dihexylphenylsilyl group, a dimethylnaphthylsilyl group, a dipropylnaphthylsilyl group, a dibutylnaphthylsilyl group, a dipentylnaphthylsilyl group, a diheptylnaphthylsilyl group, a dihexylnaphthylsilyl group, a dimethylanthrylsilyl group, a diethylanthrylsilyl group, a dipropylanthrylsilyl group, a dibutylanthrylsilyl group, a dipentylanthrylsilyl group, a dihexylanthrylsilyl group, a diheptylanthrylsilyl group, and a diphenylmethyl group. Preferred are a dimethylphenylsilyl group, a diethylphenylsilyl group, and a diphenylmethyl group.

Specific examples of the aryl group include a phenyl group, a 2-methylphenyl group, a 3-methylphenyl group, a 4-methylphenyl group, a 4-ethylphenyl group, a biphenylyl group, a 4-methylbiphenylyl group, a 4-ethylbiphenylyl group, a 4-cyclohexylbiphenylyl group, an anthracenyl group, a naphthacenyl group, a terphenylyl group, a triphenylyl group, a 3,5-dichlorophenylyl group, a naphthyl group, a 5-methyl-naphthyl group, a phenanthryl group, a chrysenyl group, a benzophenanthryl group, a terphenyl group, a benzanthranyl group, a benzochrysenyl group, a pentacenyl group, a picenyl group, a pentaphenyl group, a pyrenyl group, a chrysenyl group, a fluorenyl group, an indenyl group, an acenaphthylenyl group, a fluoranthenyl group, and a perylenyl group. Of those, preferred are a phenyl group, a naphthyl group, a biphenylyl group, a terphenylyl group, and a fluorenyl group. More preferred are a phenyl group, a biphenylyl group, and a terphenylyl group.

Specific examples of the halogen atom include fluorine, chlorine, and bromine.

Further, it is preferred that the $L^1$ represent any one of the general formulae (10) to (12), and the $L^2$ represent a single bond or any one of the general formulae (10) to (12).

$R^{15}$ to $R^{19}$ each independently represent the same substituent as the arbitrary substituent for each of the $L^1$ and the $L^2$, and a specific example of the substituent is also the same substituent as the arbitrary substituent for each of the $L^1$ and the $L^2$.

$R^{20}$ and $R^{21}$ each independently represent a linear or branched alkyl group formed of a hydrocarbon having 1 to 10, preferably 1 to 6 carbon atoms, or a cycloalkyl group having 3 to 10, preferably 5 to 7 ring carbon atoms. A plurality of $R^{15}$'s, $R^{16}$'s, $R^{17}$'s, $R^{18}$'s, or $R^{19}$'s adjacent to each other may be bonded to each other to form a saturated or unsaturated ring.

o, p, and q each independently represent an integer of 0 to 4. r and s each independently represent an integer of 0 to 3.

Specific examples of the alkyl group and the cycloalkyl group represented by $R^{20}$ and $R^{21}$ include those each described as a substituent for each of the $L^1$ and the $L^2$ (arylene group).

Next, A is described.

A of the general formula (1) represents a linking group represented by any one of the general formulae (2) to (5) or by a general formula $<-L^{2'}-B'-(L^{2'}$ have the same meaning as that of the above-mentioned $L^2$, and B' represents any one of the general formulae (2) to (5))$>$.

In the general formulae (2) to (5), $R^1$ to $R^7$ each independently represent the same substituent as the arbitrary substituent for each of the $L^1$ and the $L^2$, or a group represented by a general formula $<-L^2-B$ ($L^2$ and B each have the same meaning as that described above)$>$. Specific examples of the substituent and the group are also the same as those in the case of the arbitrary substituent for each of the $L^1$ and the $L^2$.

In the general formulae (2) to (5), a plurality of $R^1$'s, $R^2$'s, $R^3$'s, $R^4$'s, $R^5$'s, $R^6$'s, or $R^7$'s, adjacent to each other may be bonded to each other to form a saturated or unsaturated ring, d represents an integer of 0 to 4, preferably 0 or 1, a, b, c, e, and f each independently represent an integer of 0 to 3, preferably 0 or 1, and g represents an integer of 0 to 2, preferably 0 or 1.

$Ar^1$ represents an aryl group having 6 to 14, preferably 6 to 10 ring carbon atoms.

Specific examples of the aryl group include those each having 6 to 14 ring carbon atoms out of the examples of the substituent for the arylene group.

Substituents for $Ar^1$ are each independently the same substituent as the arbitrary substituent for each of the $L^1$ and the $L^2$. Specific examples of the substituent are also the same as those in the case of the arbitrary substituent for each of the $L^1$ and the $L^2$.

Particularly preferred out of the aromatic amine derivatives each having a substituent represented by the general formula (1) of the present invention is an aromatic amine derivative having such a substituent that the A represents a linking group represented by any one of the general formulae (2) to (4), and the B is represented by any one of the general formulae (6) to (8), more preferably the general formula (6) or (7).

Next, B is described.

B of the general formula (1) is represented by any one of the substituents represented by the general formulae (6) to (9). Of those, a substituent represented by any one of the general formulae (6) to (8) is preferred, and a substituent represented by the general formula (6) or (7) is more preferred.

In the general formulae (6) to (9), $R^8$ to $R^{14}$ each independently represent the same substituent as the arbitrary substituent for each of the $L^1$ and the $L^2$, or a group represented by a general formula [-$L^2$-B ($L^2$ and B each have the same meaning as that described above)]. A plurality of $R^1$'s, $R^2$'s, $R^3$'s, $R^4$'s, $R^5$'s, $R^6$'s or $R^7$'s adjacent to each other may be bonded to each other to form a saturated or unsaturated ring. Specific examples of the substituent and the group are also the same as those in the case of the arbitrary substituent for each of the $L^1$ and the $L^2$.

In the general formulae (6) to (9), i, j, k, and m each independently represent an integer of 0 to 4, preferably 0 or 1, and h, l, and n each independently represent an integer of 0 to 3, preferably 0 or 1.

$Ar^2$ represents an aryl group having 6 to 14, preferably 6 to 10 ring carbon atoms.

Specific examples of the aryl group include those each having 6 to 14 ring carbon atoms out of the examples of the substituent for the $L^1$ and the $L^2$ (arylene group).

Substituents for $Ar^2$ are each independently any one of the same substituent as the arbitrary substituent for each of the $L^1$ and the $L^2$ (except an aryl group), a phenyl group, a biphenyl group, a naphthyl group, and a phenanthryl group.

When an aryl group having a high molecular weight is bonded to the N-position of carbazole in a terminal region of a molecule of the aromatic amine derivative, the molecule is thermally instable, and hence the possibility that the molecule decomposes at the time of its sublimation purification increases. Accordingly, the performance of a device using the derivative may reduce. Particularly in the case of such an aryl group that an amino group is bonded to the N-position of carbazole, the electron density characteristic of a terminal as a carbazole group reduces, and hence the device performance may reduce.

The aromatic amine derivative having a substituent represented by the general formula (1) of the present invention is preferably a compound represented by any one of the general formulae (13) to (17), particularly preferably a compound represented by the general formula (13).

In the general formulae (13) to (17), at least one of $Ar^3$ to $Ar^5$, at least one of $Ar^6$ to $Ar^9$, at least one of $Ar^{10}$ to $Ar^{14}$, at least one of $Ar^{15}$ to $Ar^{20}$, and at least one of $Ar^{21}$ to $Ar^{26}$ each represent the substituent represented by the general formula (1).

A substituent represented by any one of $Ar^3$ to $Ar^{26}$ except the substituent represented by the general formula (1) is a substituted or unsubstituted aryl group having 6 to 50, preferably 6 to 10 ring carbon atoms. Specific examples and preferred examples of the aryl group are the same as those listed in the foregoing description. A substituent for the aryl group is the same as a substituent for each of the $L^1$ and the $L^2$ (arylene group).

In the general formulae (13) to (17), $L^3$ to $L^{11}$ each have the same meaning as that of the $L^2$.

Preferred modes in the aromatic amine derivative represented by any one of the general formulae (13) to (17) are as follows:

(i) an aromatic amine derivative in which the $Ar^3$ is represented by the general formula (1), and the $Ar^4$ and the $Ar^5$ each independently represent a substituted or unsubstituted aryl group having 6 to 50 ring carbon atoms;

(ii) an aromatic amine derivative in which the $Ar^3$ and the $Ar^4$ are each independently represented by the general formula (1), and the $Ar^5$ represents a substituted or unsubstituted aryl group having 6 to 50 ring carbon atoms;

(iii) an aromatic amine derivative in which the $Ar^3$ to $Ar^5$ are each independently represented by the general formula (1); and (iv) an aromatic amine derivative in which a group out of the $Ar^3$ to $Ar^5$ which is not represented by the general formula (1) is a substituent represented by any one of a naphthyl group, a biphenyl group, and a terphenyl group.

Specific examples of the aromatic amine derivative having a substituent represented by the general formula (1) of the present invention include the following compounds.

[Chem. 6]

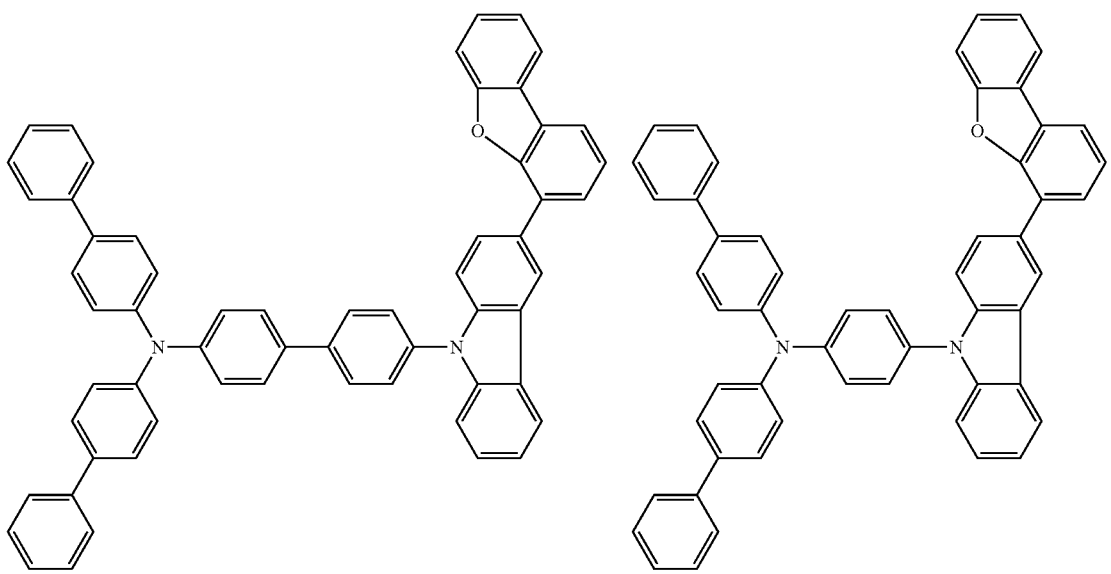

-continued
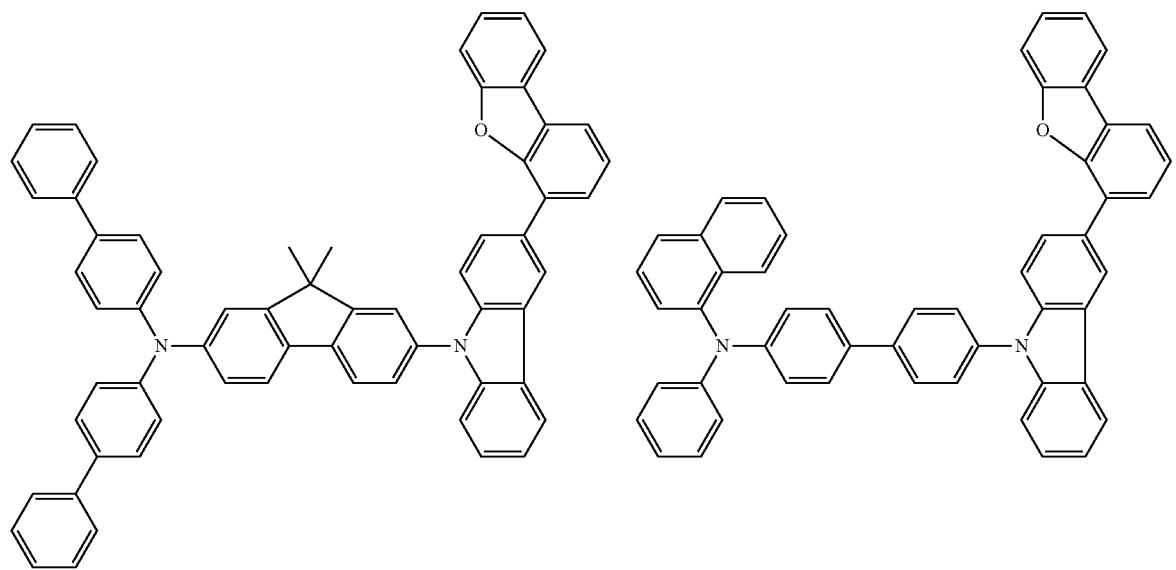
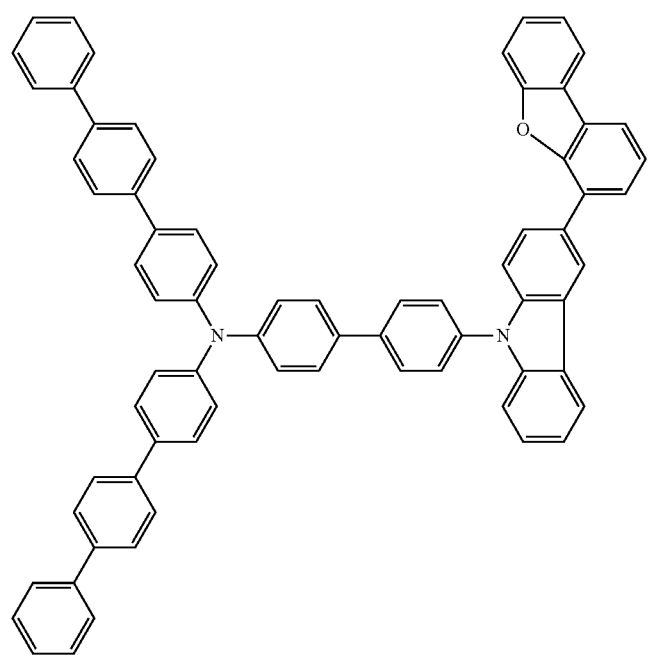

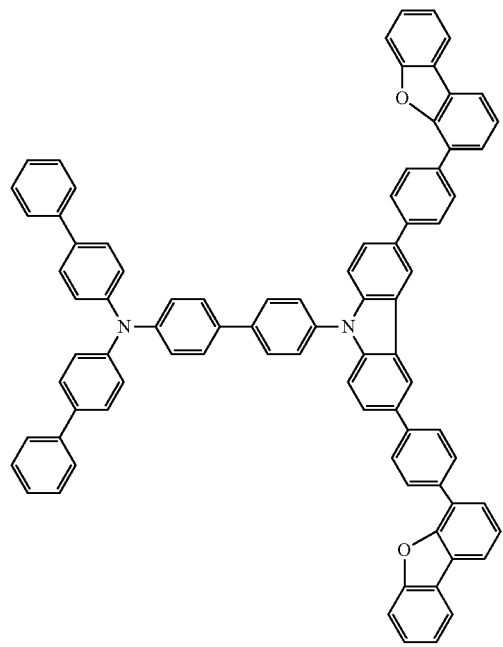
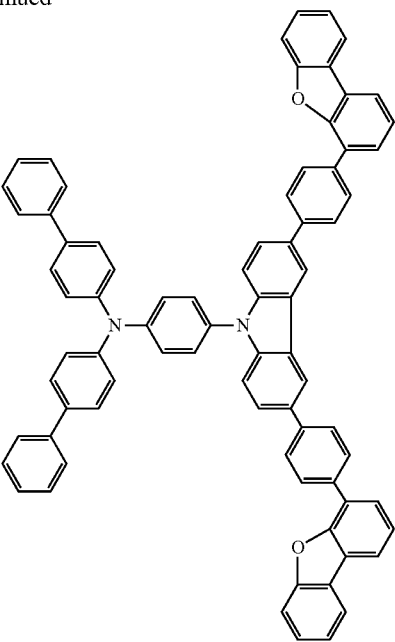
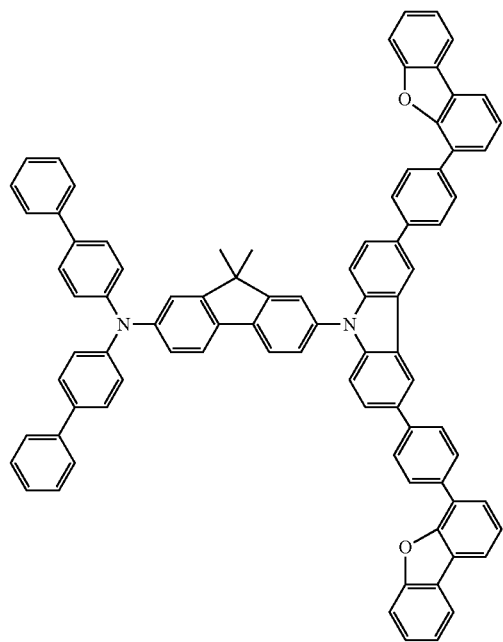

-continued
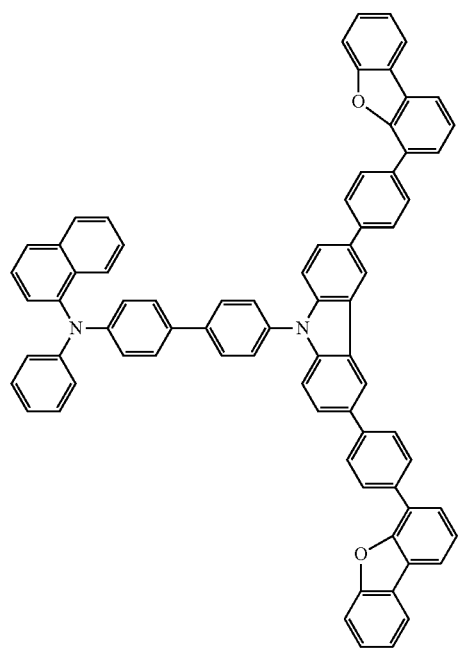
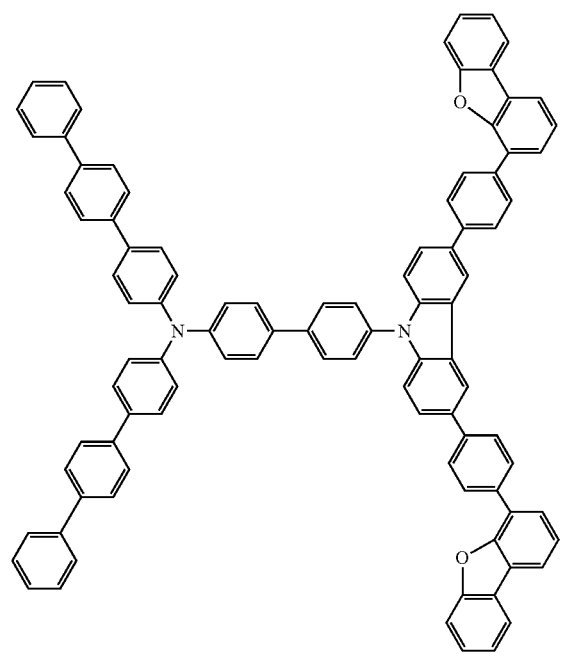

-continued
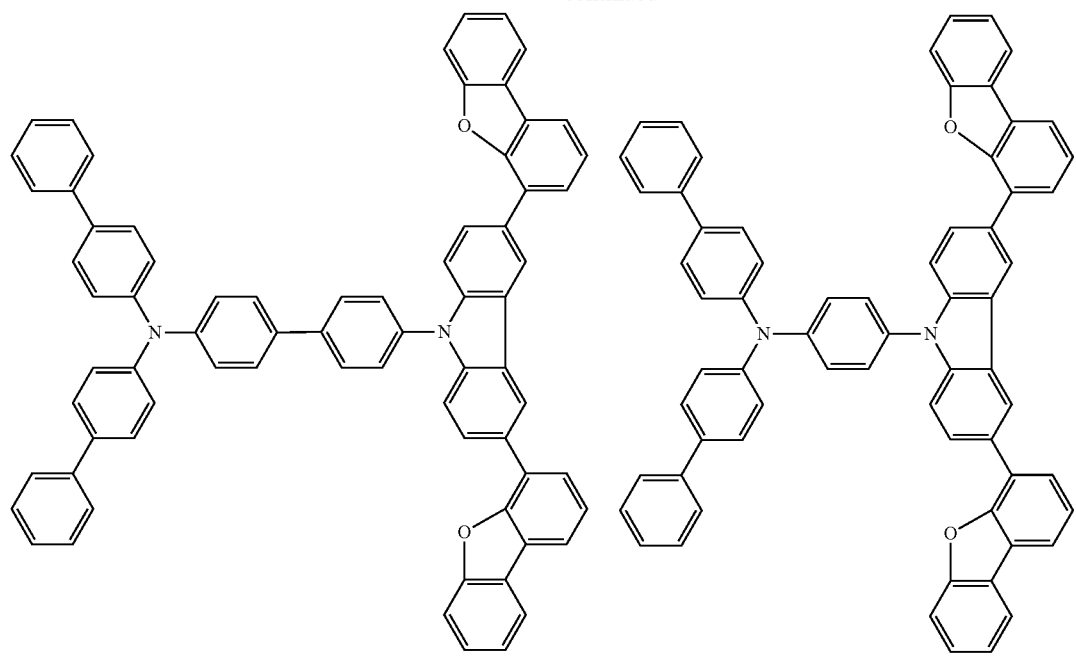
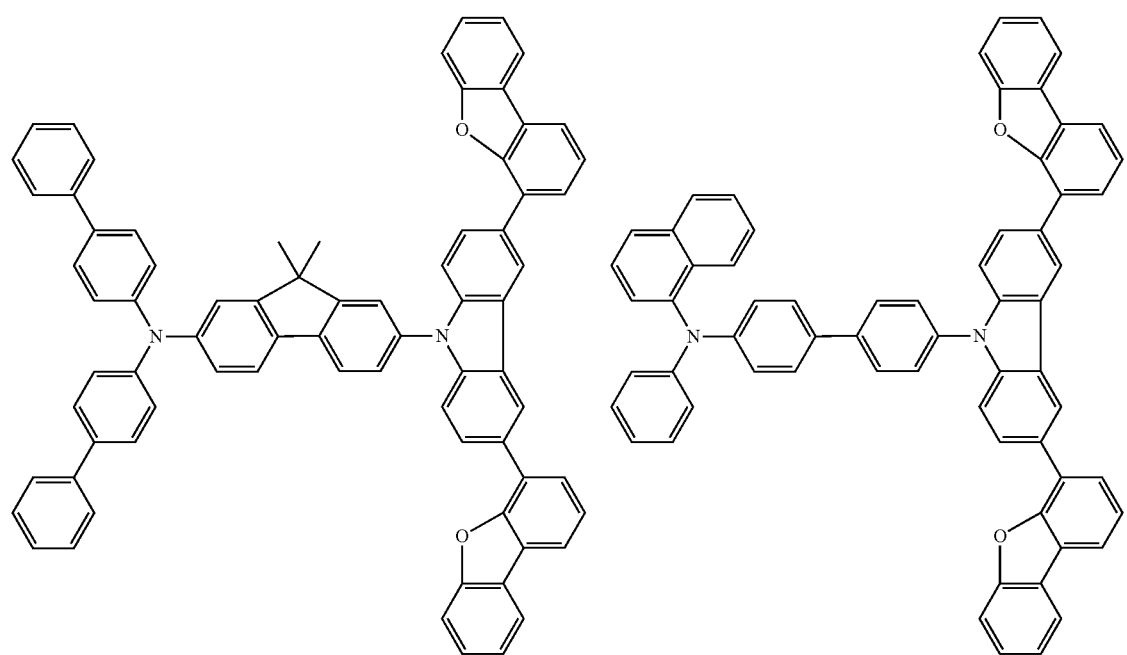

-continued
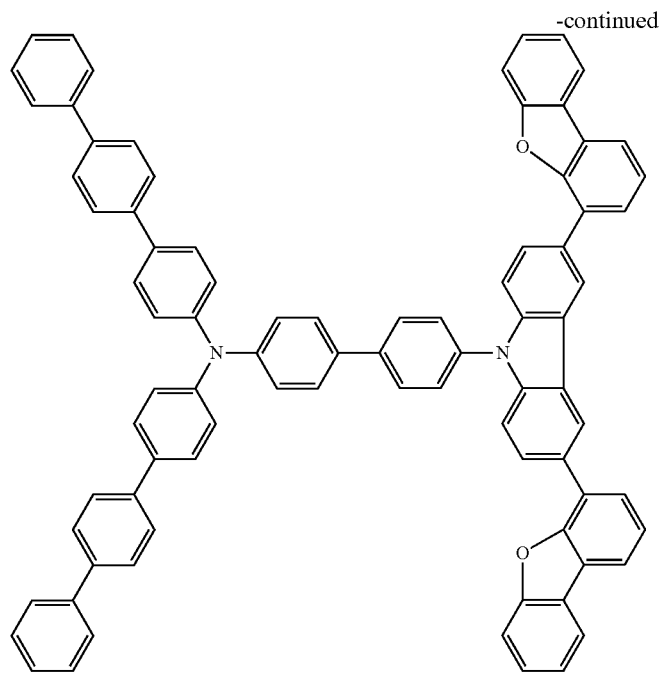
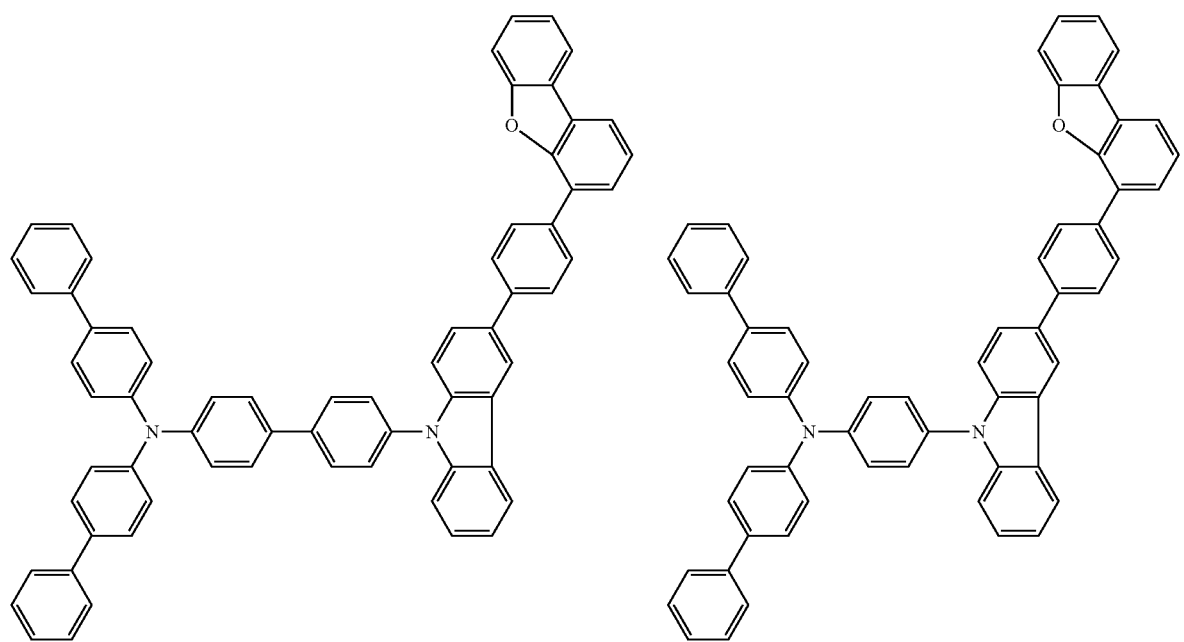

-continued
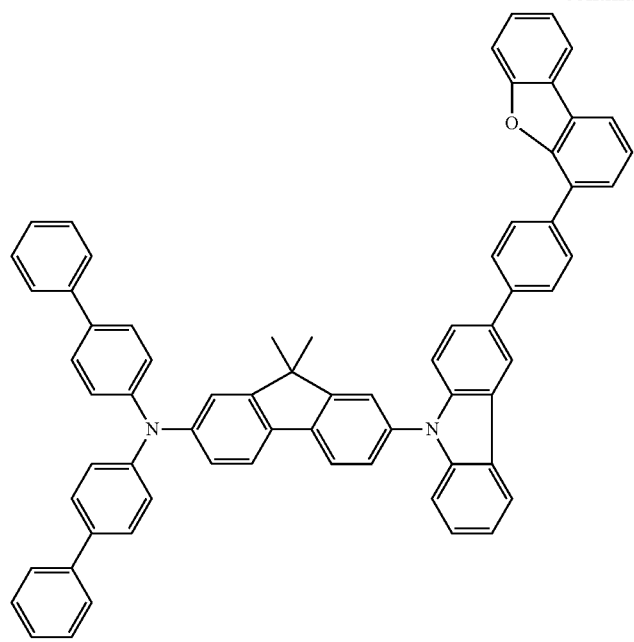
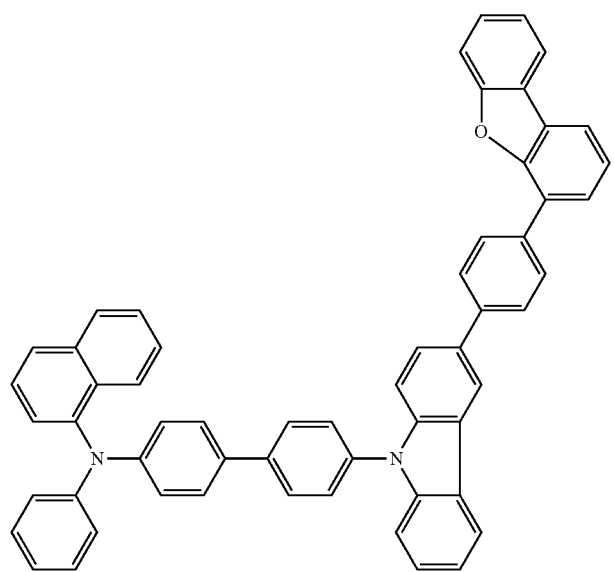

-continued
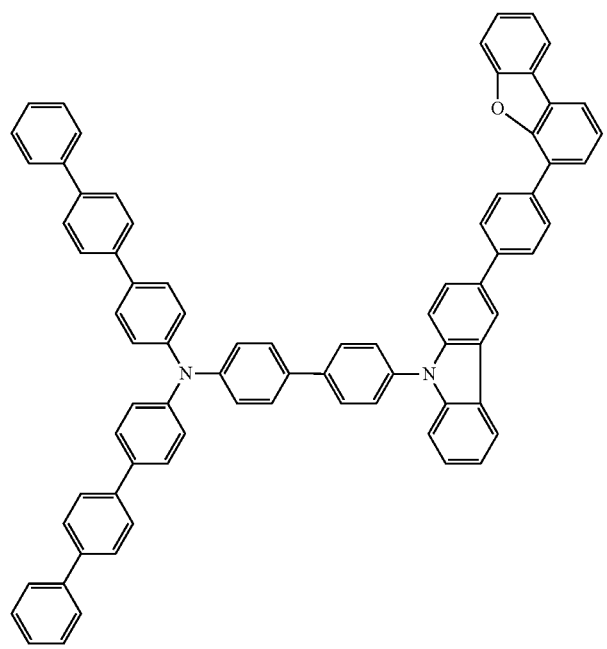
[Chem. 7]
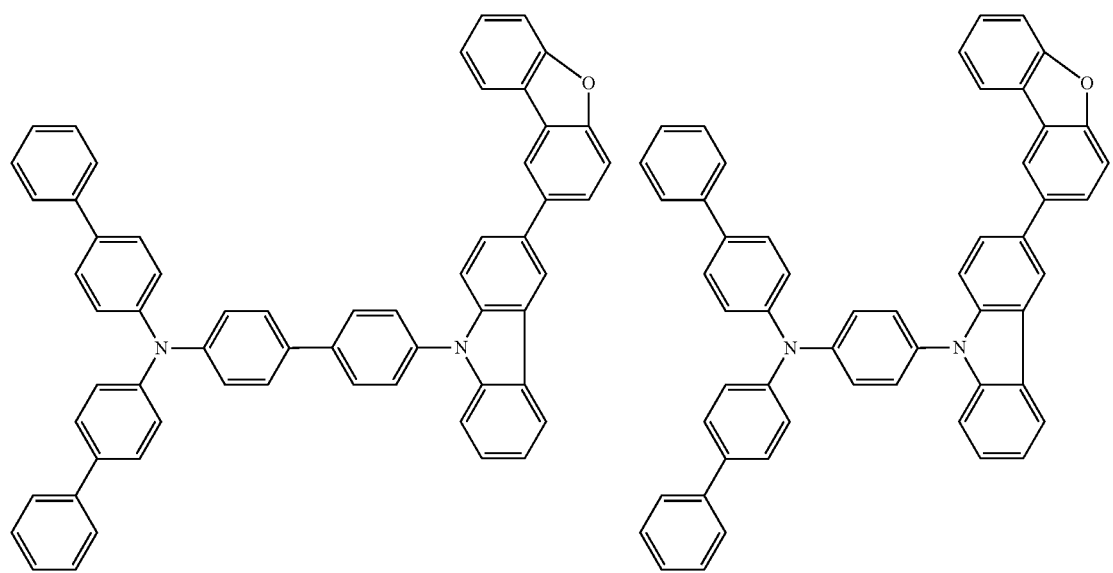

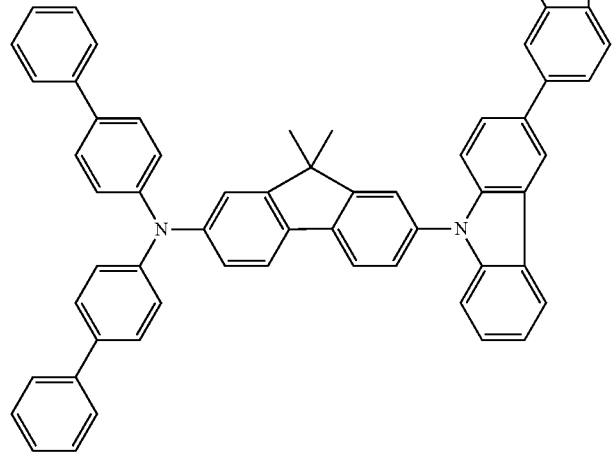
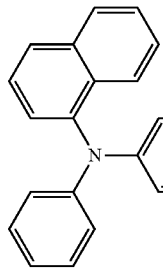
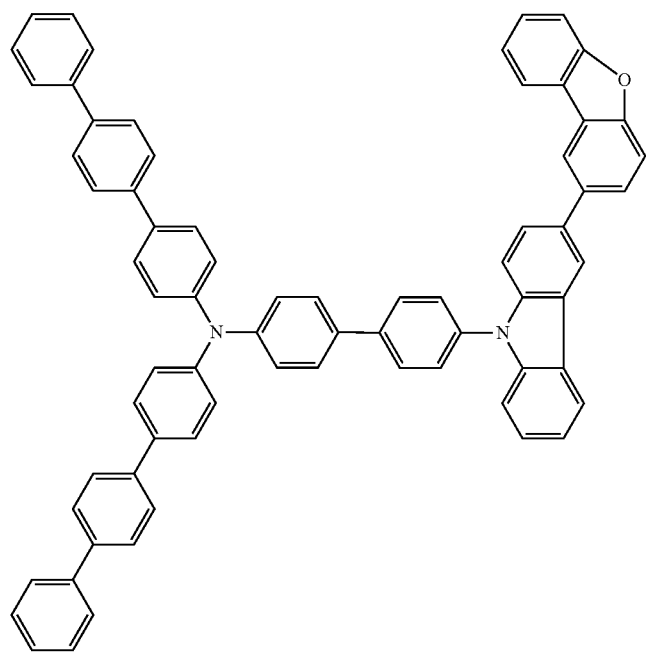

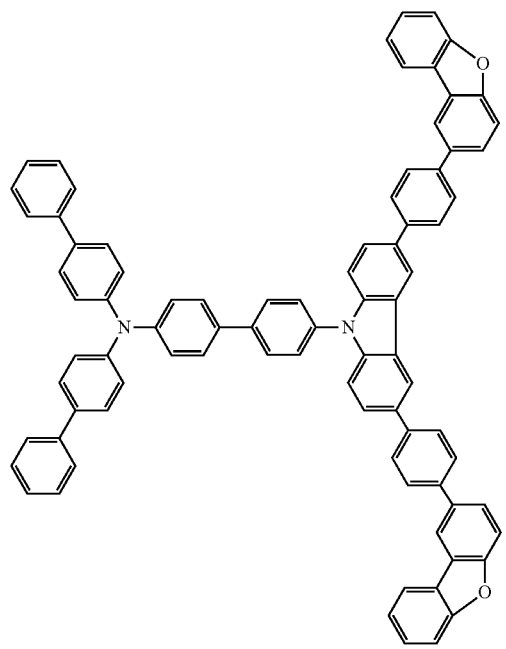
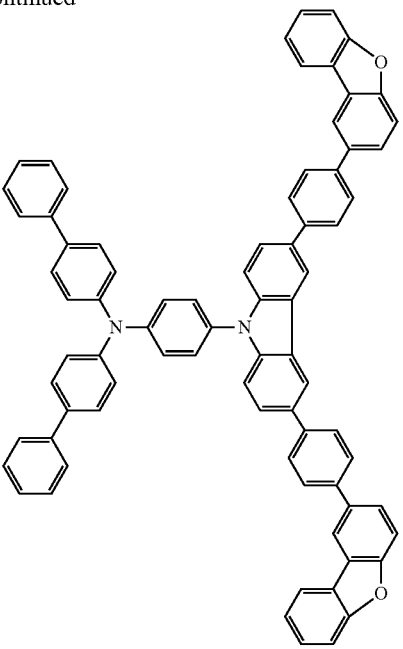
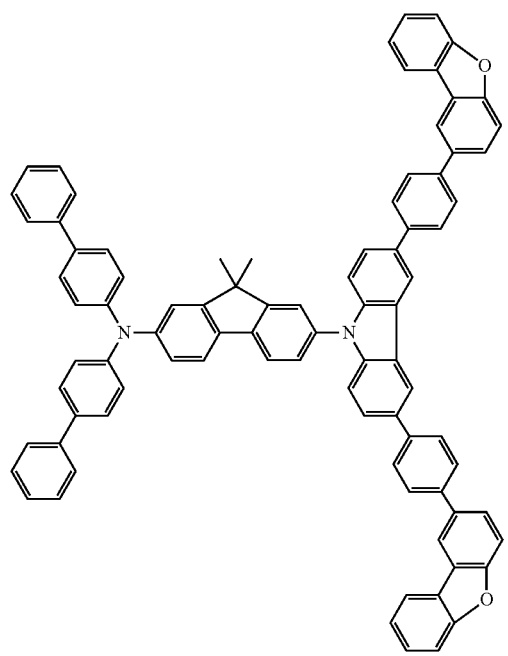

-continued
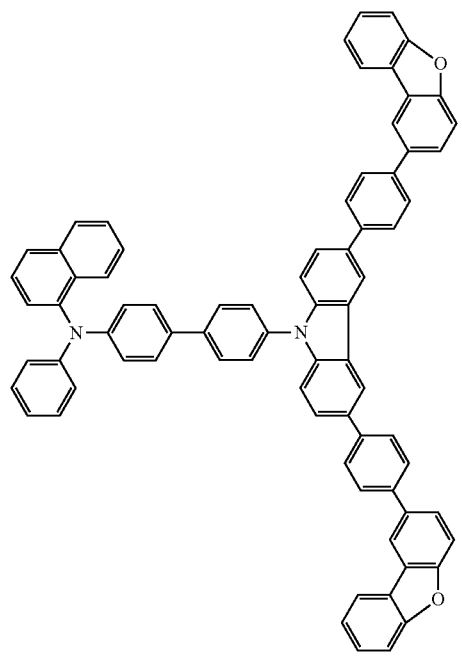
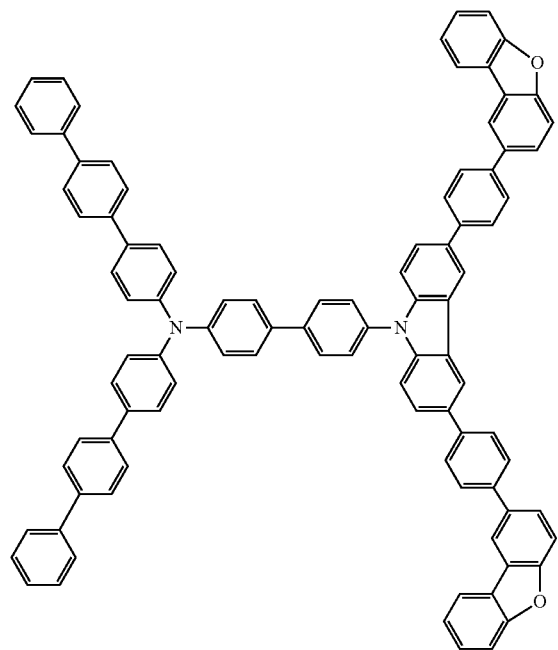

-continued
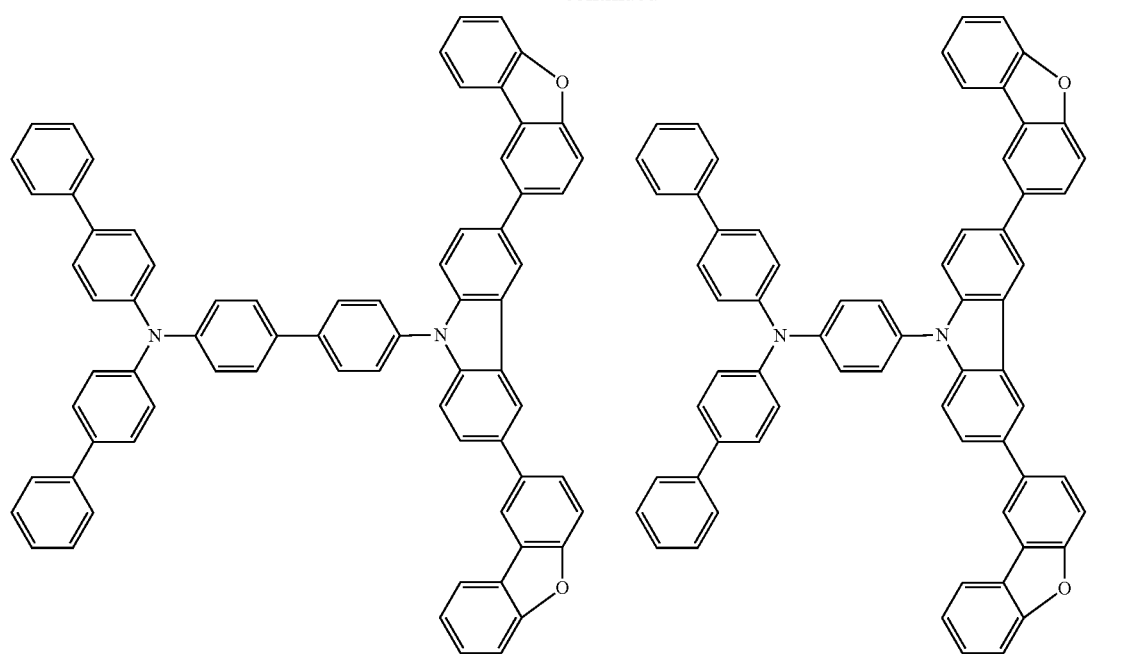
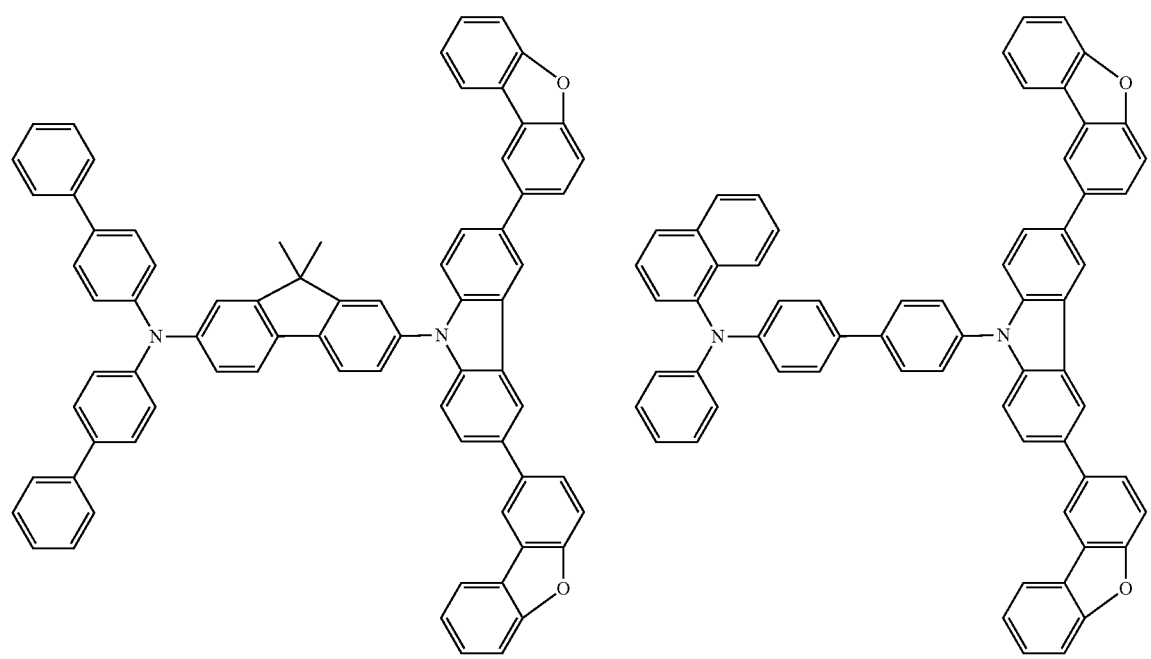

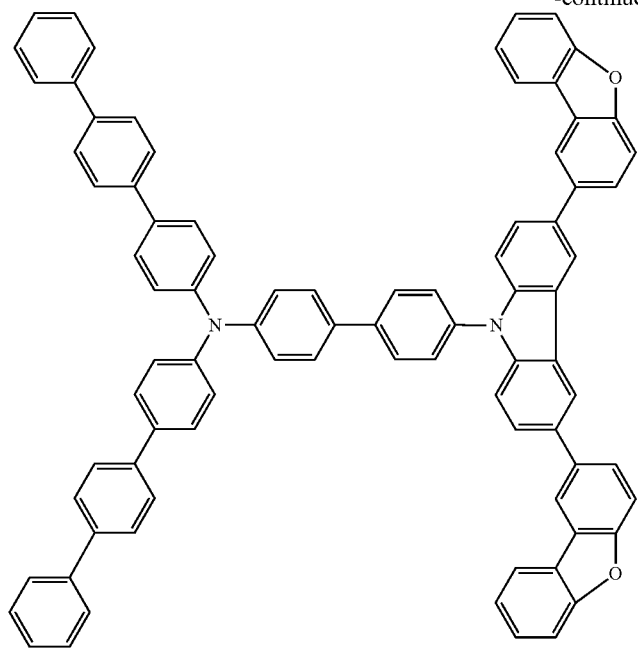
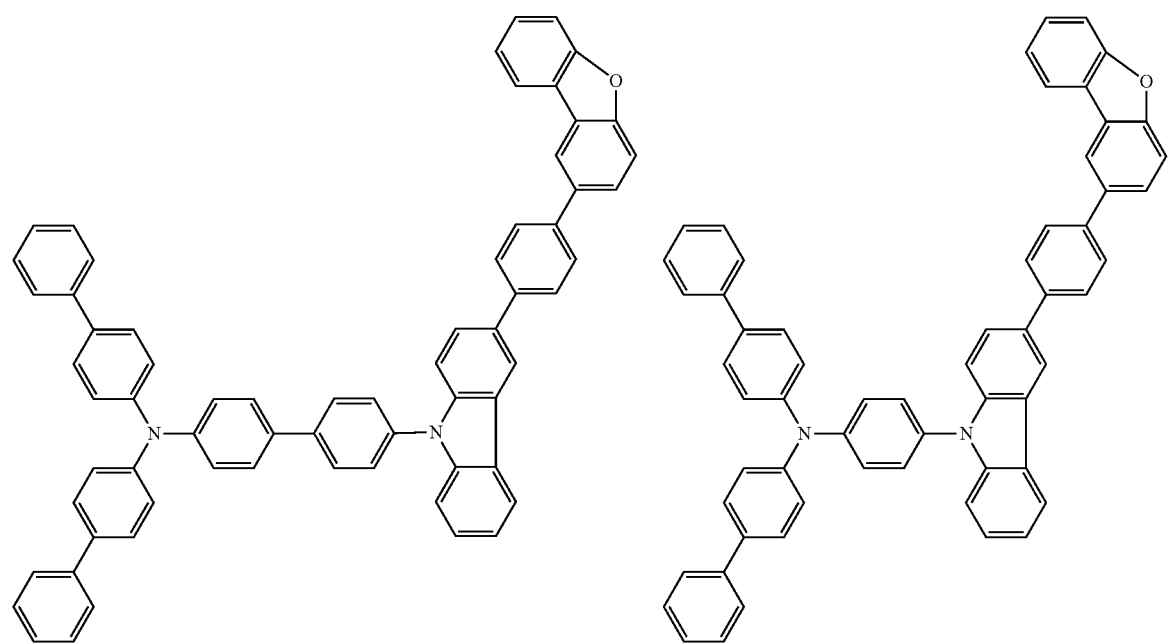

-continued
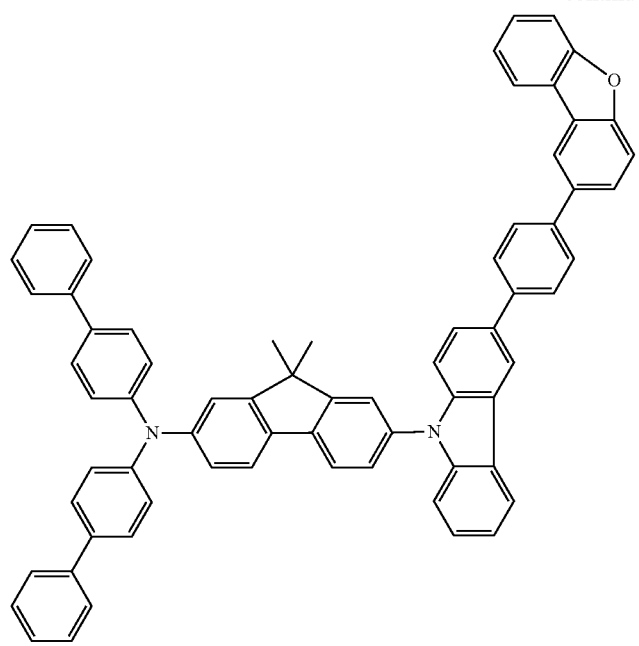
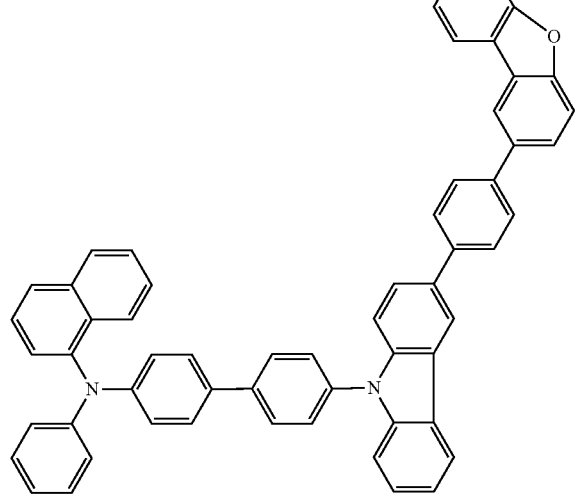

-continued
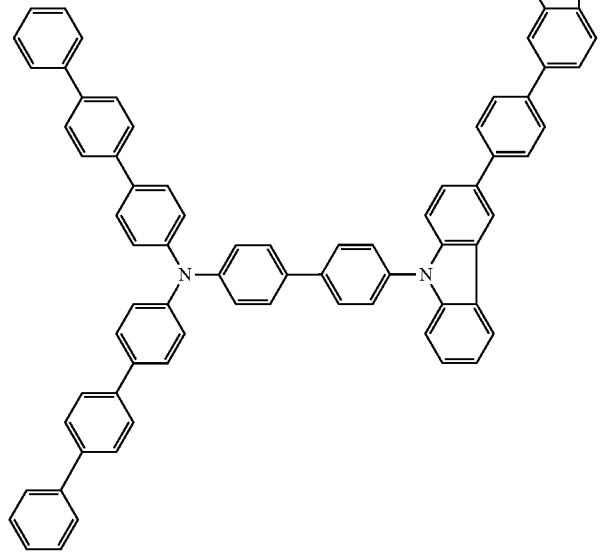
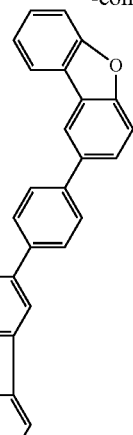
[Chem. 8]
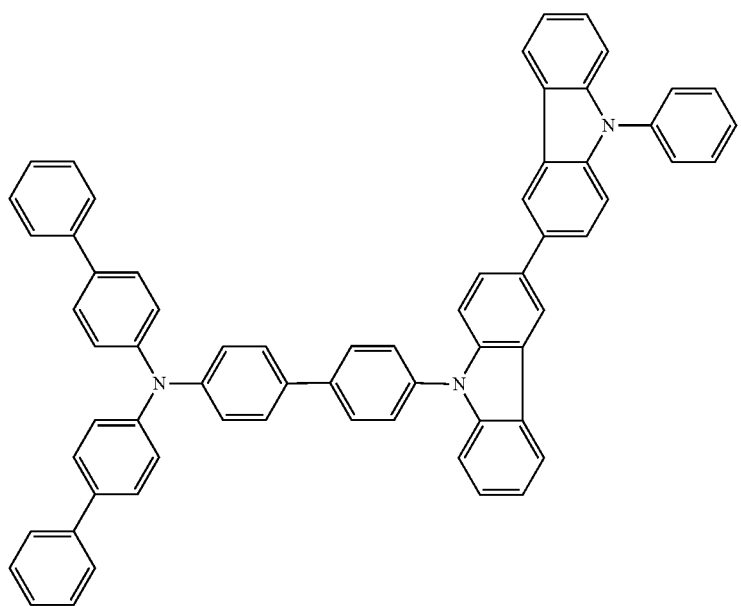

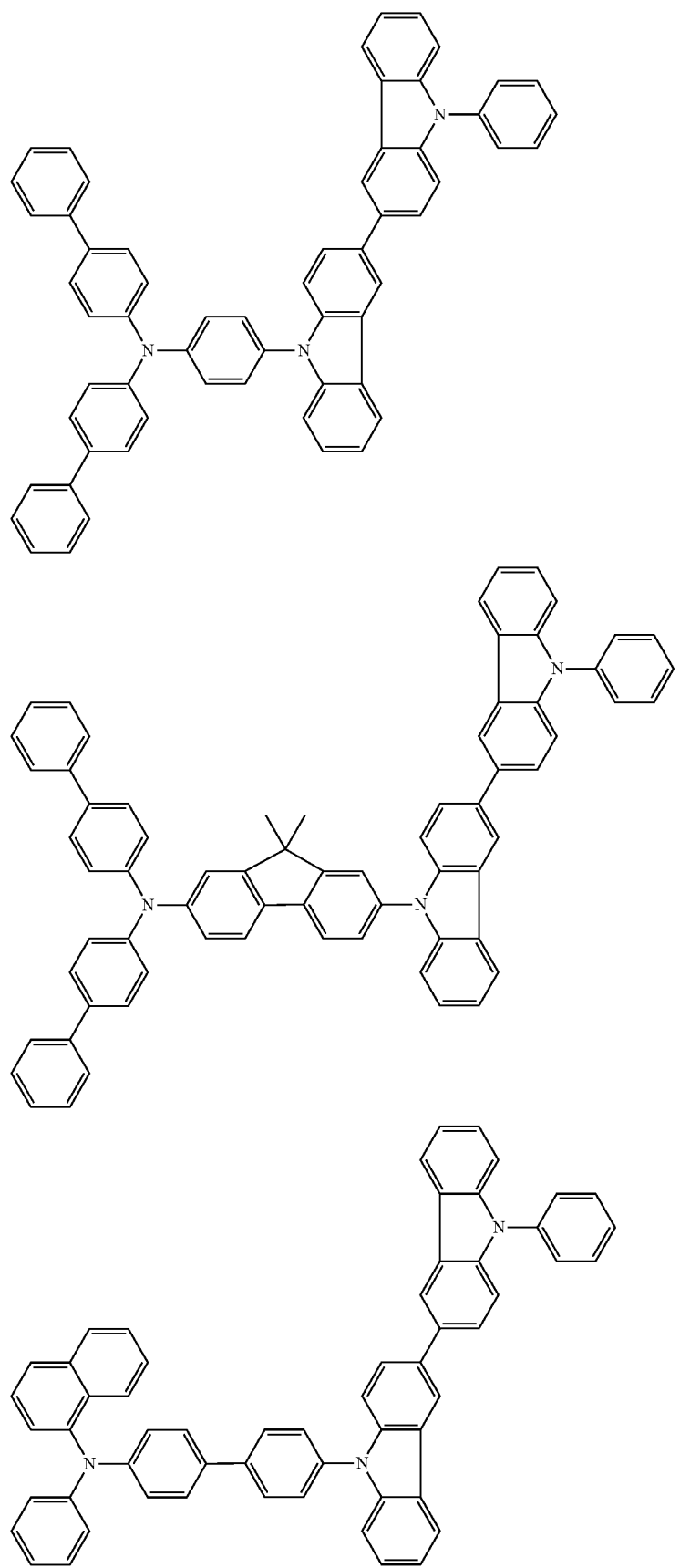

-continued
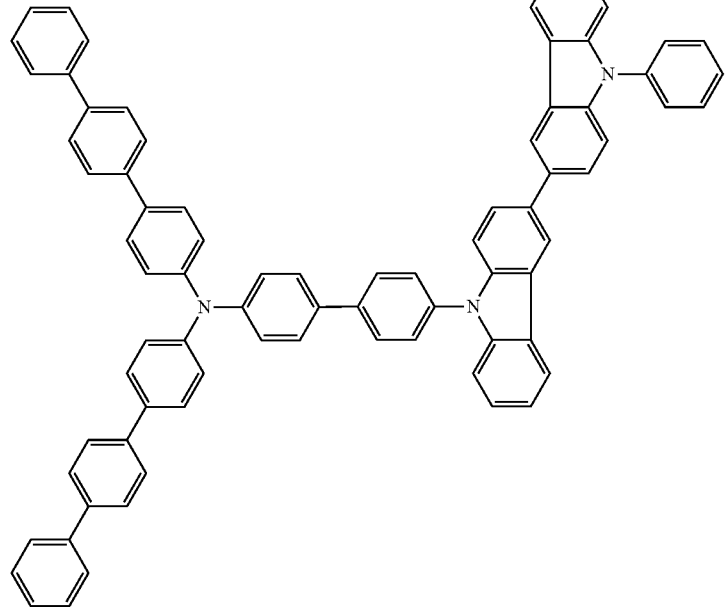
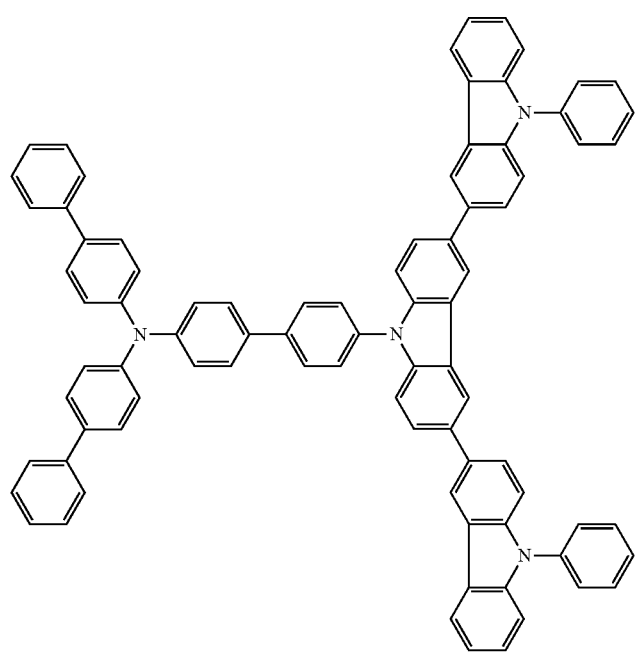

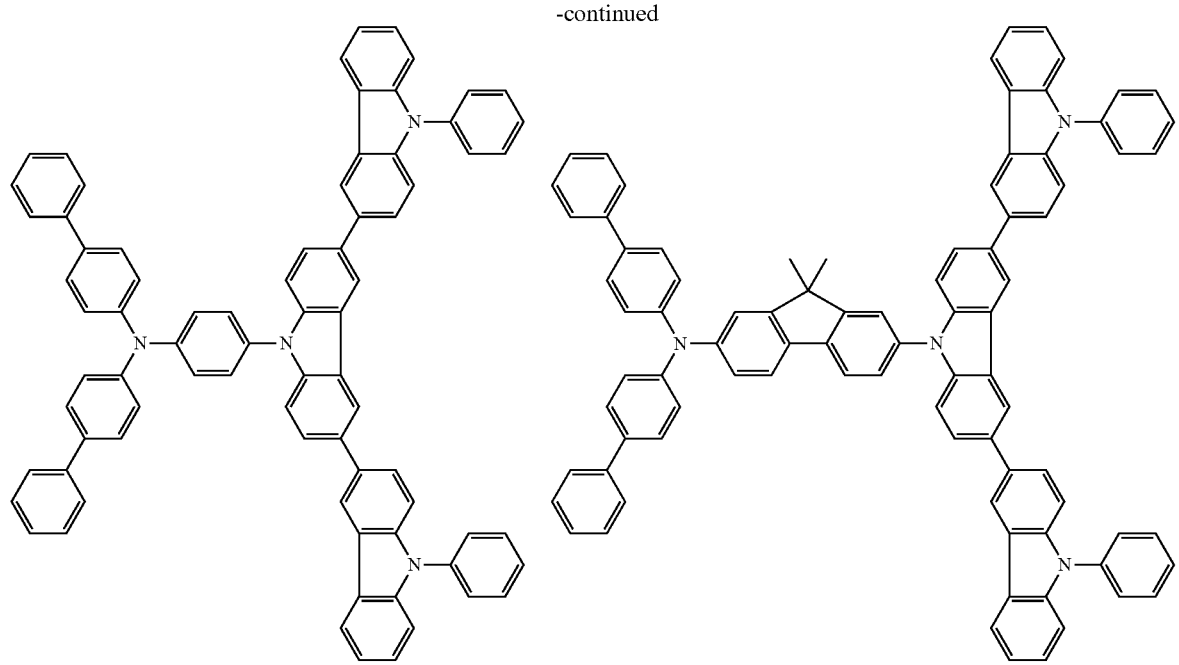
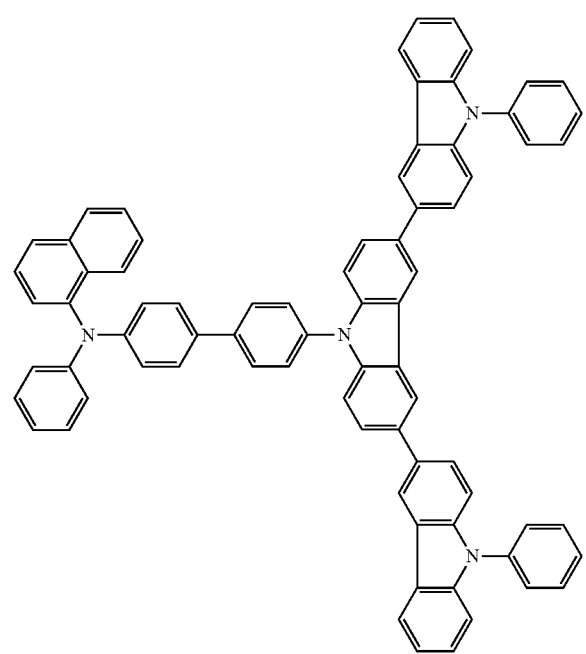

-continued
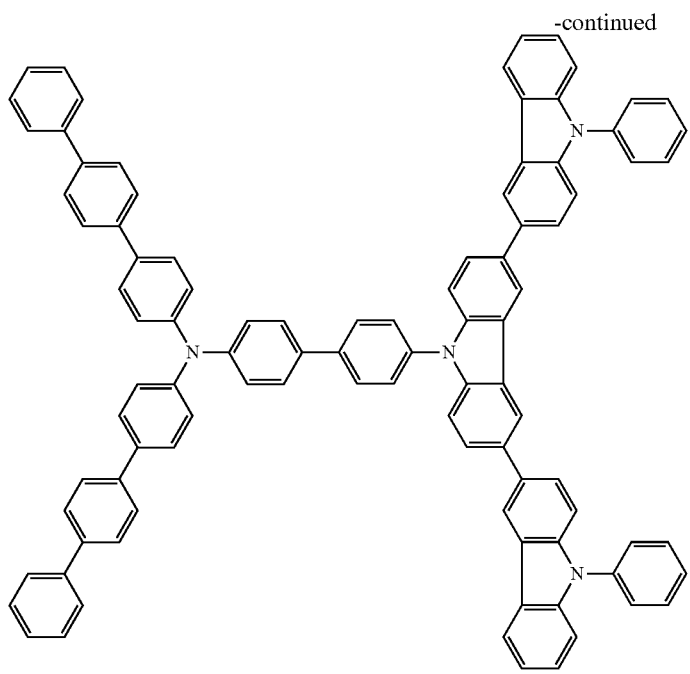
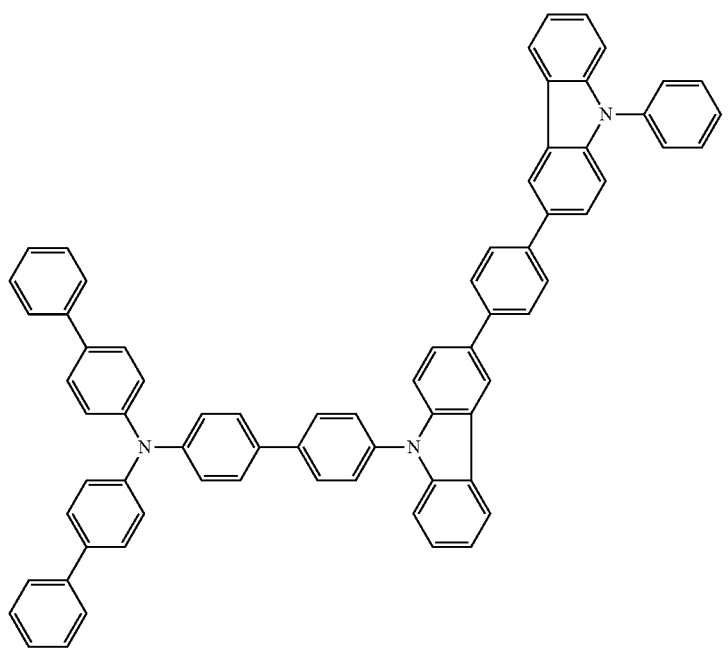

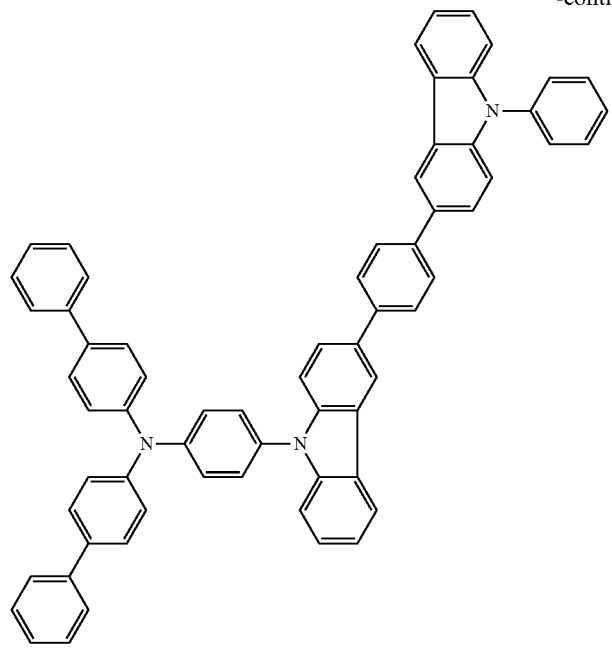
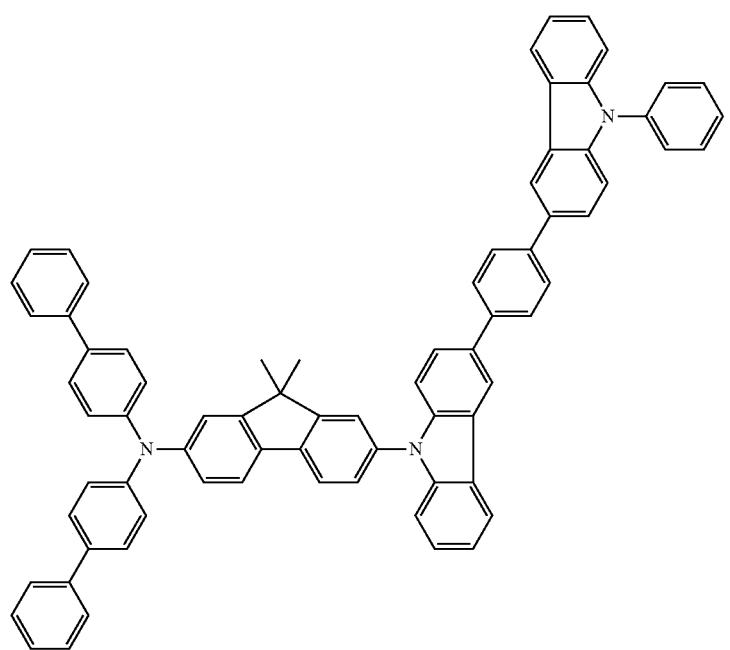

-continued
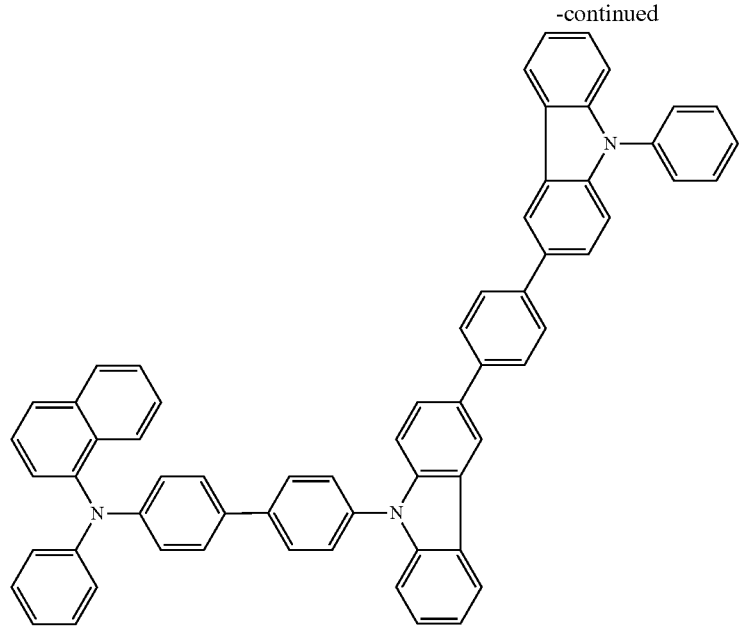
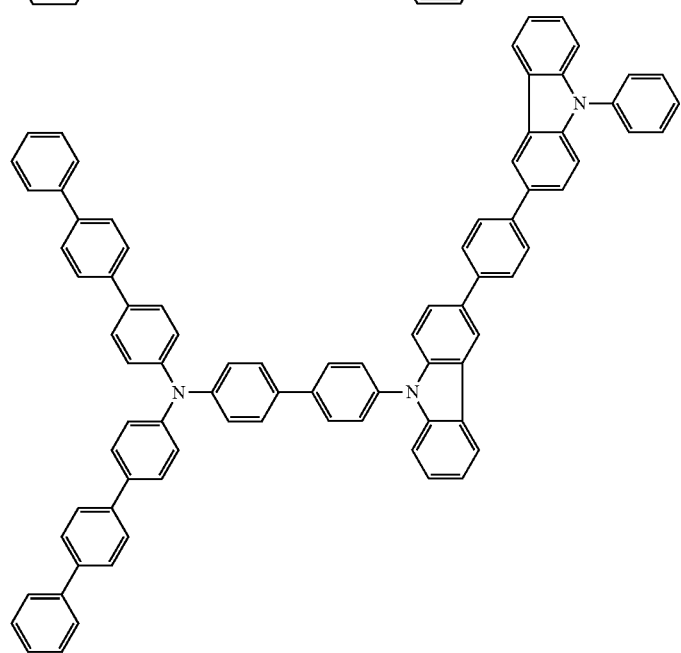
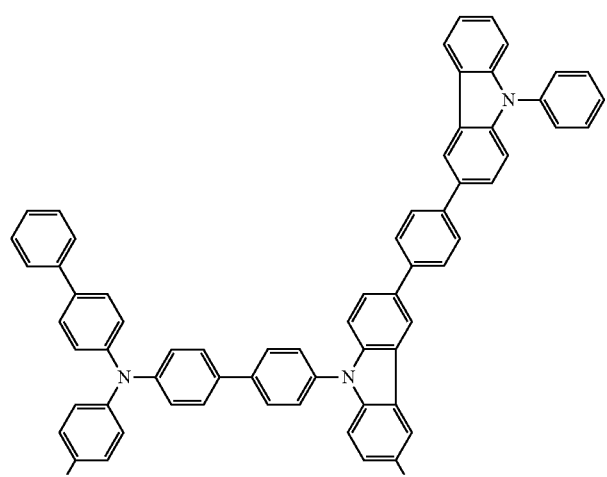

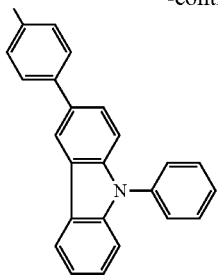
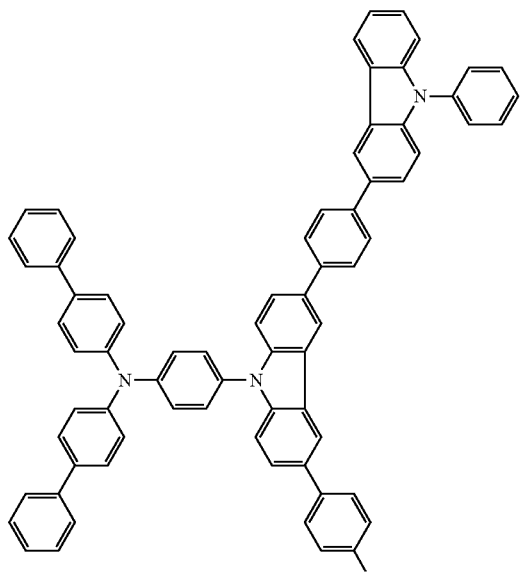
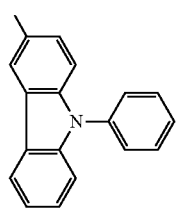
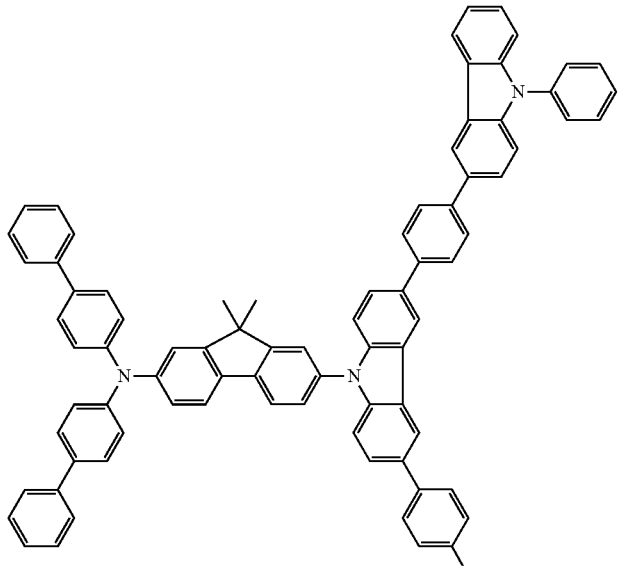

-continued
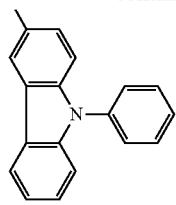
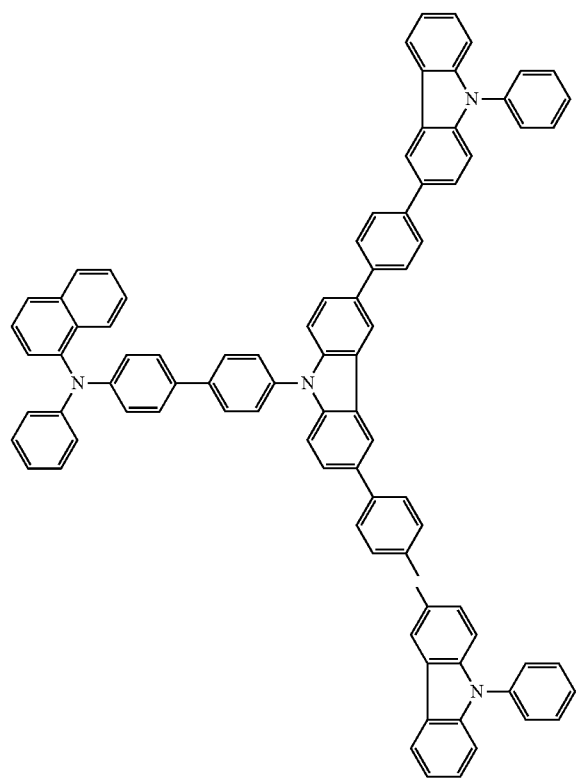
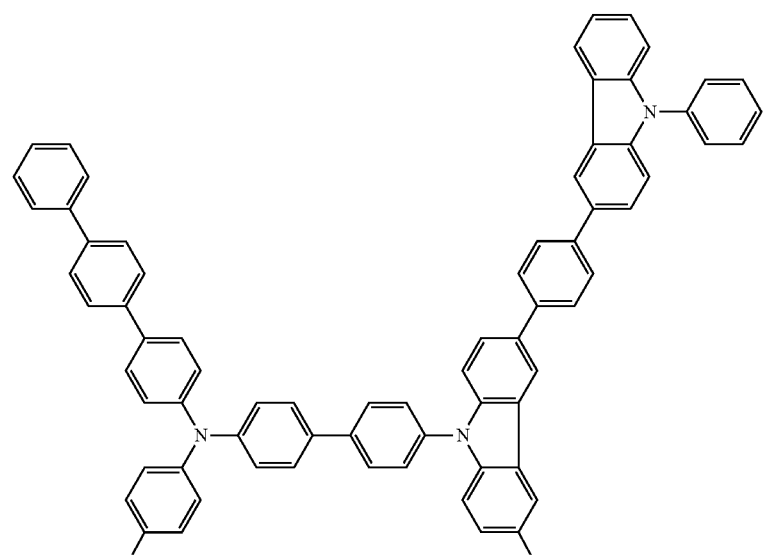

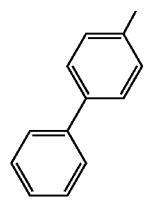
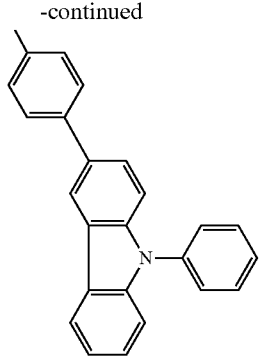
[Chem. 9]
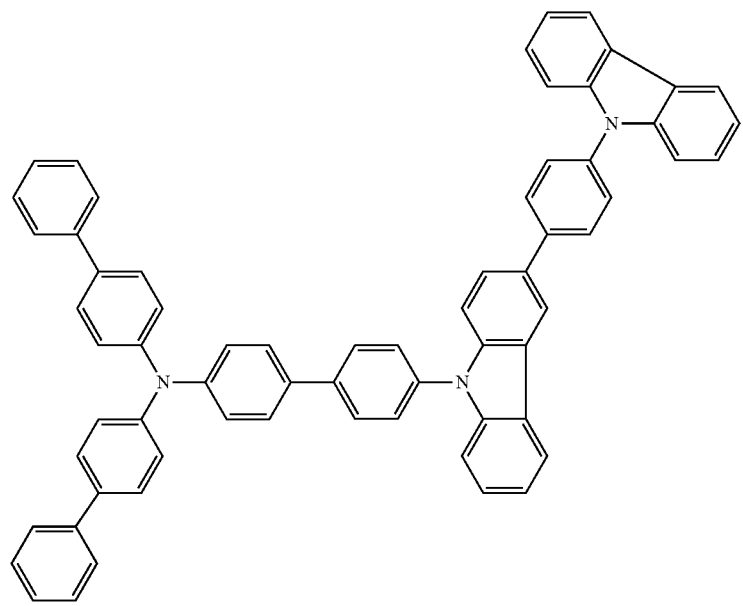
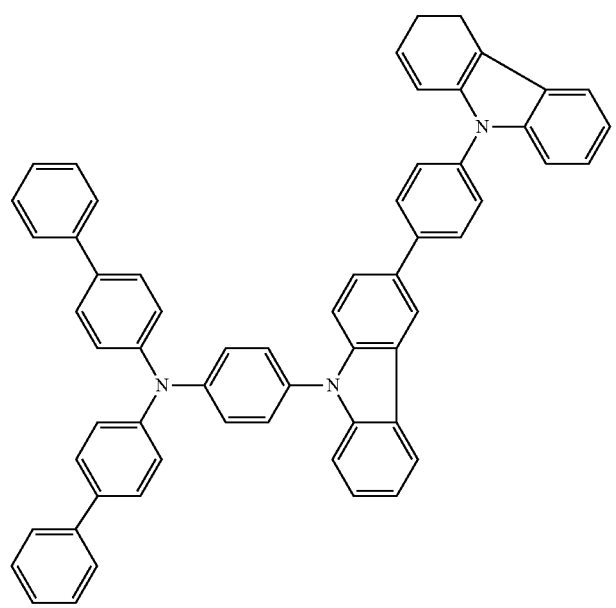

-continued
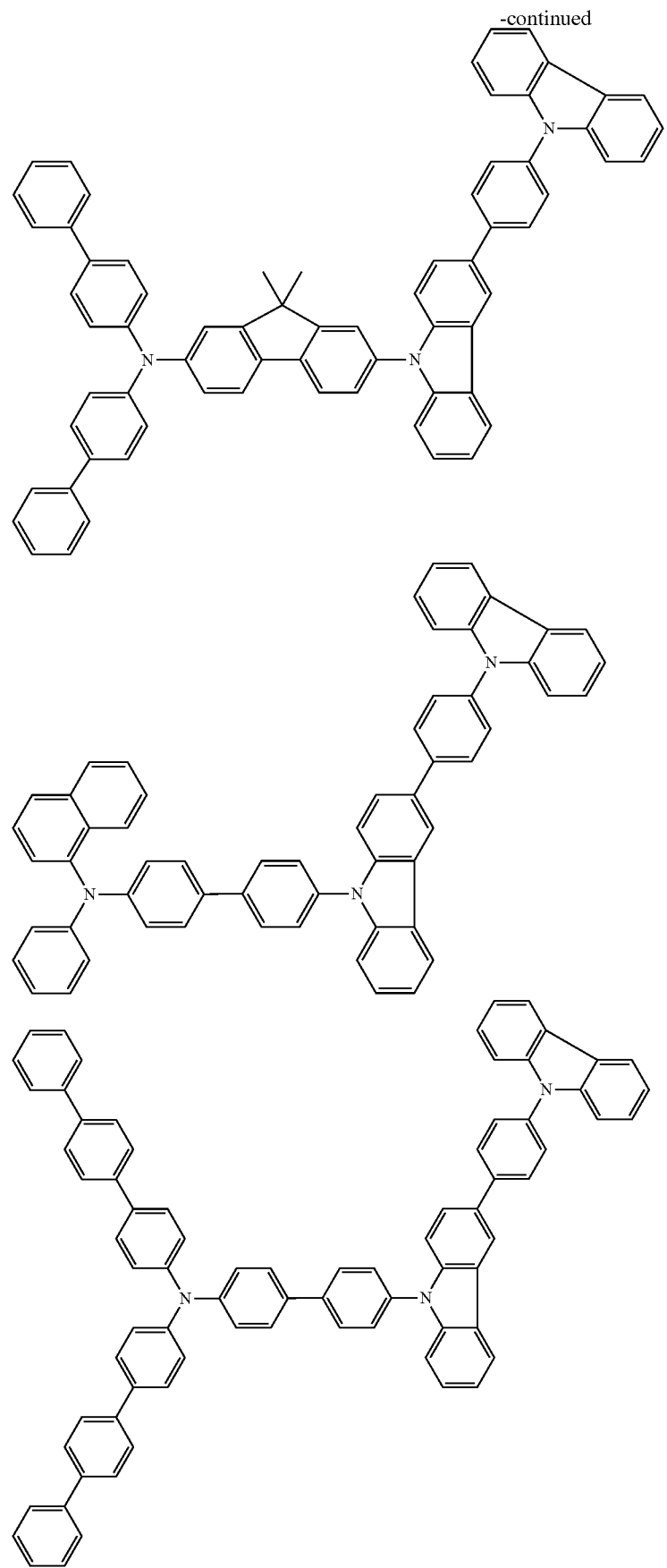

-continued
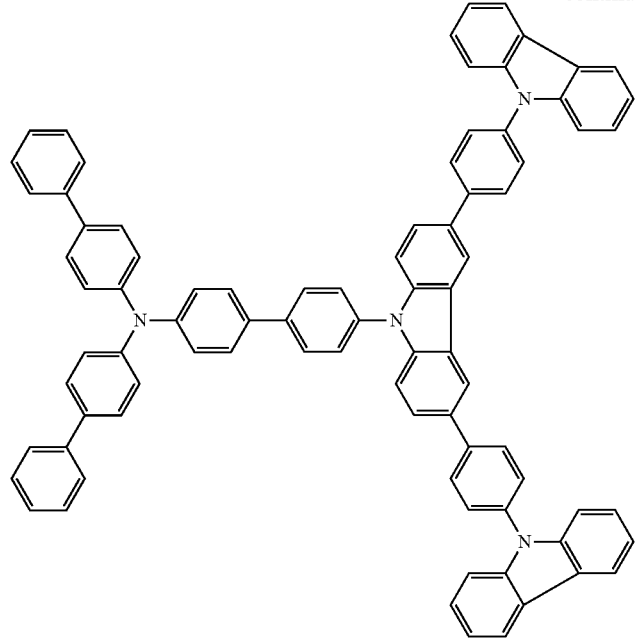
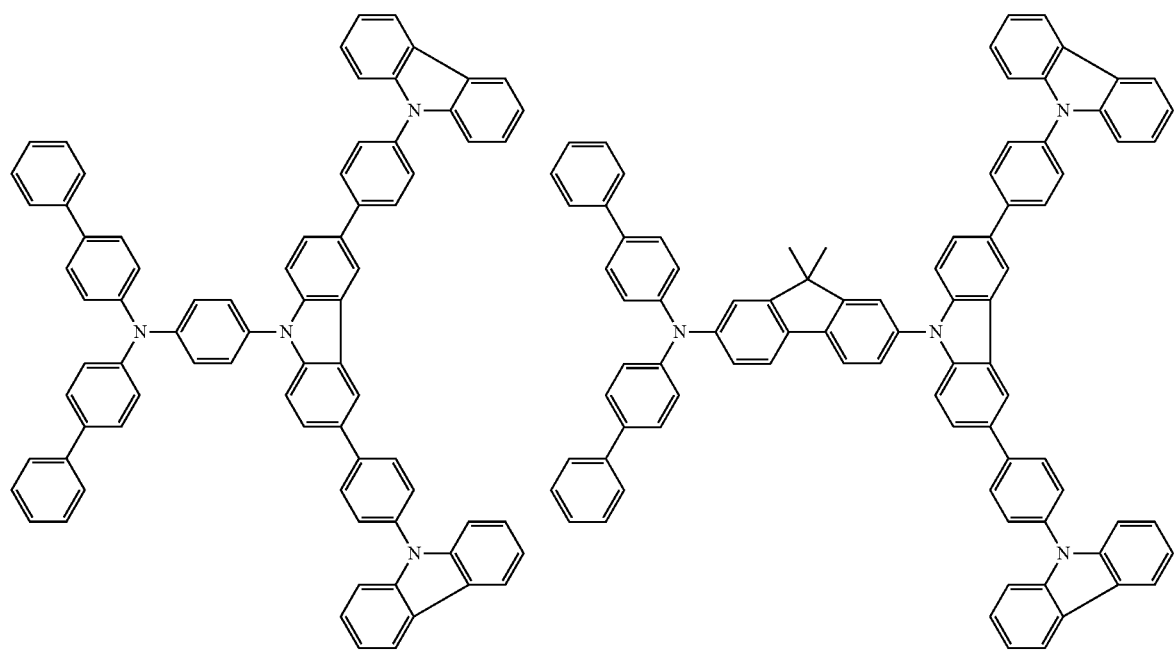

-continued
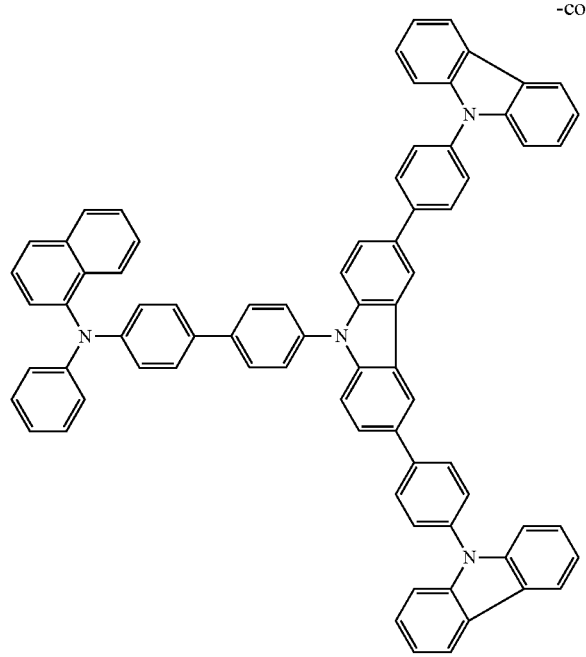
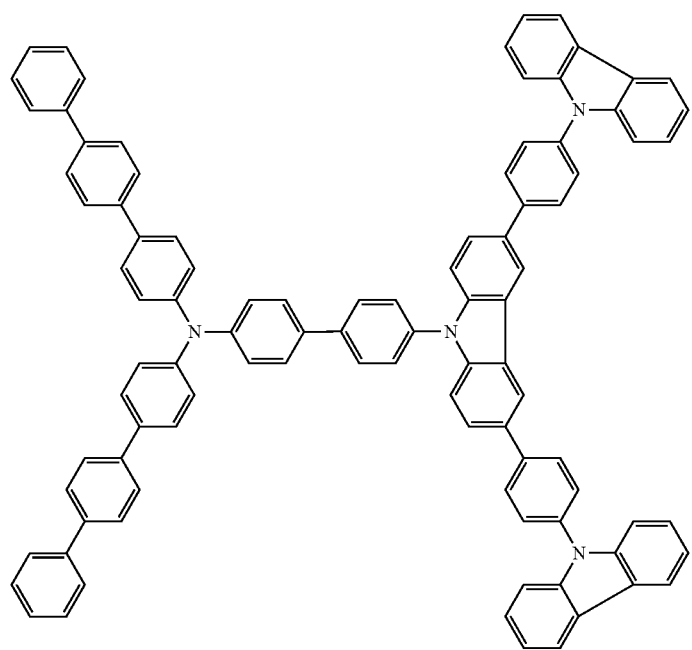

-continued
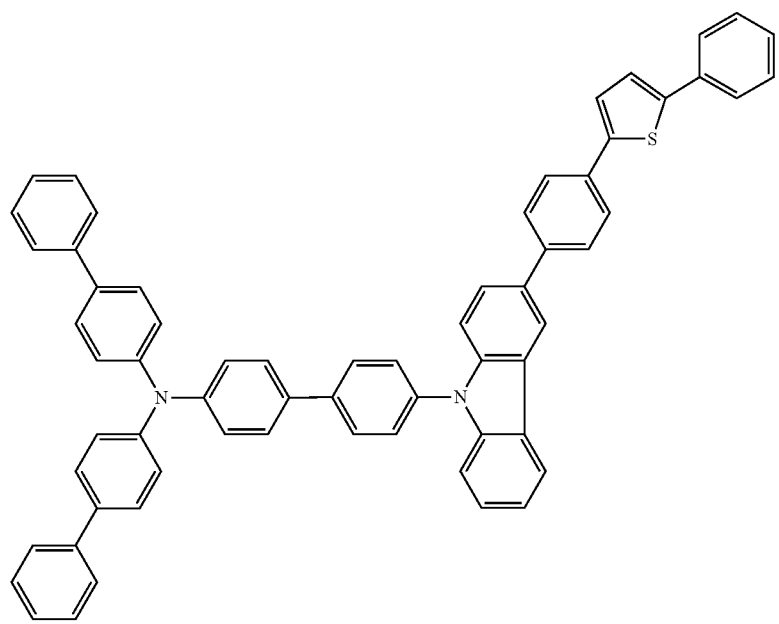
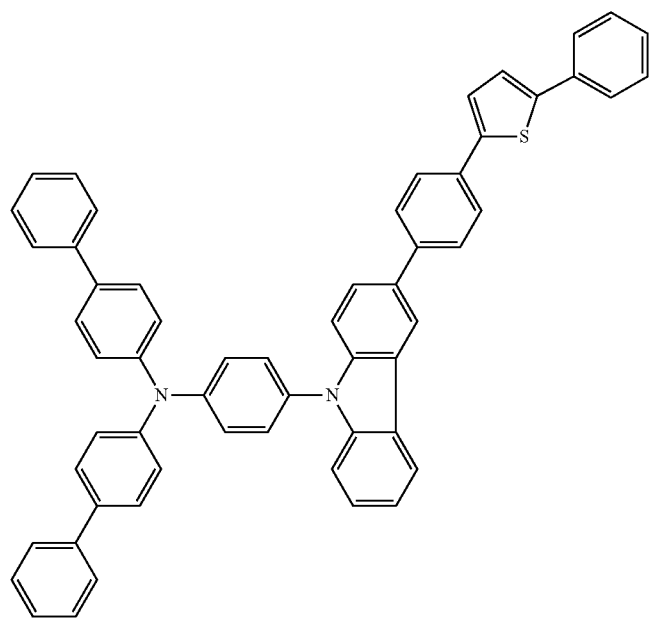

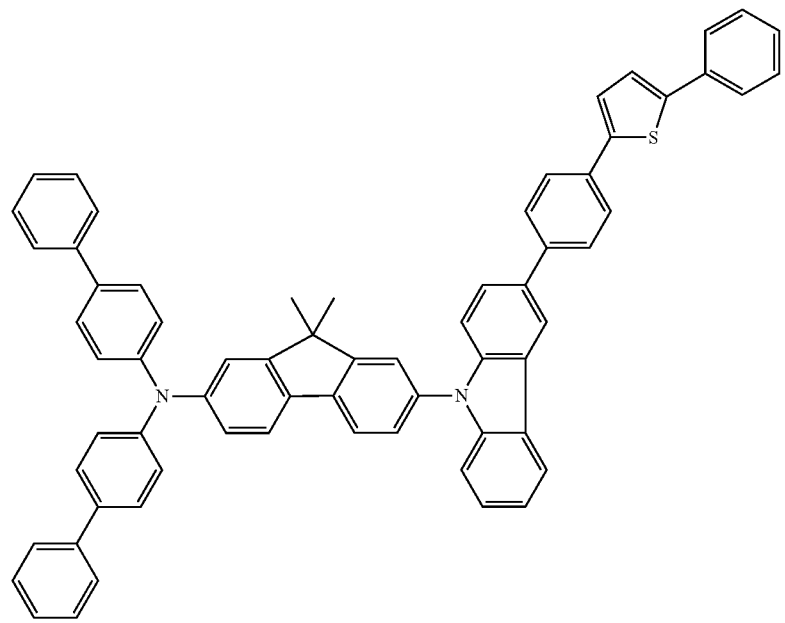
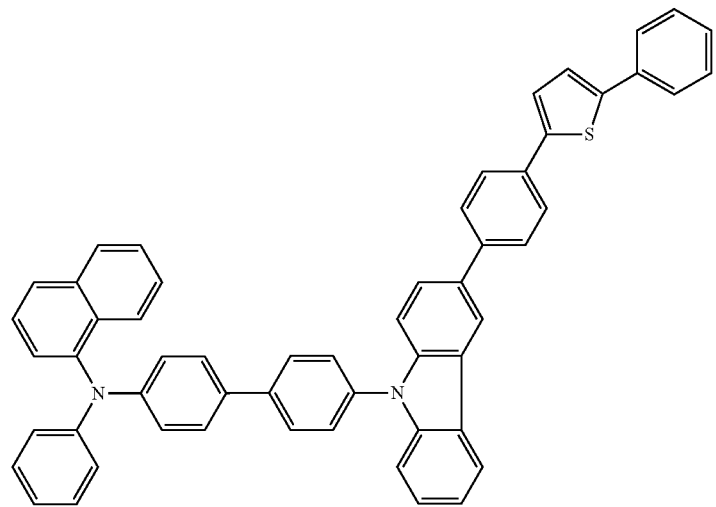

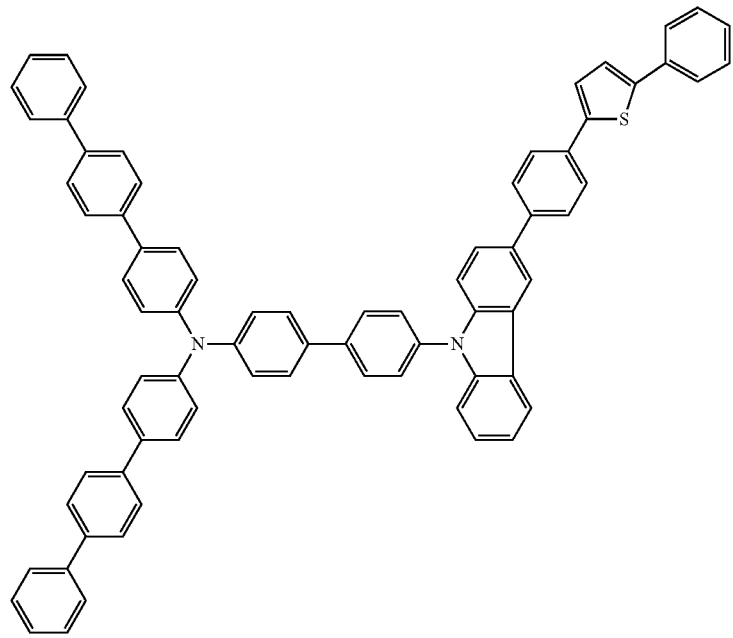
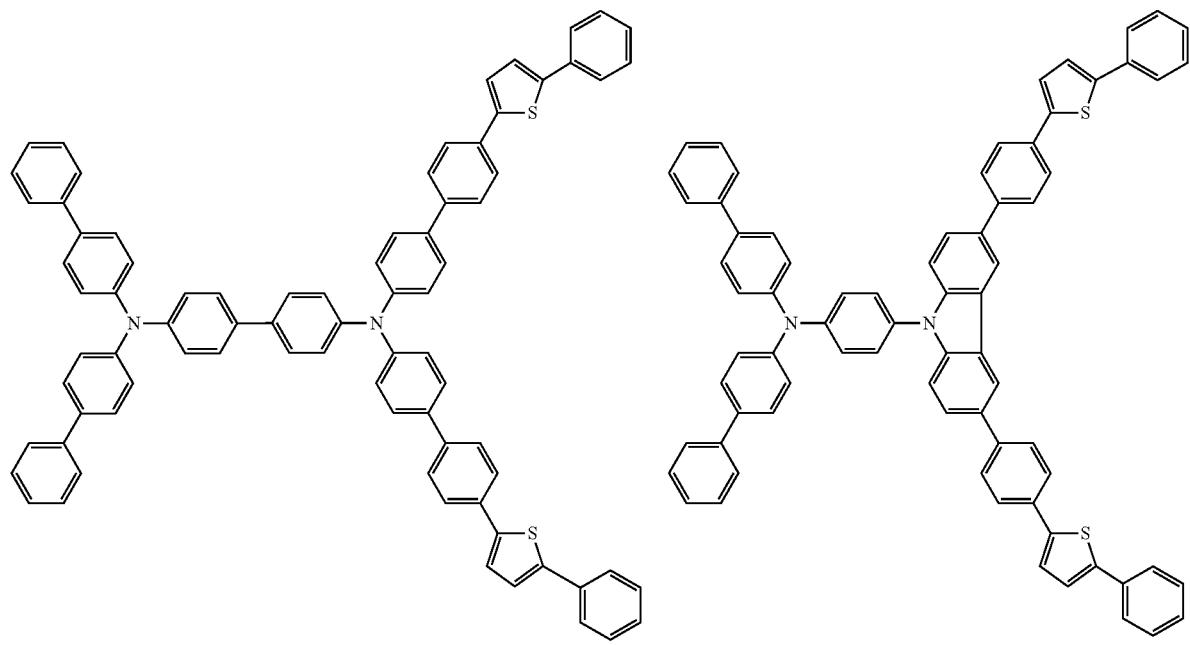

-continued
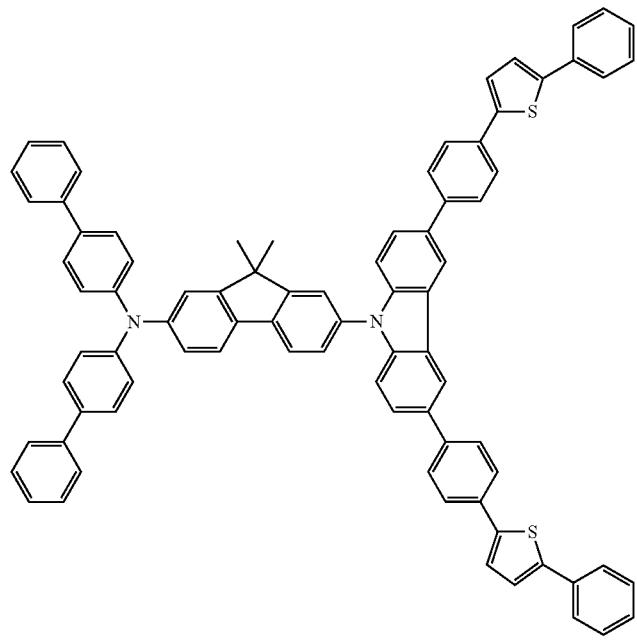
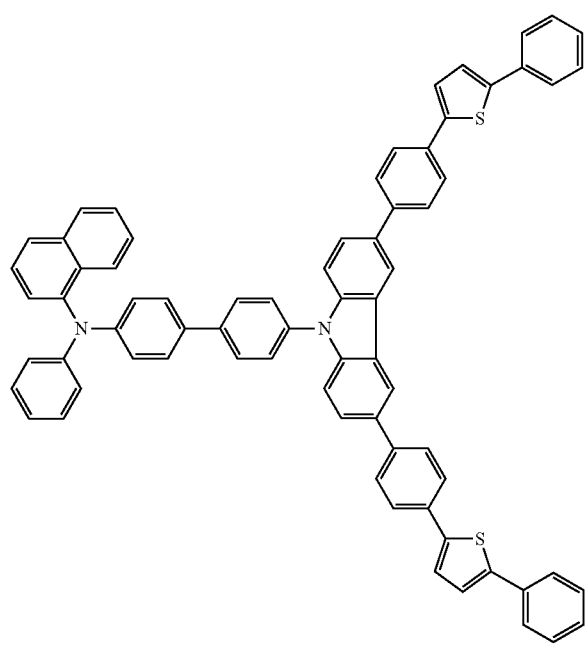

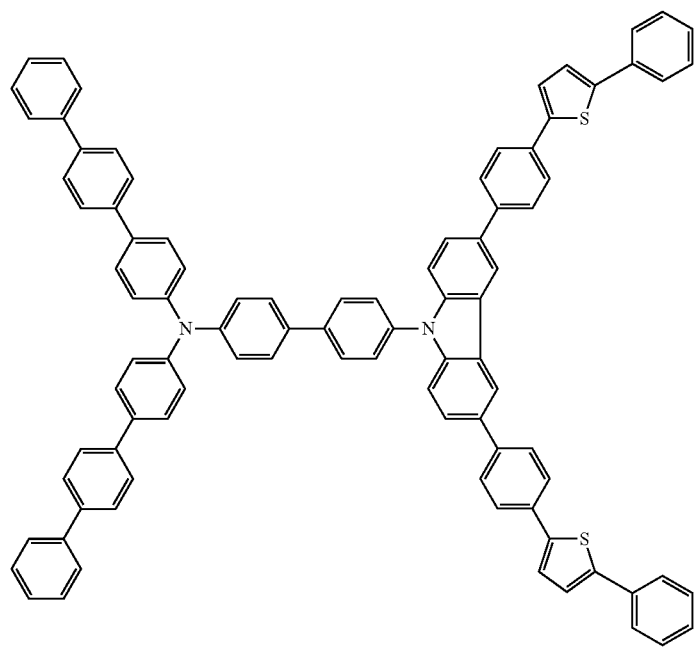
[Chem. 10]
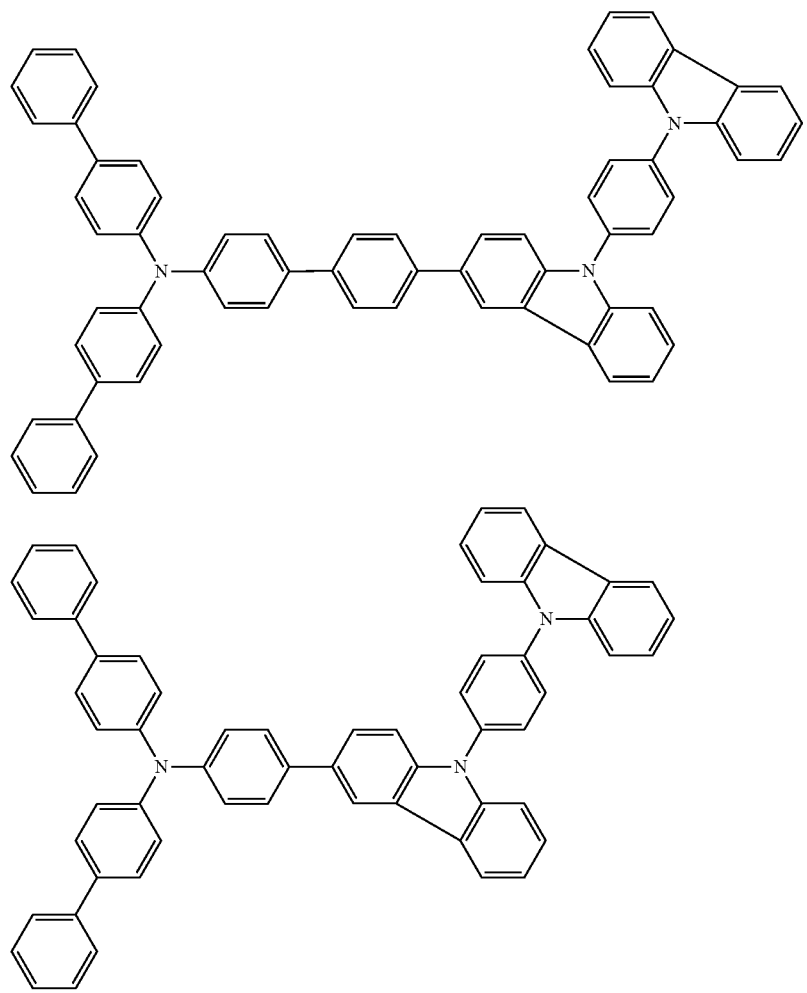

-continued
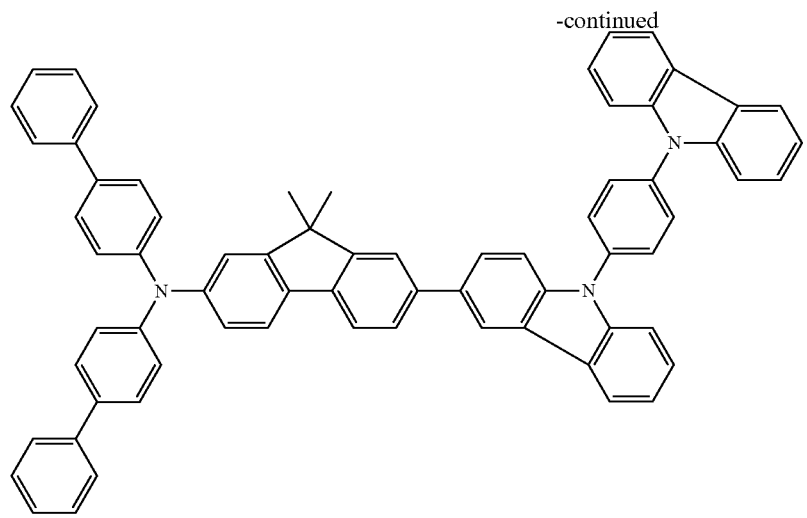
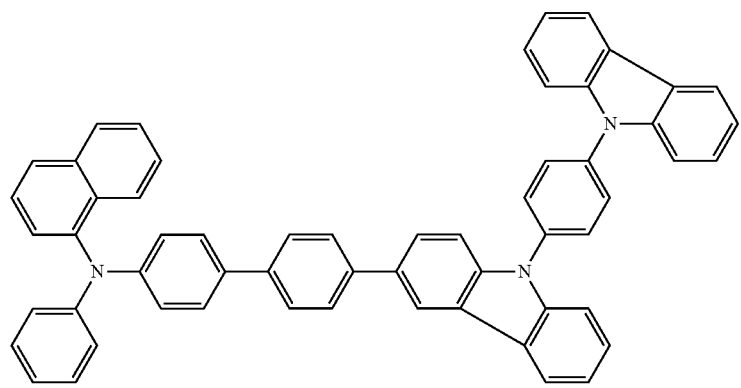
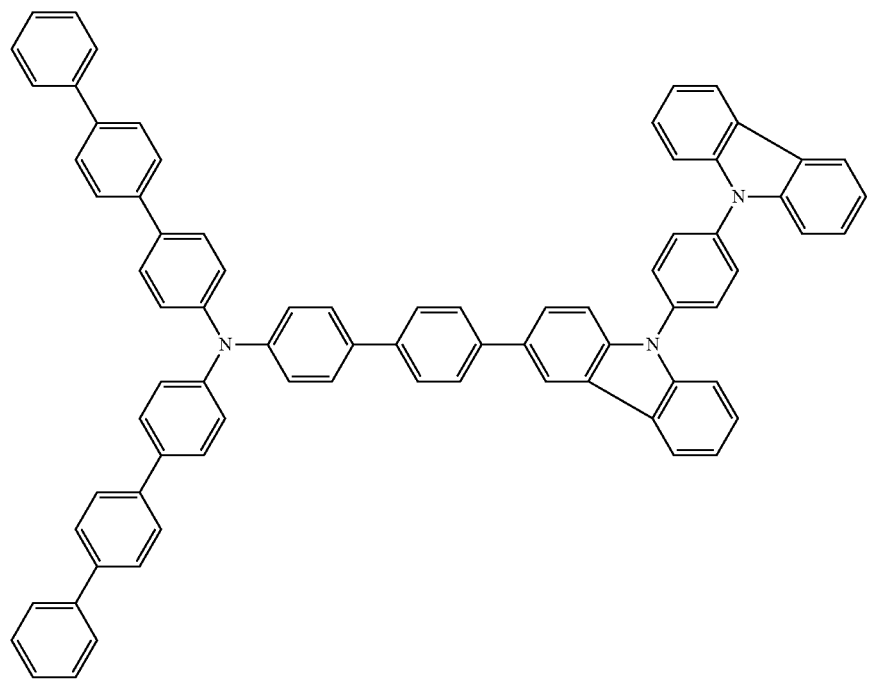

-continued
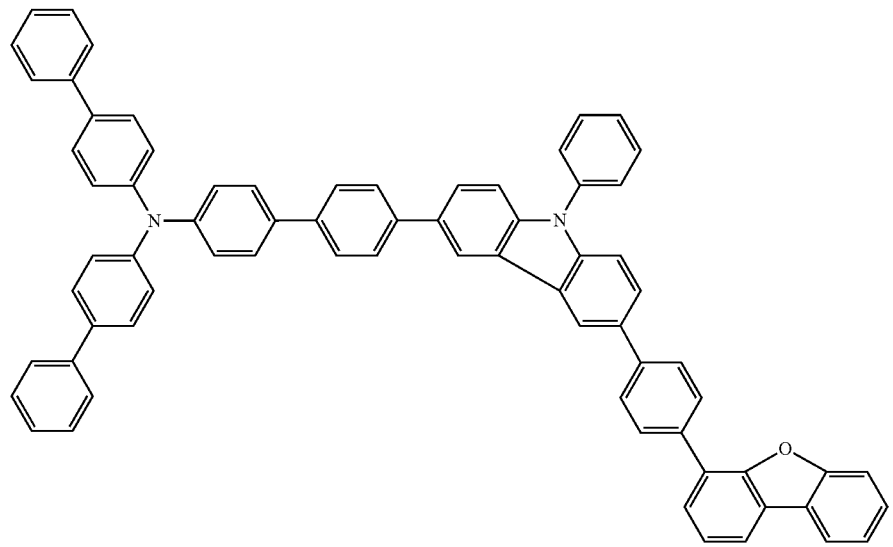
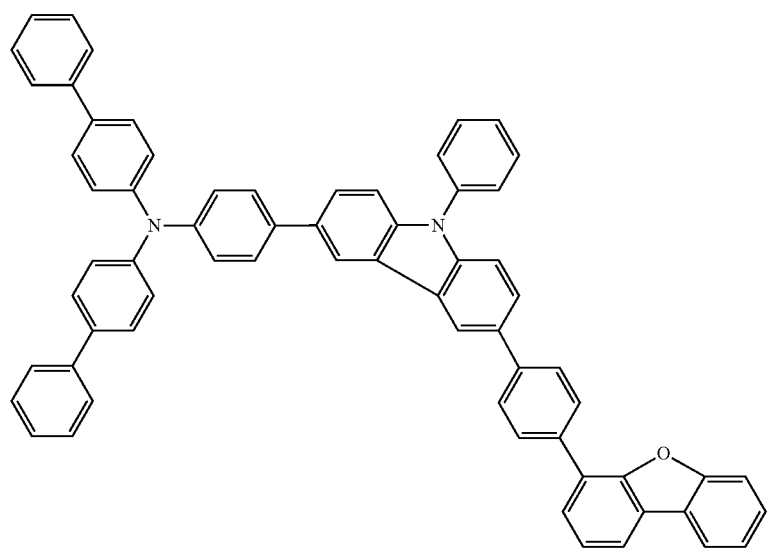
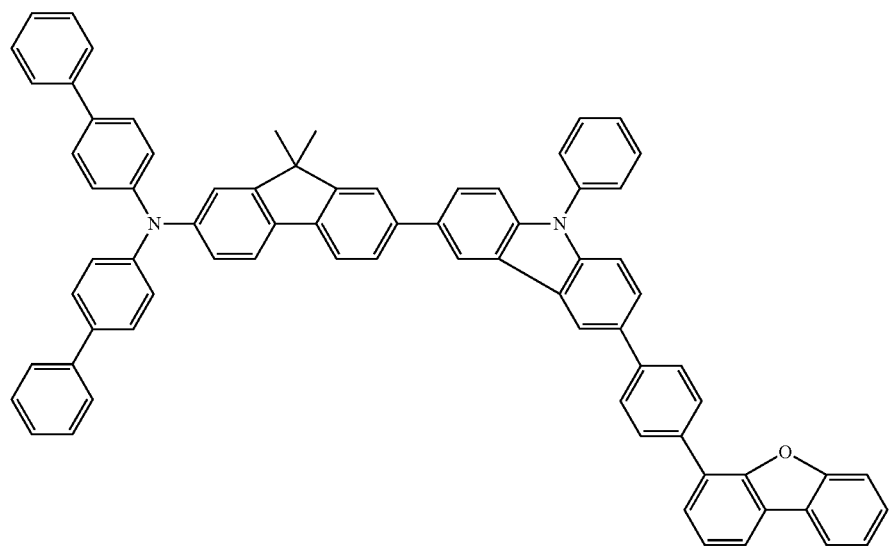

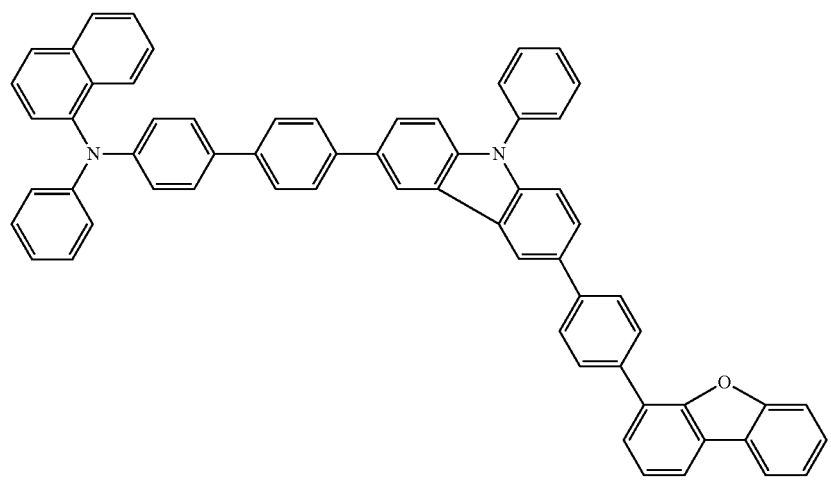
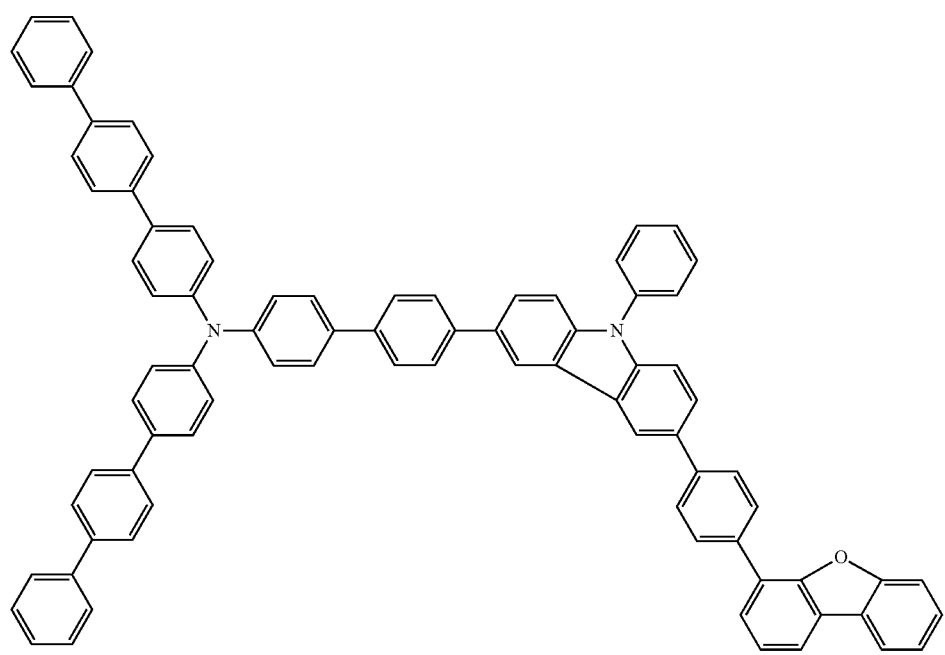

-continued
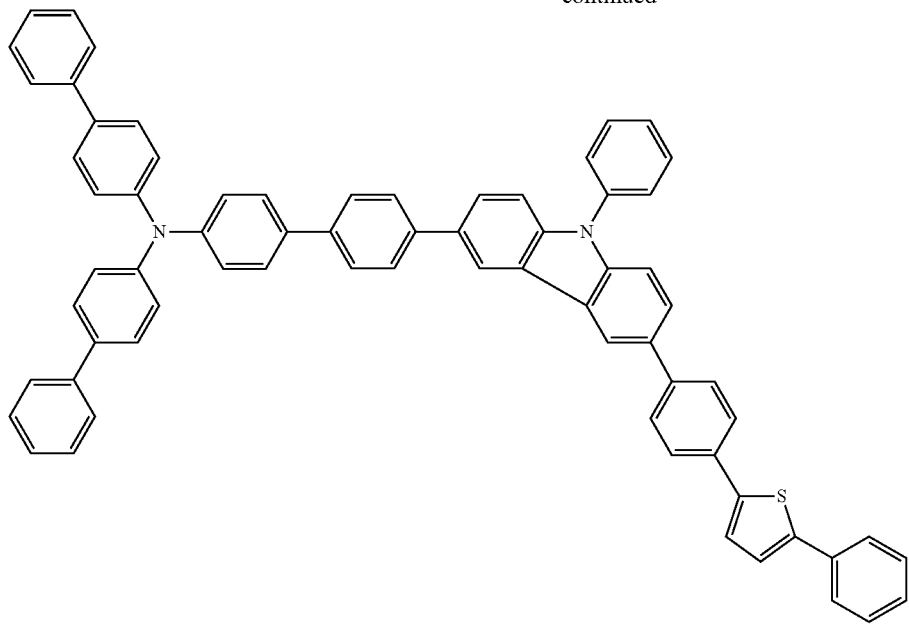
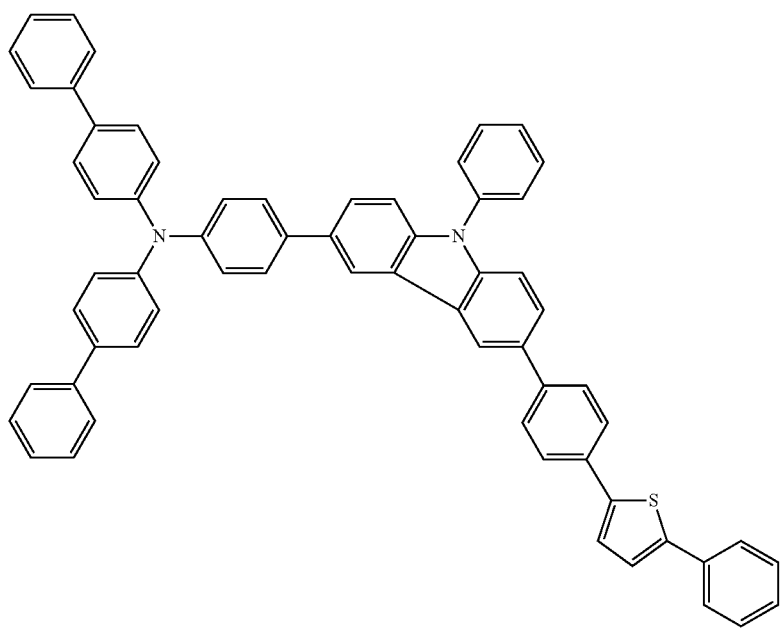

-continued
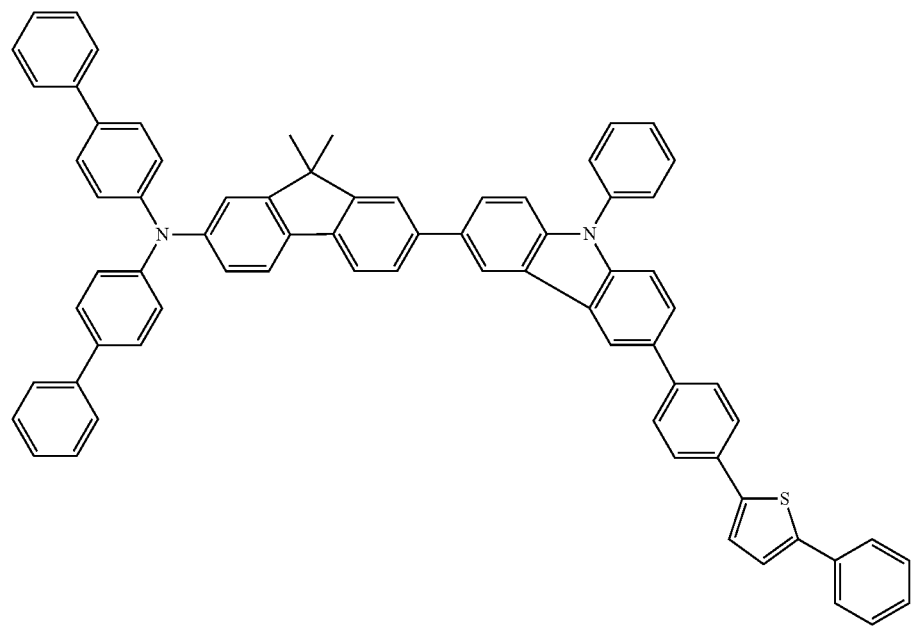
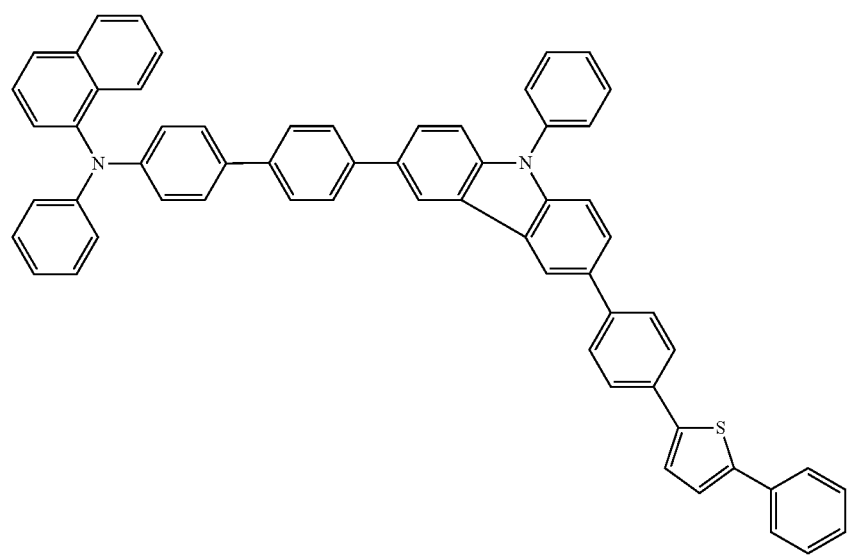

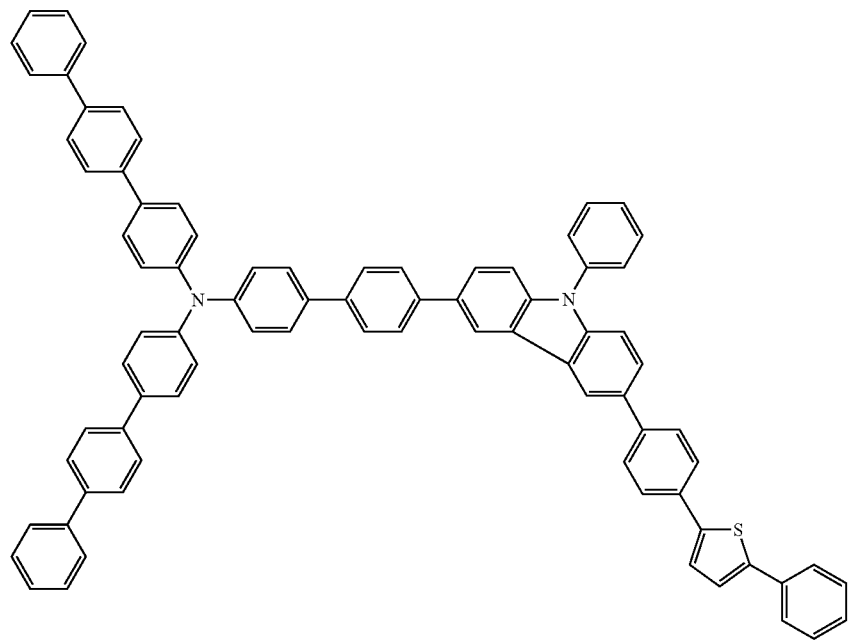
[Chem. 11]
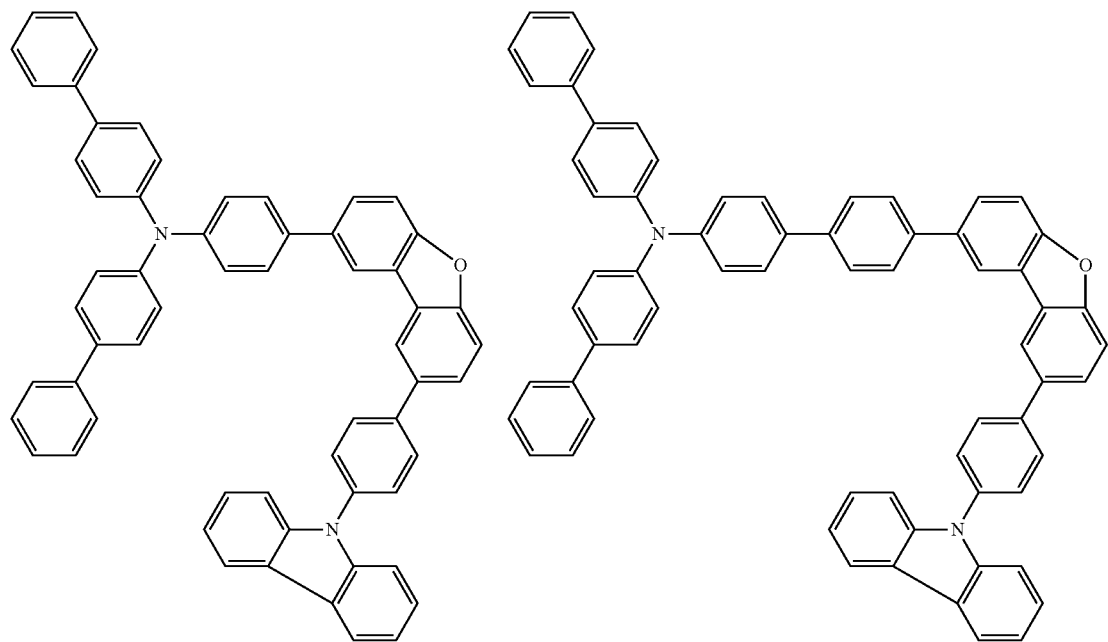

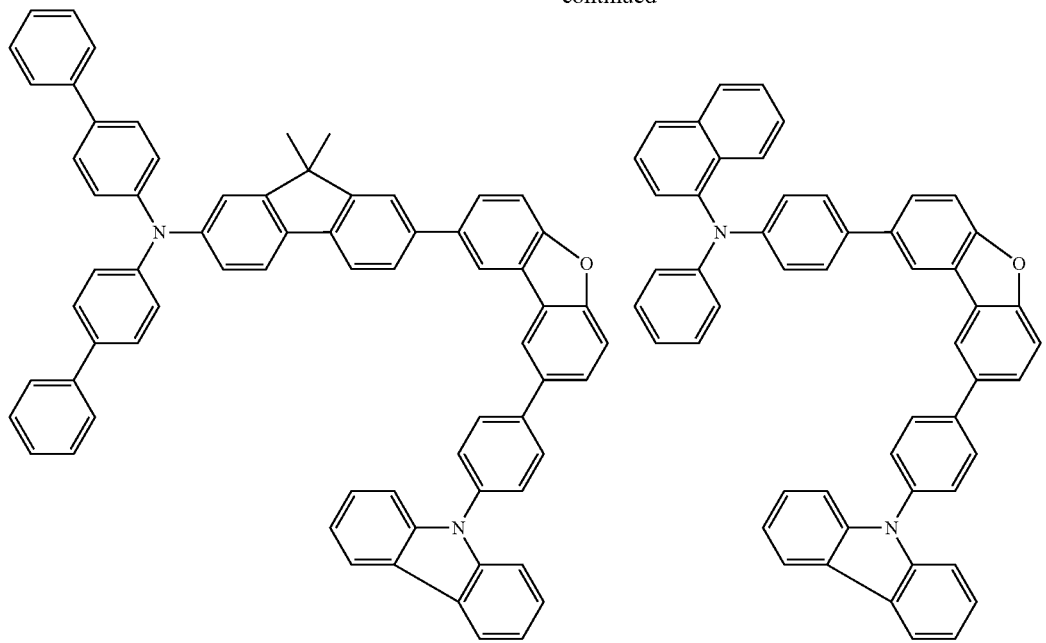
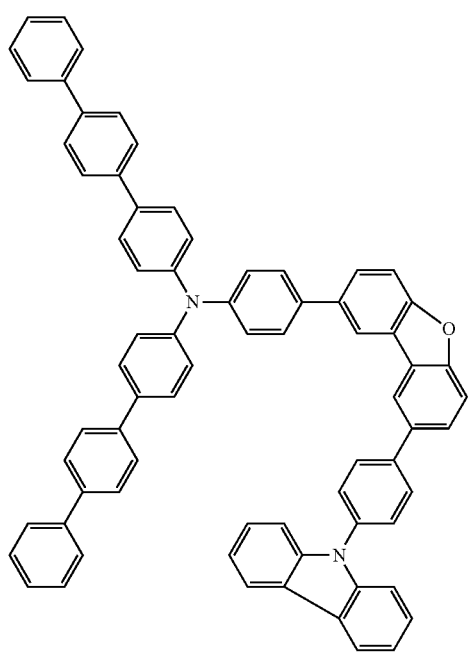

-continued
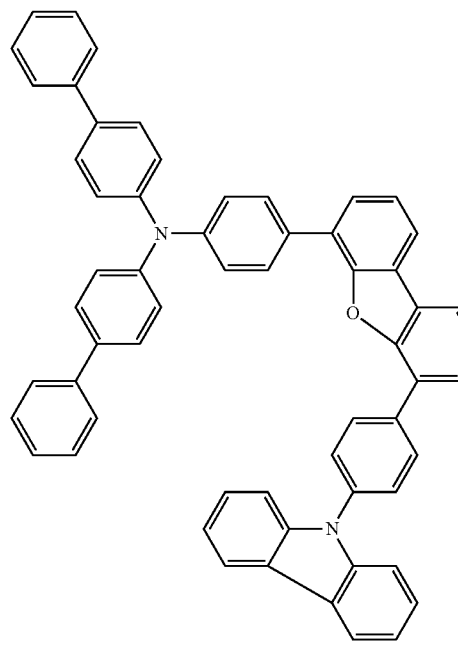
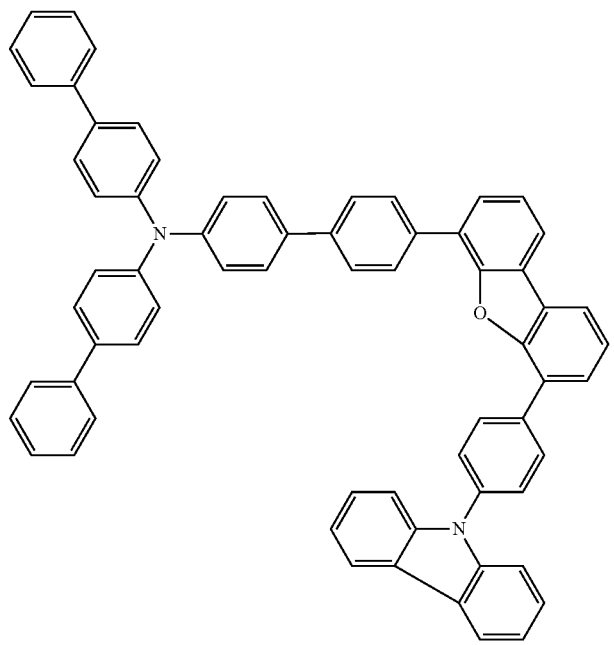
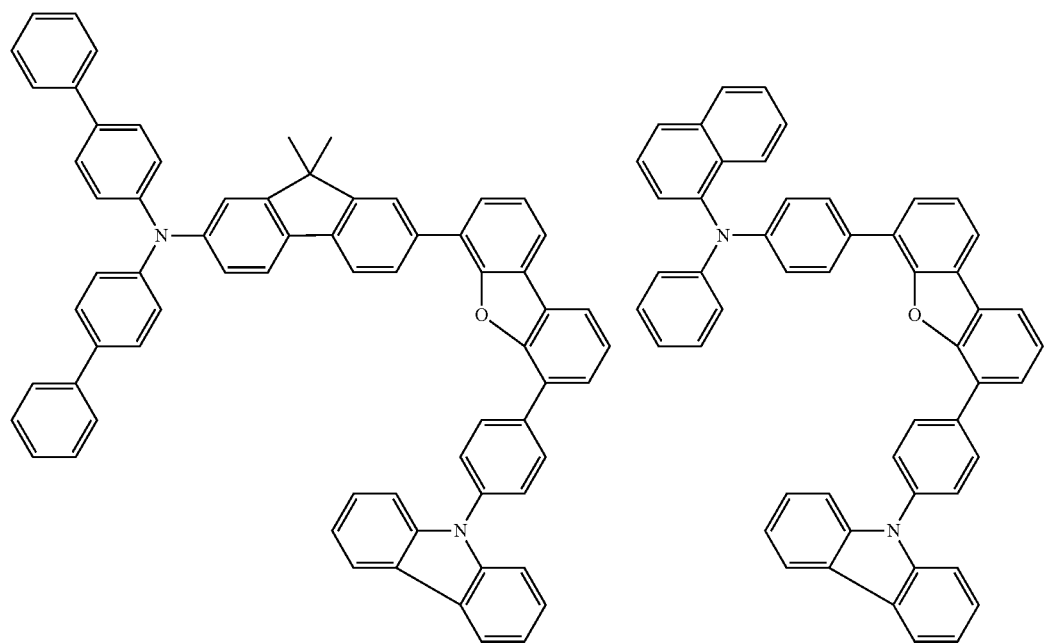

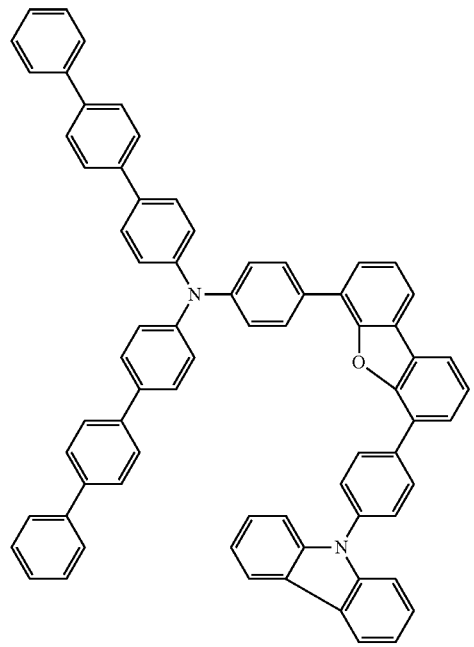
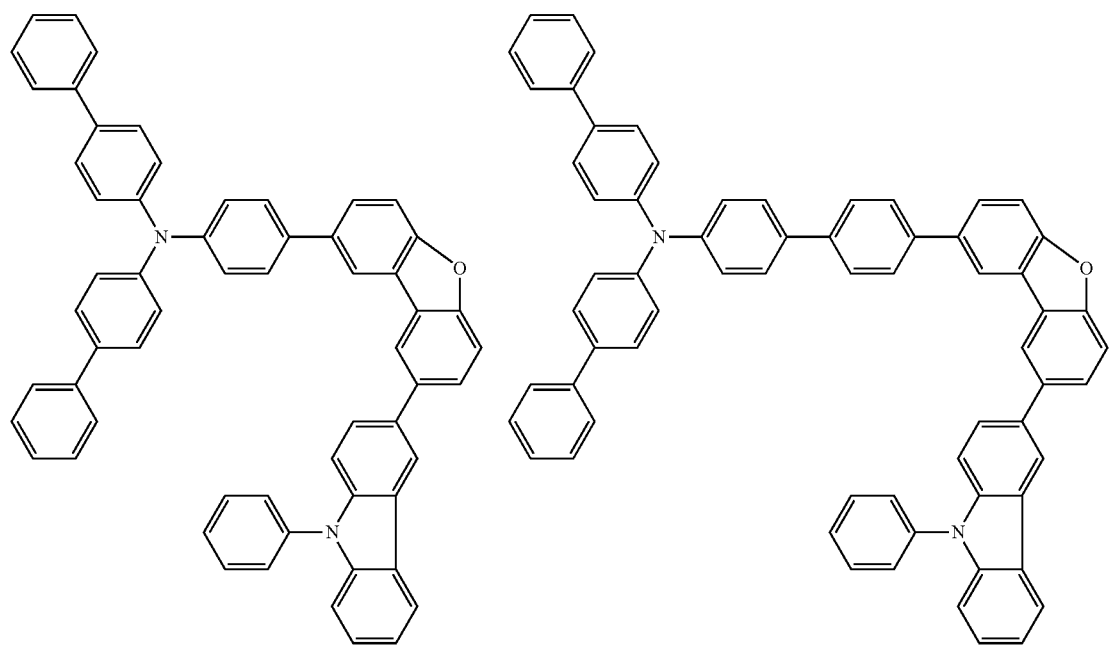

-continued
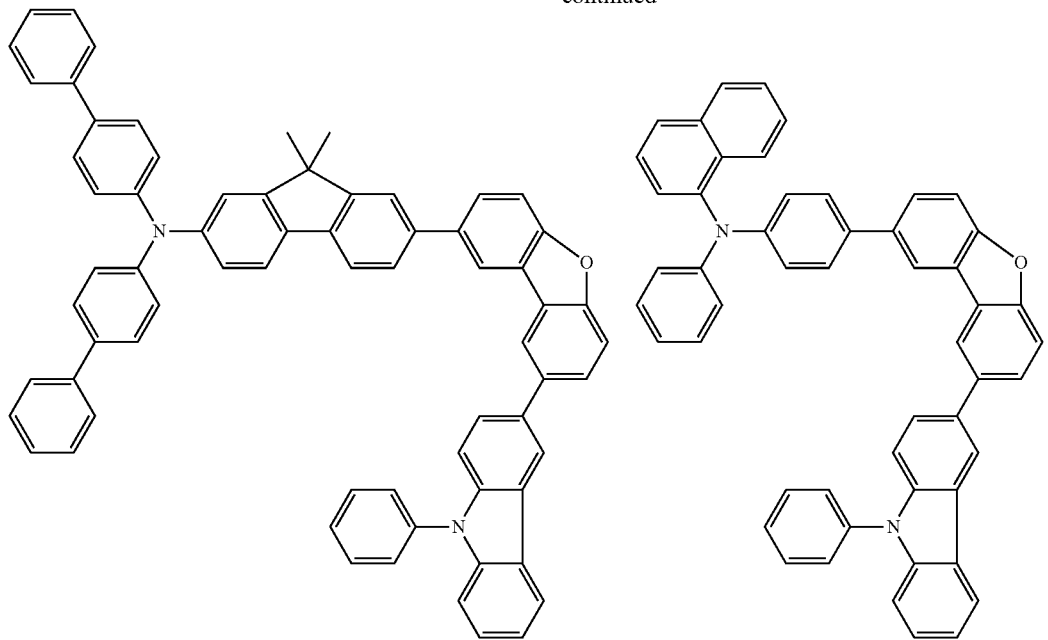
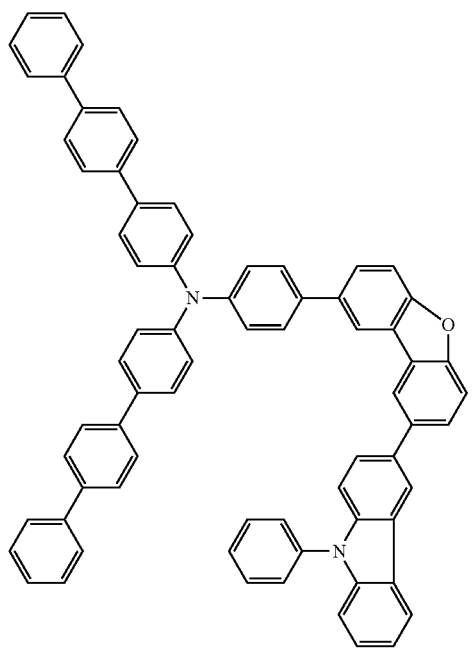

95
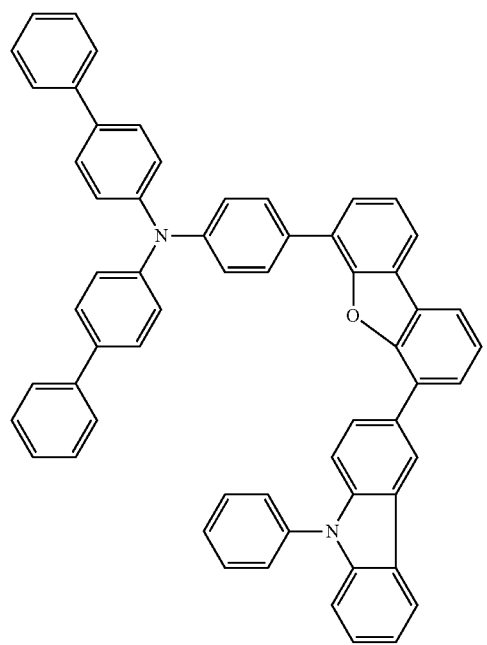
96
-continued
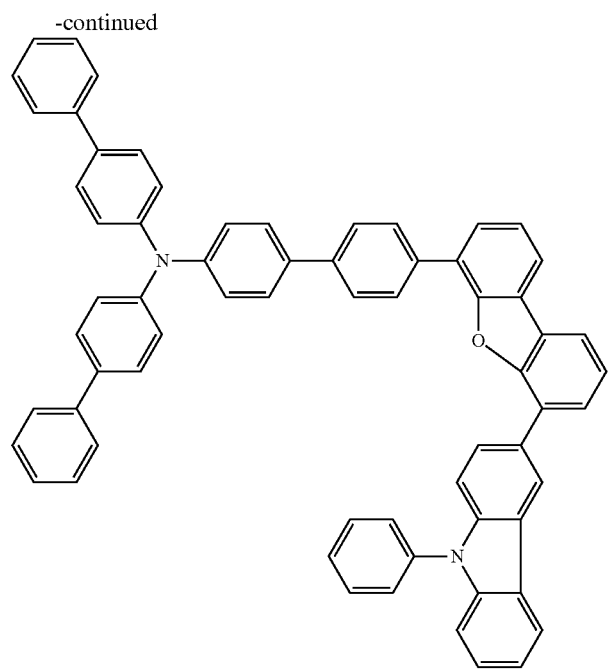
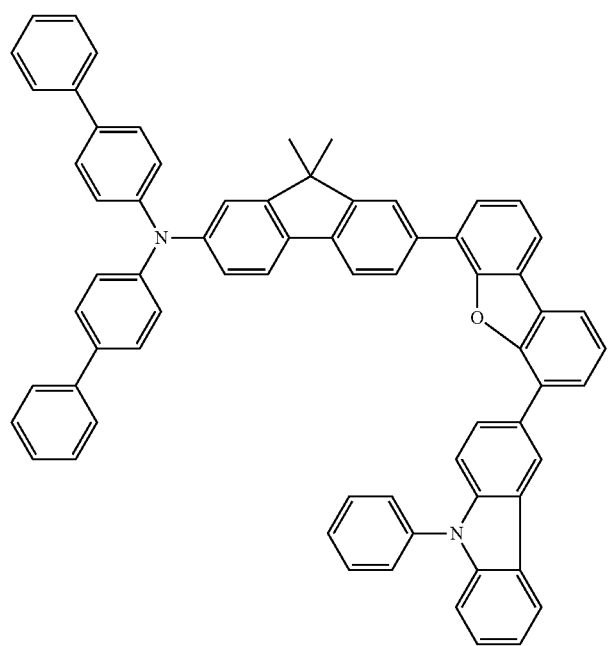
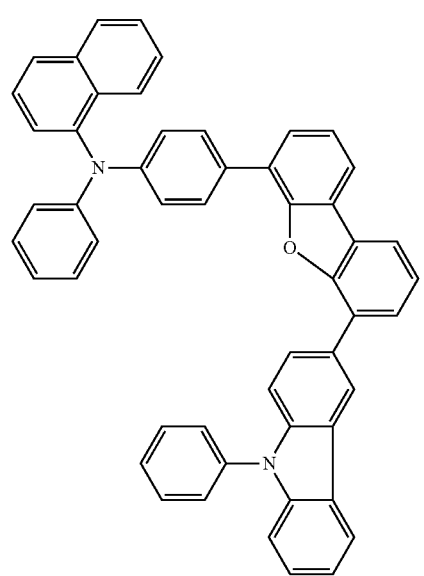

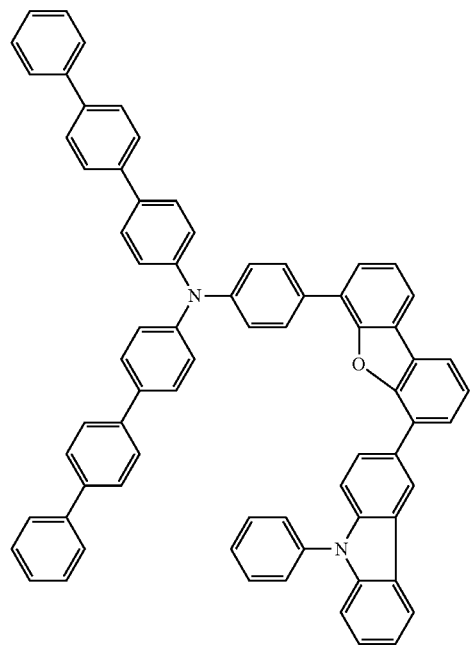
[Chem. 12]
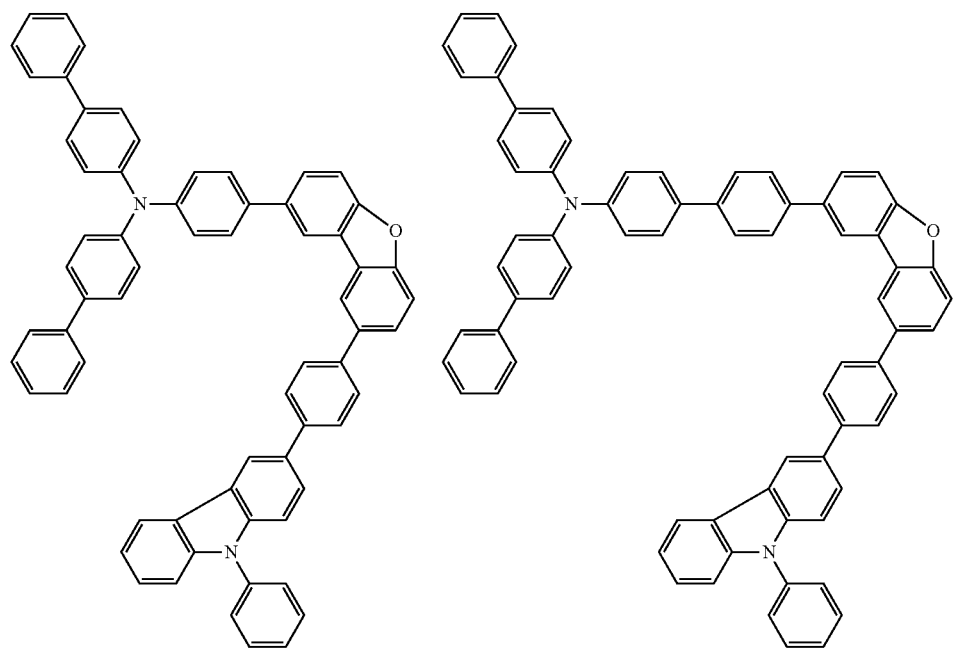

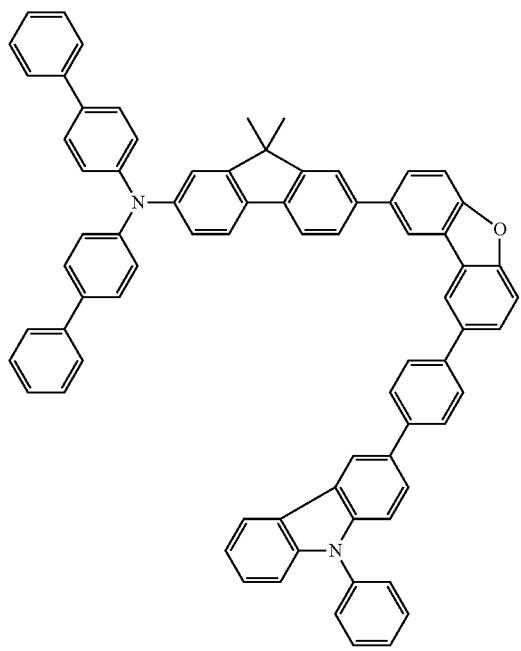
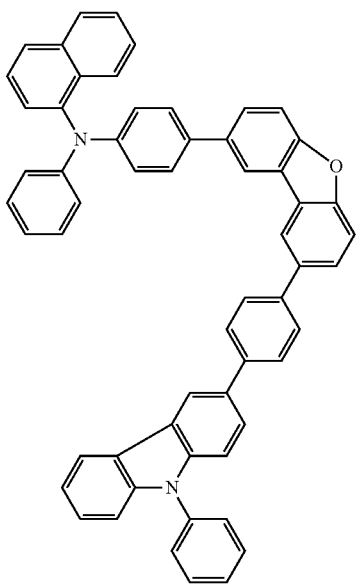
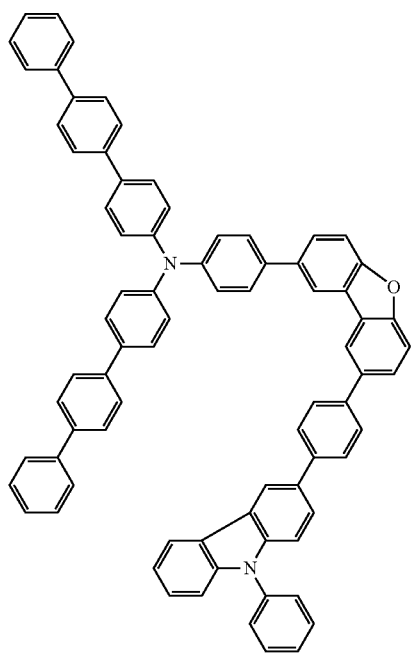

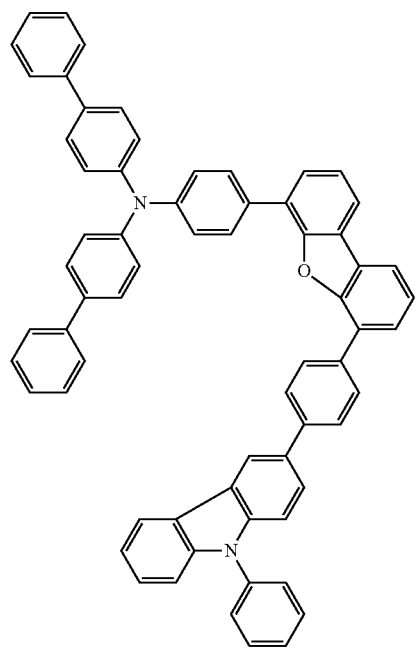
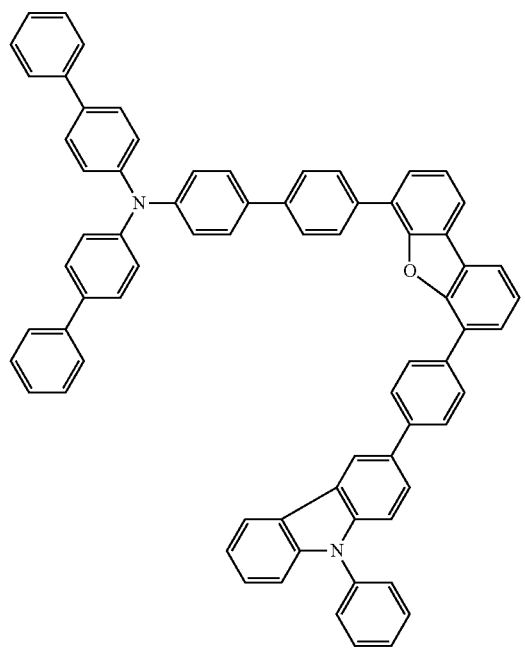
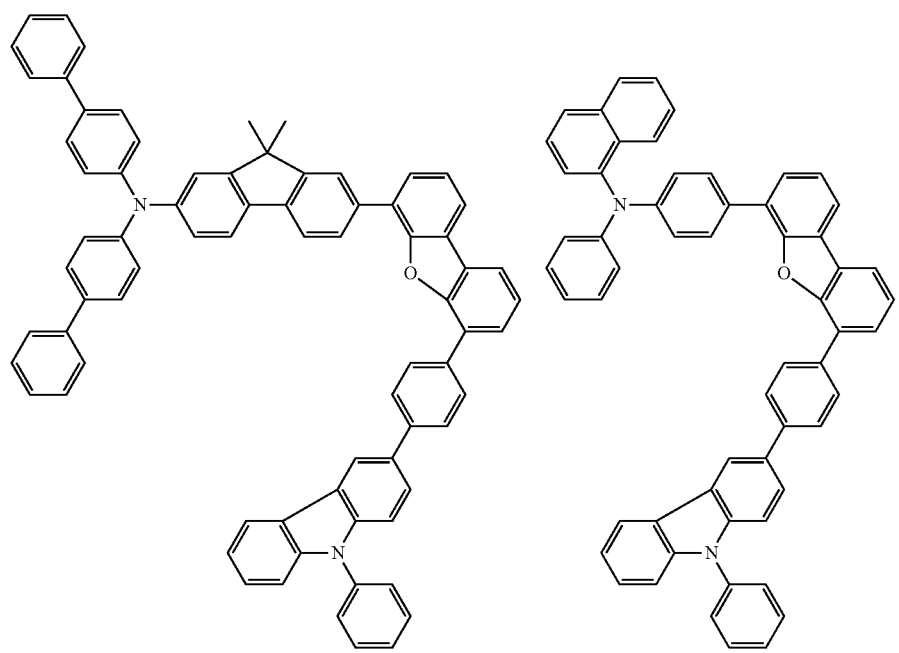

-continued
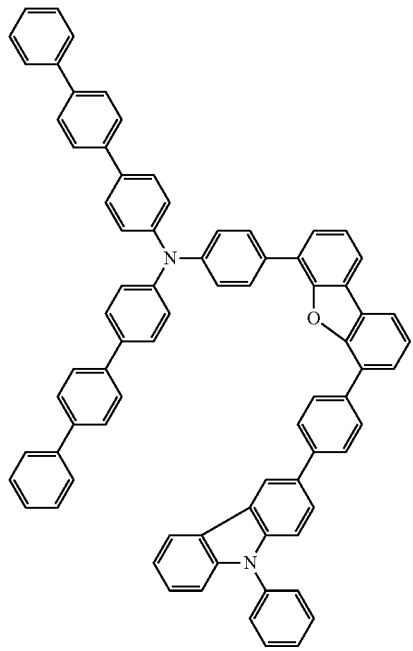

-continued
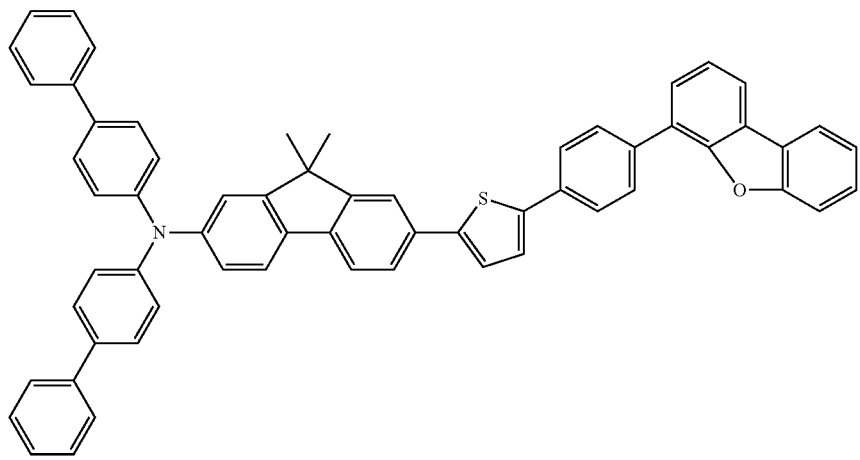
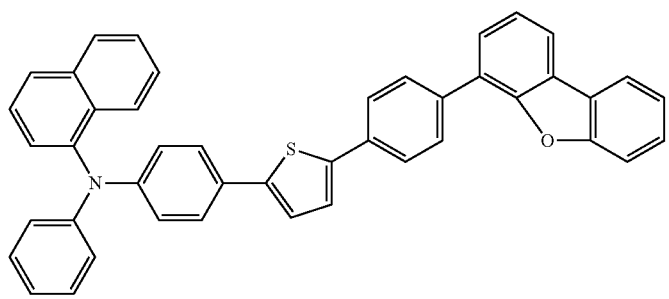
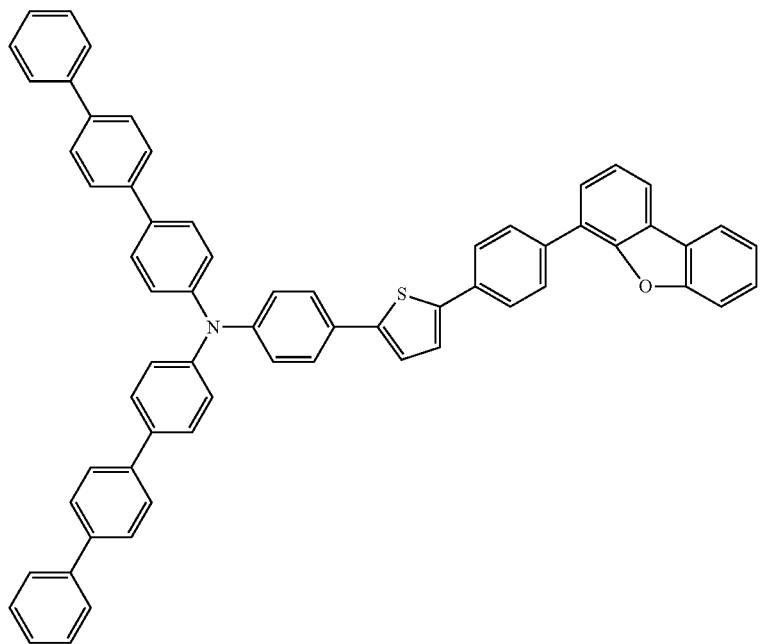

-continued
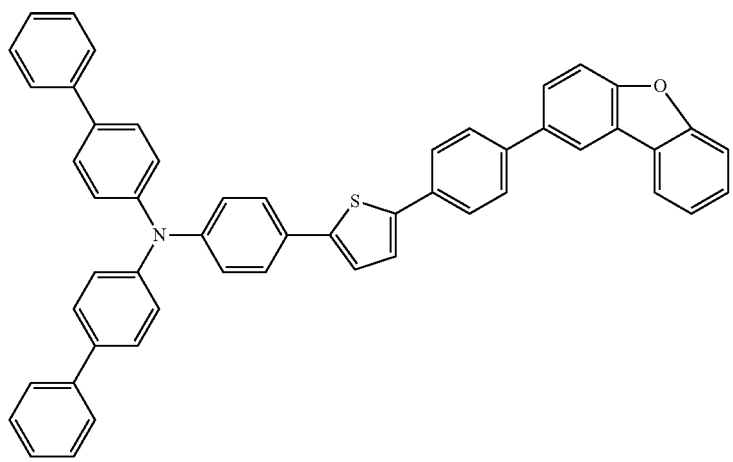
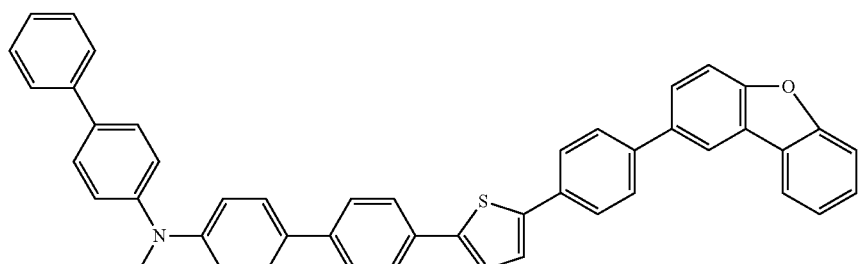
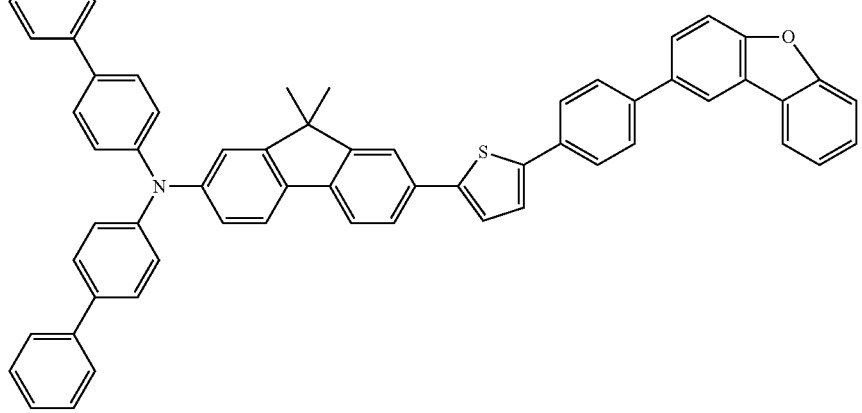
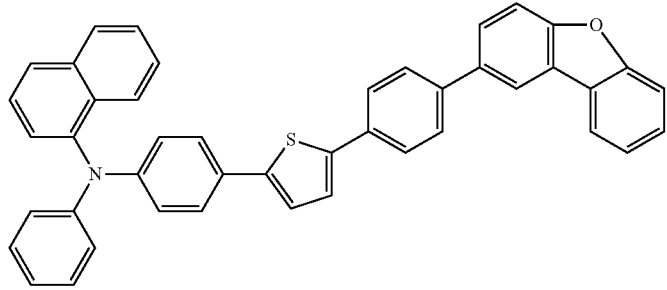

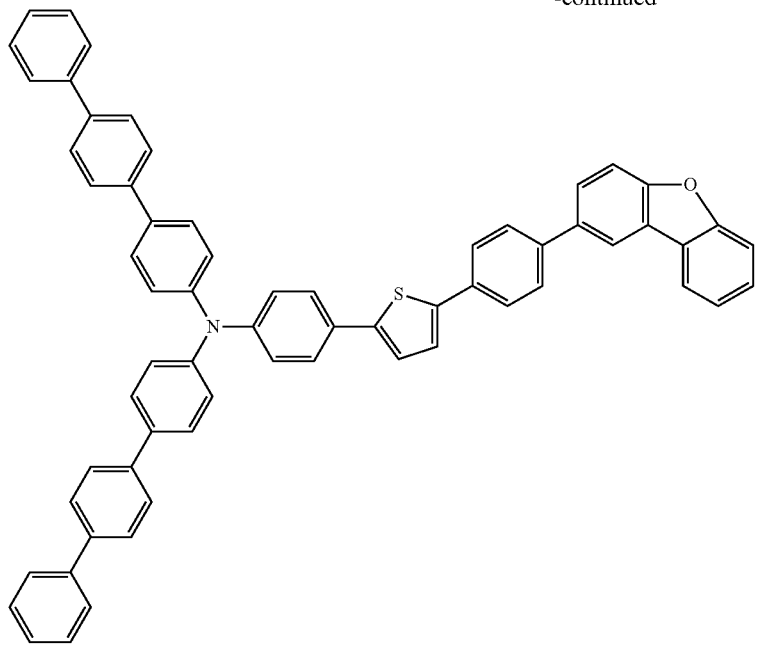
[Chem. 13]
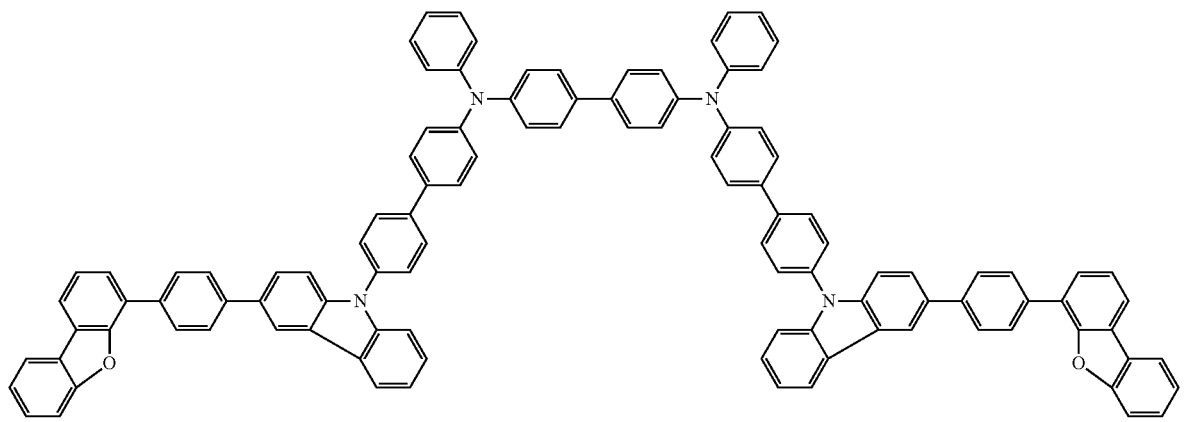
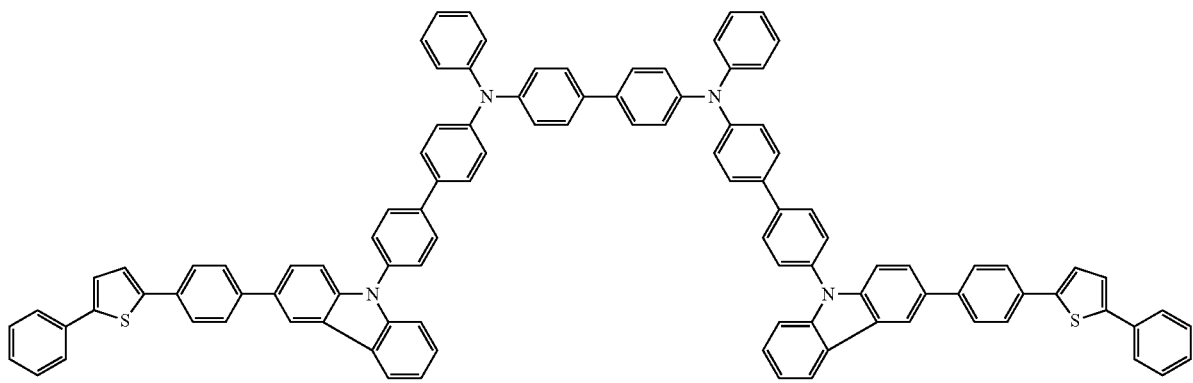

-continued
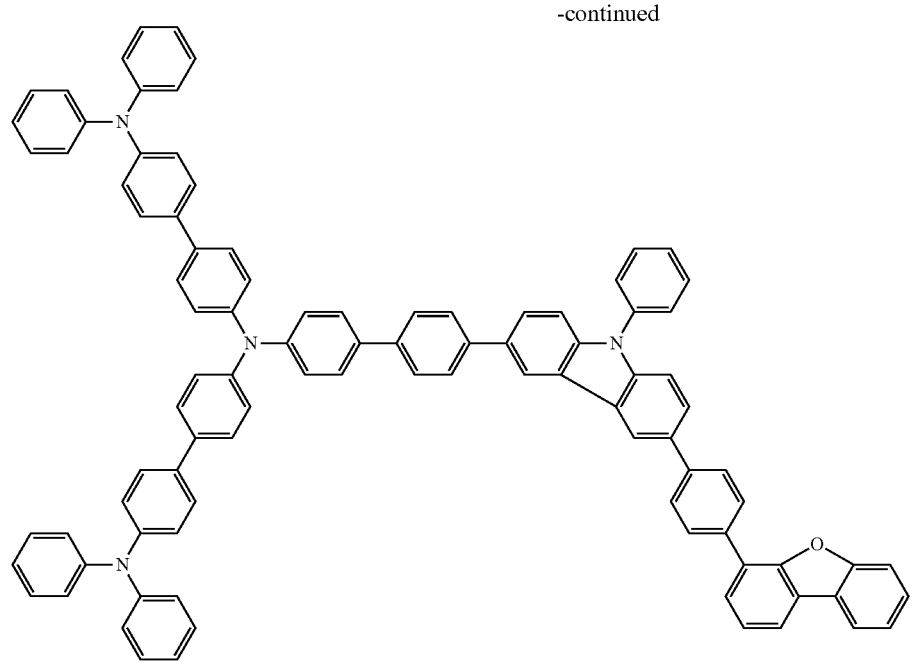
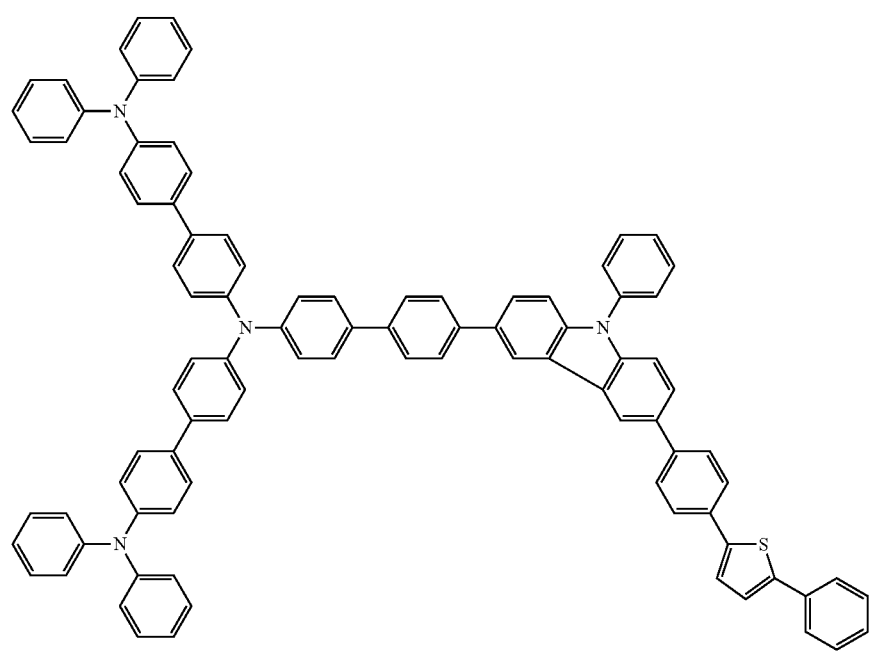

-continued
113
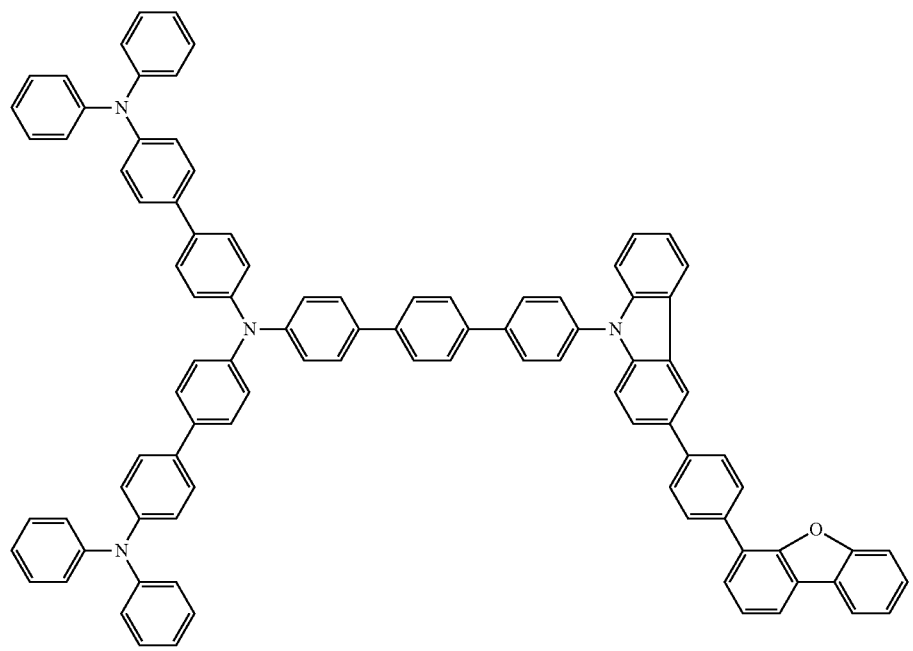
114
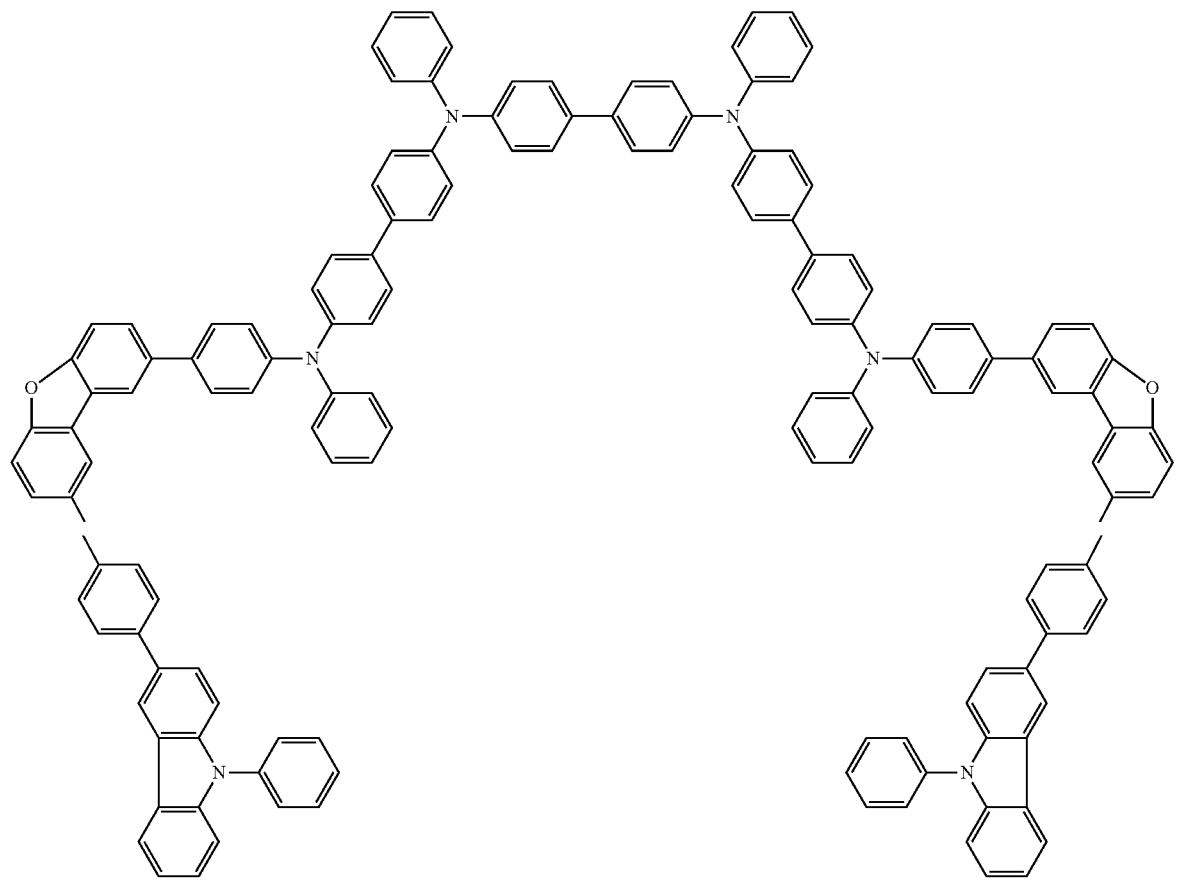

-continued
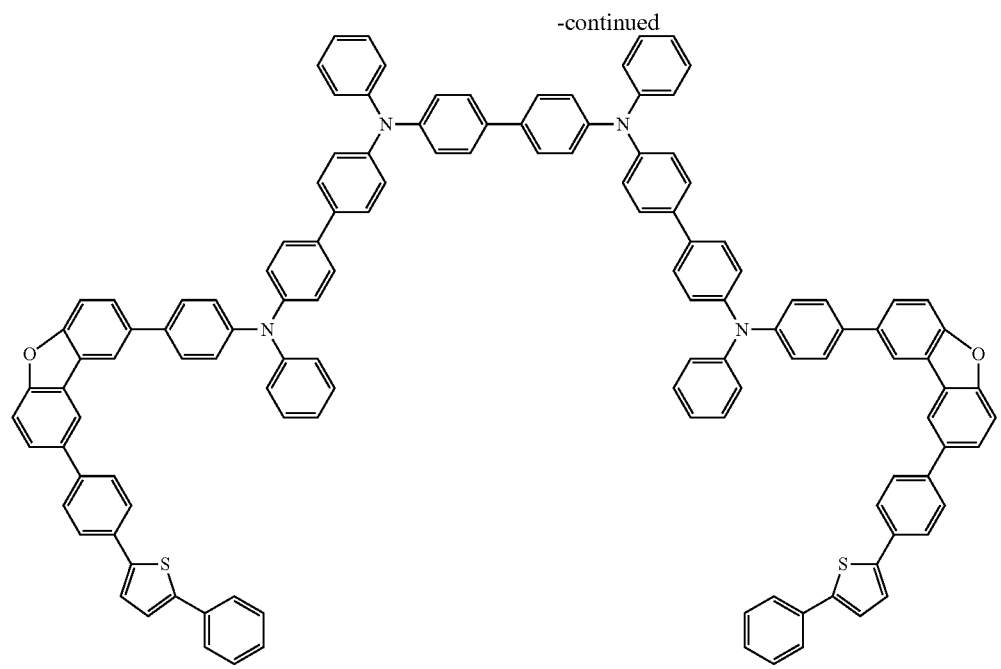
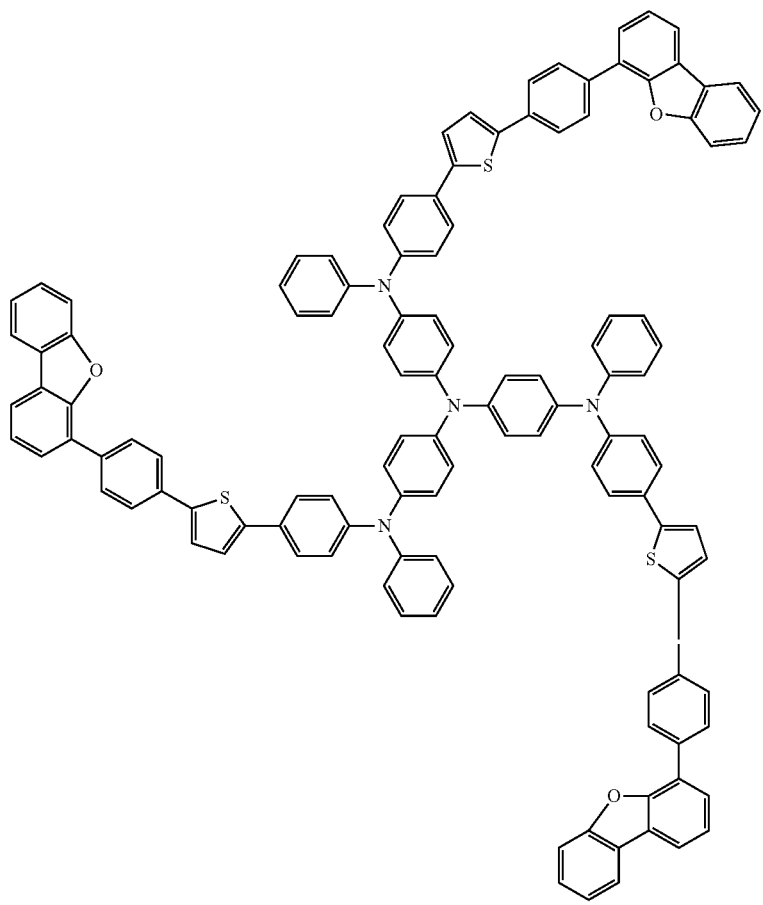

-continued
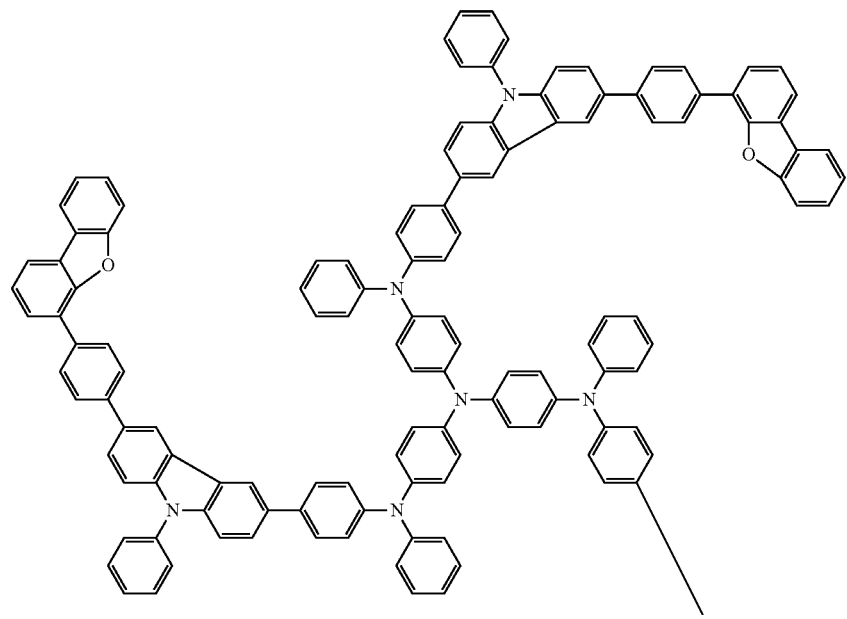
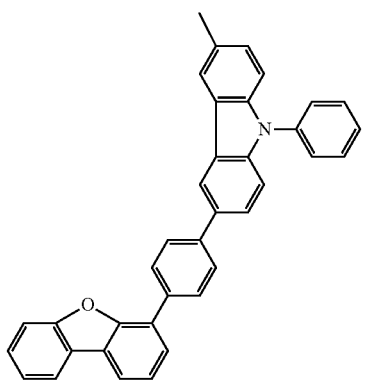
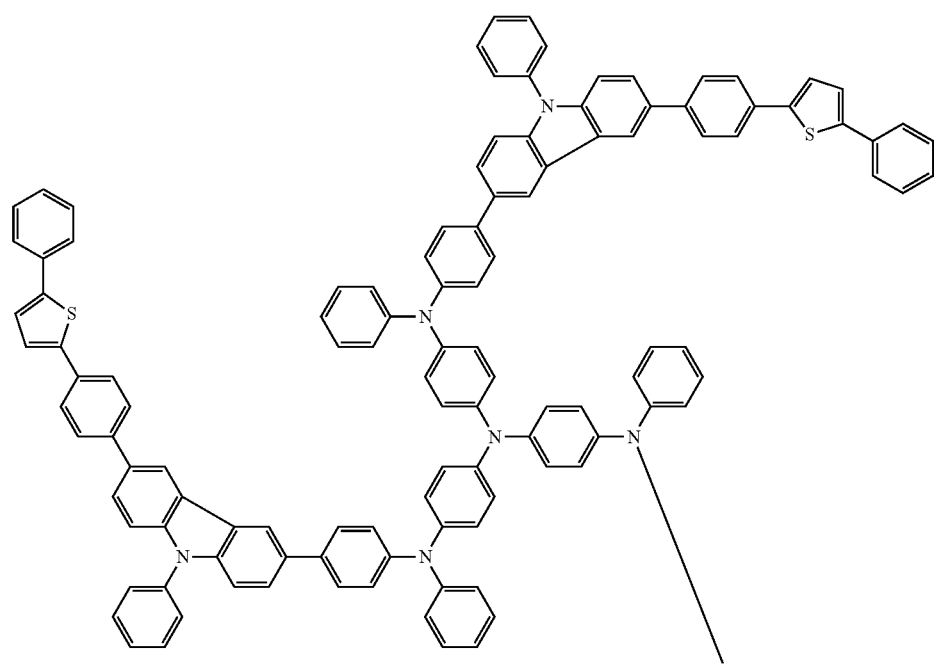

-continued
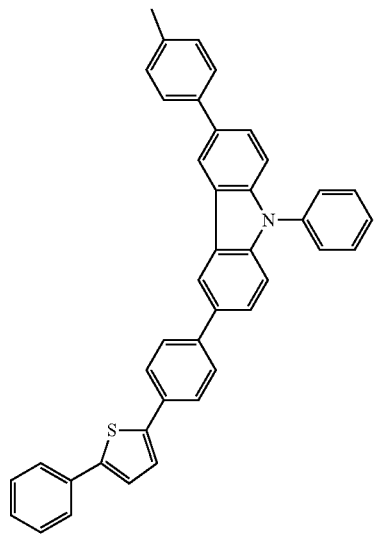
[Chem. 14]
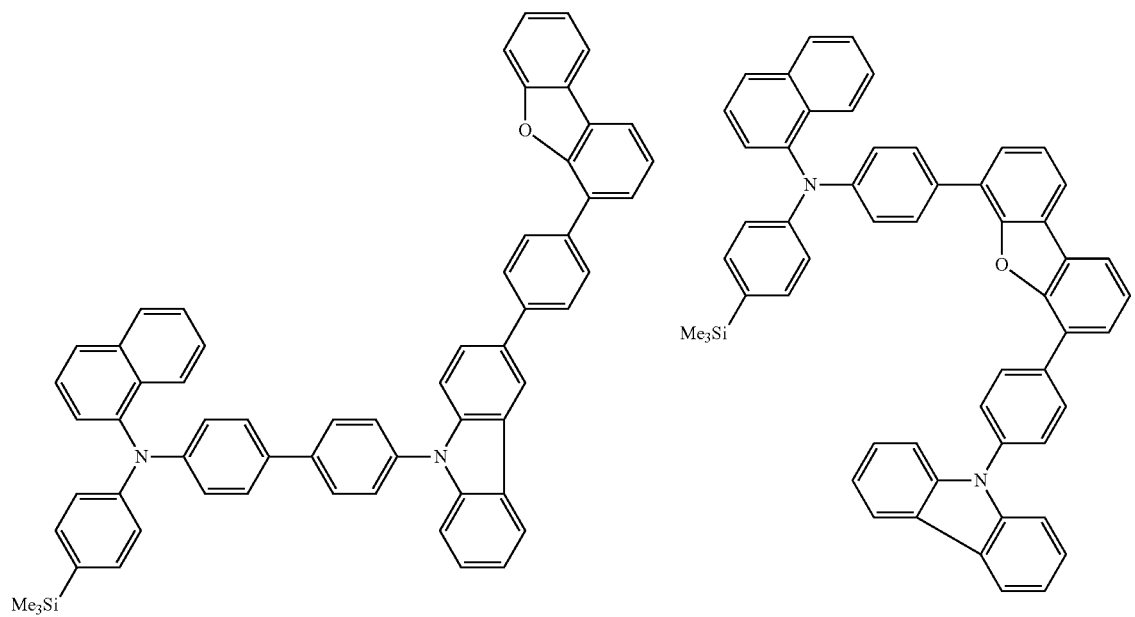

-continued
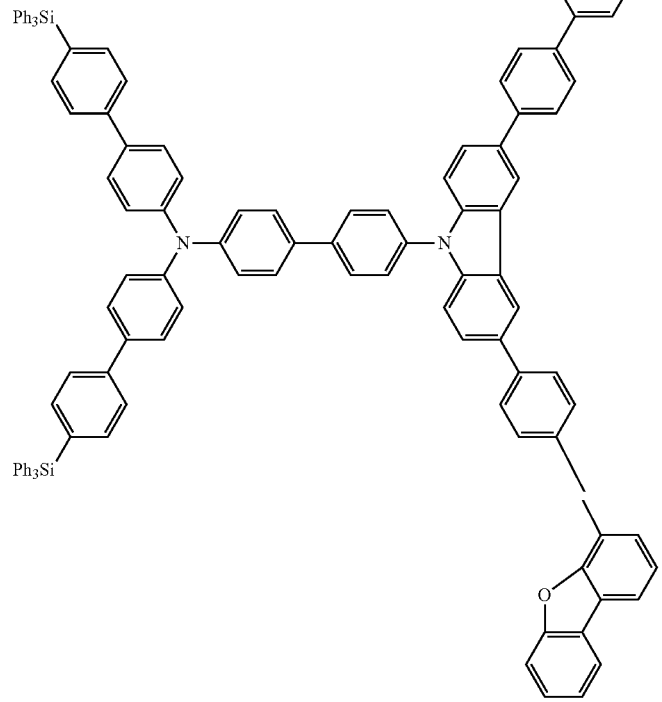
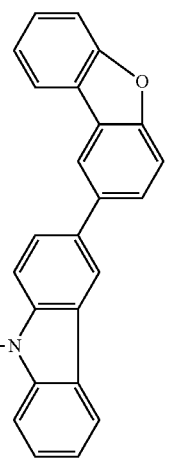

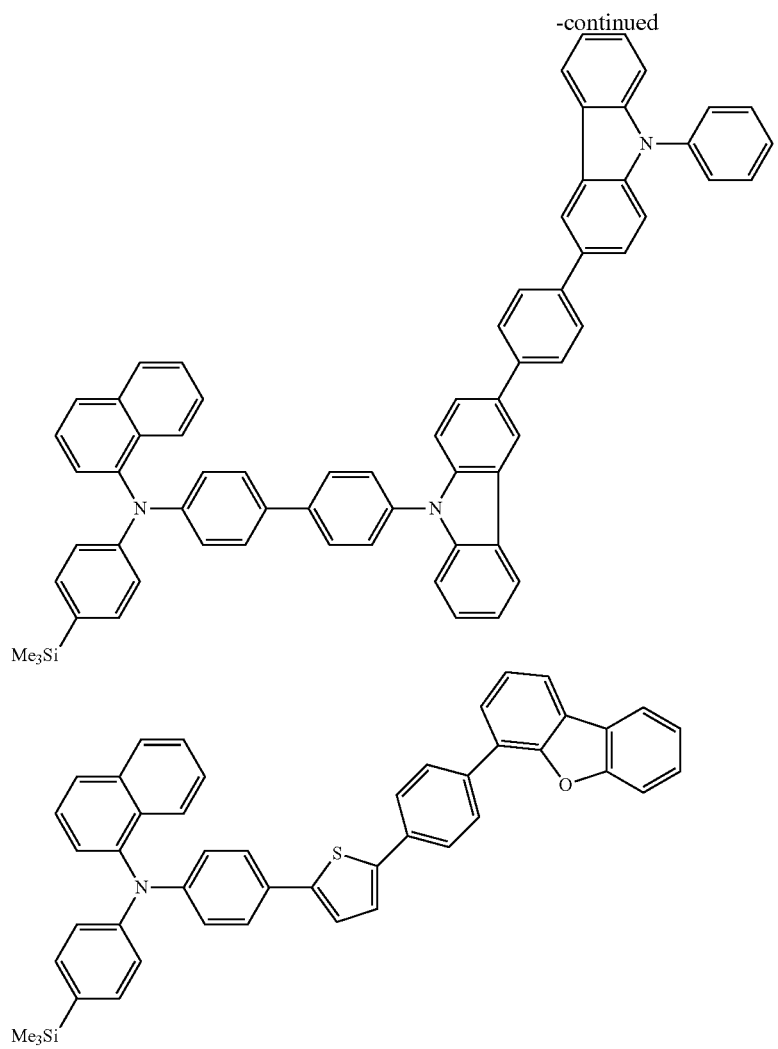

The aromatic amine derivative having a substituent represented by the general formula (1) of the present invention hardly crystallizes, and is preferably used as a light emitting material for an organic EL device, in particular, as a hole transporting material for an organic EL device. An organic EL device using the aromatic amine derivative of the present invention has a long lifetime even at high temperatures.

Next, a method of producing the aromatic amine derivative of the present invention is described.

The method of producing the aromatic amine derivative having a substituent represented by the general formula (1) of the present invention is not particularly limited, and is, for example, as described below.

Description is given by taking a method of producing the aromatic amine derivative of the present invention represented by the general formula (13) as an example. The aromatic amine derivative can be synthesized by, for example, the following reactions.

First, a halide [such as 4-bromobiphenyl] and a compound that produces an amino group [such as acetamide] are caused to react with each other in the presence of catalysts [a metal halide such as copper iodide and an amine such as N,N'-dimethylethylenediamine] and an alkaline substance [such as potassium carbonate] in a solvent [such as xylene] at 50 to 250° C. After that, the resultant is subjected to a reaction in the presence of an alkaline substance [such as potassium carbonate] and water in a solvent [such as xylene] at 50 to 250° C. Thus, an intermediate X is synthesized. The reactions are preferably performed under an atmosphere of an inert gas such as argon.

Separately, halides that produce a structure represented by the general formula (1) [such as carbazole and 4-iodo-4'-bromobiphenyl] are caused to react with each other in the presence of catalysts [such as copper iodide (CuI) and an amine such as trans-1,2-cyclohexanediamine] in a solvent [such as 1,4-dioxane] and an alkaline compound [such as tripotassium phosphate] at 50 to 150° C. After that, the resultant is subjected to a reaction in the presence of an iodinating agent [such as potassium iodide or potassium iodate] and an acid [such as sulfuric acid] in a solvent [such as ethanol] at 25 to 150° C. to provide an iodinated body. Further, a boron oxide that produces a structure represented by the general formula (1) [such as dibenzofuran-4-boronic acid] is caused to react with the iodinated body so that an intermediate Y ($L^1$-A-B) may be synthesized. The reactions are preferably performed under an atmosphere of an inert gas such as argon.

Next, the intermediate X and the intermediate Y are caused to react with each other in the presence of catalysts [such as t-butoxy sodium and tris(dibenzylideneacetone)dipalladium (0)] in a solvent [such as dry toluene] at 0 to 150° C. Thus, the aromatic amine derivative of the present invention can be synthesized. The reaction is preferably performed under an atmosphere of an inert gas such as argon.

After the completion of the reaction, the reaction product is cooled to room temperature, and then water is added to filtrate the product. The filtrate is extracted with a solvent such as toluene, and is then dried with a drying agent such as anhydrous magnesium sulfate. The dried product is desolvated under reduced pressure so as to be concentrated. The resultant crude product is subjected to column purification, and is then recrystallized with a solvent such as toluene. The crystal is separated by filtration, and is then dried. Thus, the aromatic amine derivative of the present invention that has been purified is obtained.

Upon introduction of an aryl group between the two kinds of hetero compounds of the intermediate Y, in, for example, the above-mentioned reaction example of the intermediate Y, a compound having a structure ($L^1$-A-$L^2$-B) is obtained by subjecting a heteroarylboronic acid [such as 4-(4-dibenzofuranyl)phenylboronic acid] instead of a heteroboronic acid [such as dibenzofuran-4-boronic acid] to a reaction.

Although this example describes the case where A is represented by the general formula (3) and B is represented by the general formula (6), similar synthesis can be performed by an arbitrary combination of a boronic acid compound and a halogenated compound in the case of any other heterocyclic ring in the present invention. In addition, $L^1$ and $L^2$ can each be similarly introduced into the substituent represented by the general formula (1) by an arbitrary combination of a boronic acid compound and a halogenated compound.

In order that a plurality of substituents represented by the general formula (1) may be introduced into the aromatic amine derivative represented by the general formula (13), a halide that produces the substituent represented by the general formula (1) has only to be subjected as a halide to a reaction in an amount corresponding to the number of the substituents one wishes to introduce upon synthesis of the above-mentioned intermediate X. Next, the intermediate X and the intermediate Y are caused to react with each other in the same manner as that described above. Thus, the aromatic amine derivative of the present invention into which the substituent represented by the general formula (1) and the linking group represented by the general formula (2) are introduced can be synthesized. The reactions are preferably performed under an atmosphere of an inert gas such as argon.

A halide containing the substituent represented by the general formula (1) and a halide of a substituted or unsubstituted aryl group having 6 to 50 ring carbon atoms except the substituent represented by the general formula (1) can be arbitrarily introduced into the intermediate X. In addition, one or two aryl groups can be introduced, and further, an arbitrary combination of aryl groups can be introduced. A target product can be obtained by causing the amine compound (intermediate X) obtained as a result of the introduction and an arbitrary halide (intermediate Y) to react with each other. The order in which those halides are subjected to reactions and the manner in which the halides are combined can be determined in consideration of, for example, reactivity and the ease of purification.

In addition, compounds represented by the general formulae (14) to (17) can each be synthesized as in the case of the synthesis of the monoamine described above by changing the [halide] to the [halide including the substituent represented by the general formula (1)] in the synthesis of a known amine compound.

In addition, known technologies described in the following patent literatures (for example, JP 2003-171366 A, WO 2006/114921 A1, WO 2006/073054 A1, WO 2007/125714 A1, and WO 2008/062636 A1) may each be employed for any such synthesis as described above.

In the organic EL device of the present invention, a light emitting layer to be described later preferably contains at least one kind of the aromatic amine derivative of the present invention. The light emitting layer contains the aromatic amine derivative of the present invention at a content of preferably 0.01 to 20 wt %, more preferably 0.5 to 20 wt %, particularly preferably 1 to 20 wt %, most preferably 5 to 20 wt %.

Typical examples of the construction of the organic EL device of the present invention may include the following constructions:

(1) anode/light emitting layer/cathode;
(2) anode/hole injecting layer/light emitting layer/cathode;
(3) anode/light emitting layer/electron injecting layer/cathode;
(4) anode/hole injecting layer/light emitting layer/electron injecting layer/cathode;
(5) anode/organic semiconductor layer/light emitting layer/cathode;
(6) anode/organic semiconductor layer/electron barrier layer/light emitting layer/cathode;
(7) anode/organic semiconductor layer/light emitting layer/adhesion improving layer/cathode;
(8) anode/hole injecting layer/hole transporting layer/light emitting layer/electron injecting layer/cathode;
(9) anode/insulating layer/light emitting layer/insulating layer/cathode;
(10) anode/inorganic semiconductor layer/insulating layer/light emitting layer/insulating layer/cathode;
(11) anode/organic semiconductor layer/insulating layer/light emitting layer/insulating layer/cathode;
(12) anode/insulating layer/hole injecting layer/hole transporting layer/light emitting layer/insulating layer/cathode; and
(13) anode/insulating layer/hole injecting layer/hole transporting layer/light emitting layer/electron injecting layer/cathode.

Of those, the construction (8) is preferably used in ordinary cases. However, the construction is not limited to the foregoing.

<Light-Transmissive Substrate>

The organic EL device of the present invention is prepared by laminating a plurality of layers having any of the above-mentioned layer constructions on a light-transmissive substrate. Here, the light-transmissive substrate refers to a substrate which supports the organic EL device. It is preferred that the light-transmissive substrate have a light transmittance of 50% or more in the visible light region where the wavelength is 400 to 700 nm and be flat and smooth.

Specific examples of the light-transmissive substrate include a glass plate and a polymer plate. Examples of the glass plate include plates formed of soda-lime glass, glass containing barium and strontium, lead glass, aluminosilicate glass, borosilicate glass, barium borosilicate glass, and quartz. Further, examples of the polymer plate include plates formed of polycarbonate, acrylic, polyethylene terephthalate, polyether sulfide, and polysulfone.

<Anode>

A material having a work function of more than 4 eV is suitable as a conductive material to be used in the anode of the organic EL device of the present invention, and carbon, aluminum, vanadium, iron, cobalt, nickel, tungsten, silver, gold, platinum, palladium, and the like, and alloys thereof, metal oxides such as tin oxide and indium oxide to be used in an ITO substrate and an NESA substrate, and organic conductive resins such as polythiophene and polypyrrole are each used.

<Cathode>

A material having a work function of less than 4 eV is suitable as a conductive substance to be used in the cathode, and magnesium, calcium, tin, lead, titanium, yttrium, lithium, ruthenium, manganese, aluminum, lithium fluoride, and the like, and alloys thereof are each used. However, the material is not limited thereto. Representative examples of the alloys include, but not limited to, magnesium/silver, magnesium/indium, and lithium/aluminum. The ratio of any such alloy is controlled depending on, for example, the temperature of a deposition source, an atmosphere, and a degree of vacuum, and is selected so as to be a proper ratio. The anode and the cathode may each be formed of a layer construction having two or more layers as required.

The cathode can be prepared by forming a thin film of the conductive substance described above in accordance with a method such as vapor deposition or sputtering.

Here, when the light emitted from the light emitting layer is obtained through the cathode, it is preferred that the cathode have a transmittance of more than 10% with respect to the emitted light.

In addition, the cathode has a sheet resistivity of preferably several hundreds $\Omega\square$ cm or less and a thickness of generally 10 nm to 1 μm, preferably 50 to 200 nm.

<Insulating Layer>

Defects in pixels tend to be formed in organic EL devices due to leak and short circuit because an electric field is applied to ultra-thin films. In order to prevent the formation of the defects, it is preferred that a thin film layer having insulating property be inserted between the pair of electrodes.

Examples of a material to be used in the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. A mixture or laminate thereof may also be used for the insulating layer.

<Light Emitting Layer>

The light emitting layer of the organic EL device has all of the following functions (1) to (3).

(1) Injecting function: a function by which a hole can be injected from the anode or the hole injecting layer and an electron can be injected from the cathode or the electron injecting layer when an electric field is applied.

(2) Transporting function: a function of transporting the injected charges (i.e., the electron and the hole) by the force of the electric field.

(3) Light emitting function: a function of providing the field for recombination of the electron and the hole and leading the recombination to the emission of light.

It should be noted that the ease with which a hole is injected and the ease with which an electron is injected may differ from each other, and transporting abilities represented by the mobilities of the hole and the electron may vary. However, it is preferred that one of the charges be transported.

Examples of a host material or a doping material which can be used in the light emitting layer together with the aromatic amine derivative of the present invention include: polyfused aromatic compounds such as naphthalene, phenanthrene, rubrene, anthracene, tetracene, pyrene, perylene, chrysene, decacyclene, coronene, tetraphenylcyclopentadiene, pentaphenylcyclopentadiene, fluorene, spirofluorene, 9,10-diphenylanthracene, 9,10-bis(phenylethinyl)anthracene, and 1,4-bis(9'-ethinylanthracene)benzene and derivatives thereof; organic metal complexes such as tris(8-quinolinolato)aluminum and bis-(2-methyl-8-quinolinolato)-4-(phenylphenolato)aluminum; a triarylamine derivative; a styrylamine derivative; a stilbene derivative; a coumarin derivative; a pyrane derivative; an oxazone derivative; a benzothiazole derivative; a benzoxazole derivative; a benzimidazole derivative; a pyrazine derivative; a cinnamate derivative; a diketopyrrolopyrrole derivative; an acridone derivative; and a quinacridone derivative, but the material is not limited thereto.

In addition to the aromatic amine derivative of the present invention, a known light emitting material, doping material, hole injecting material, or electron injecting material can be further used in the plurality of layers as required. Alternatively, the aromatic amine derivative of the present invention can be used as a doping material. A reduction in the brightness or lifetime of the organic EL device due to quenching can be prevented by structuring the organic thin film layer from a plurality of layers. A light emitting material, a doping material, a hole injecting material, and an electron injecting material can be used in combination as required. In addition, a doping material can achieve an improvement in luminous brightness or luminous efficiency, and the emission of red or blue light. In addition, the hole injecting layer, the light emitting layer, and the electron injecting layer may each be formed of a layer construction having two or more layers. At that time, in the case of the hole injecting layer, a layer into which a hole is injected from an electrode is called a hole injecting layer, and a layer that accepts the hole from the hole injecting layer and transports the hole to the light emitting layer is called a hole transporting layer. Similarly, in the case of the electron injecting layer, a layer into which an electron is injected from an electrode is called an electron injecting layer, and a layer that accepts the electron from the electron injecting layer and transports the electron to the light emitting layer is called an electron transporting layer. Each of those layers is selected and used depending on the respective factors such as the energy level of its material, the heat resistance of the material, and the adhesiveness of the material with an organic layer or a metal electrode.

The hole injecting/transporting layer is a layer that aids the injection of a hole into the light emitting layer and transports the hole to a light emitting region. The layer has a large hole mobility, and typically has an ionization energy as small as 5.7 eV or less. A material that transports a hole to the light emitting layer at an additionally low electric field intensity is preferred for such hole injecting/transporting layer, and a material having a hole mobility of at least $10^{-4}$ cm$^2$/V·sec at the time of the application of an electric field of, for example, $10^4$ to $10^6$ V/cm is more preferred.

As described in the foregoing, the aromatic amine derivative of the present invention is particularly preferably used in the hole injecting/transporting layer.

When the aromatic amine derivative of the present invention is used in a hole transporting zone, the hole injecting/transporting layer may be formed of the aromatic amine derivative of the present invention alone, or the derivative may be used as a mixture with any other material.

The other material mixed with the aromatic amine derivative of the present invention to form the hole injecting/transporting layer is not particularly limited as long as the material has the preferred nature, and an arbitrary material selected from materials conventionally used as charge transporting materials for holes in photoconductive materials, and known materials used in the hole injecting/transporting layers of organic EL devices can be used. In the present invention, a material that has a hole transporting ability and can be used in the hole transporting zone is called a hole transporting material.

Specific examples of the other material for a hole injecting/transporting layer other than the aromatic amine derivative of the present invention include, but are not limited to, a phthalocyanine derivative, a naphthalocyanine derivative, a porphyrin derivative, oxazole, oxadiazole, triazole, imidazole, imidazolone, imidazolethione, pyrazoline, pyrazolone, tetrahydroimidazole, oxazole, oxadiazole, hydrazone, acylhydrazone, polyarylalkane, stilbene, butadiene, benzidine type triphenylamine, styrylamine type triphenylamine, diamine type triphenylamine, derivatives thereof, and polymer materials such as polyvinyl carbazole, polysilane, and a conductive polymer.

Of the hole injecting materials that can be used in the organic EL device of the present invention, more effective hole injecting materials are an aromatic tertiary amine derivative and a phthalocyanine derivative.

Examples of the aromatic tertiary amine derivative include, but are not limited to, triphenylamine, tritolylamine, tolyldiphenylamine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)-phenanthrene-9,10-diamine, N,N-bis(4-di-4-tolylaminophenyl)-4-phenyl-cyclohexane, and an oligomer or polymer having one of the aromatic tertiary amine skeletons.

Examples of the phthalocyanine (Pc) derivative include, but are not limited to, phthalocyanine derivatives such as H$_2$Pc, CuPc, CoPc, NiPc, ZnPc, PdPc, FePc, MnPc, ClAlPc, ClGaPc, ClInPc, ClSnPc, Cl$_2$SiPc, (HO)AlPc, (HO)GaPc, VOPc, TiOPc, MoOPc, and GaPc-O-GaPc, and naphthalocyanine derivatives. In addition, the organic EL device of the present invention is preferably formed of a layer containing each of those aromatic tertiary amine derivatives and/or each of phthalocyanine derivatives, for example, the hole transporting layer or the hole injecting layer between a light emitting layer and an anode.

Next, the electron injecting layer and the electron transporting layer are described. Each of the electron injecting layer and the electron transporting layer is a layer which helps injection of electrons into the light emitting layer, transports the electrons to the light emitting region, and exhibits a large electron mobility. Further, the adhesion improving layer is an electron injecting layer including a material exhibiting particularly improved adhesion with the cathode.

In addition, it is known that, in an organic EL device, emitted light is reflected by an electrode (cathode in this case), and hence emitted light directly extracted from an anode and emitted light extracted via the reflection by the electrode interfere with each other. The film thickness of the electron transporting layer is appropriately selected from the range of several nanometers to several micrometers in order that the interference effect may be effectively utilized. In particular, when the film thickness of the electron transporting layer is large, an electron mobility is preferably at least $10^{-6}$ cm$^2$/V·s or more upon application of an electric field of $10^4$ to $10^6$V/cm in order to avoid an increase in voltage.

Specific examples of a material to be used in the electron injecting layer include fluorenone, anthraquinodimethane, diphenoquinone, thiopyranedioxide, oxazole, oxadiazole, triazole, imidazole, perylenetetracarboxylic acid, fluorenylidenemethane, anthraquinodimethane, anthrone, and derivatives thereof, but are not limited thereto. In addition, an electron-accepting substance can be added to the hole injecting material or an electron-donating substance can be added to the electron injecting material to thereby sensitize the hole injecting material or the electron injecting material, respectively.

In the organic EL device of the present invention, more effective electron injecting materials are a metal complex compound and a nitrogen-containing five-membered ring derivative.

Examples of the metal complex compound include, but are not limited to, 8-hydroxyquinolinatolithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, and bis(2-methyl-8-quinolinato)(2-naphtholato)gallium.

Examples of the nitrogen-containing five-membered derivative preferably include an oxazole derivative, a thiazole derivative, an oxadiazole derivative, a thiadiazole derivative, and a triazole derivative. Specific examples of the derivative include, but are not limited to, 2,5-bis(1-phenyl)-1,3,4-oxazole, dimethyl POPOP, 2,5-bis(1-phenyl)-1,3,4-thiazole, 2,5-bis(1-phenyl)-1,3,4-oxadiazole, 2-(4'-tert-butylphenyl)-5-(4"-biphenyl)-1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4"-biphenyl)-1,3,4-thiadiazole, 2,5-bis(1-naphthyl)-1,3,4-thiadiazole, 1,4-bis[2-(5-phenylthiadiazolyl)]benzene, 2-(4'-tert-butylphenyl)-5-(4"-biphenyl)-1,3,4-triazole, 2,5-bis(1-naphthyl)-1,3,4-triazole, and 1,4-bis[2-(5-phenyltriazolyl)]benzene.

In the organic EL device of the present invention, in addition to the aromatic amine derivative represented by any one of the general formulae (13) to (17), at least one kind of light emitting material, doping material, hole injecting material, and electron injecting material may be incorporated into the light emitting layer. In addition, a surface of the organic EL device obtained according to the present invention can be provided with a protective layer, or the entirety of the device can be protected with silicone oil, a resin, or the like with a view to improving the stability of the device against temperature, humidity, an atmosphere, or the like.

It is desirable that at least one surface of the organic EL device of the present invention be sufficiently transparent in the emission wavelength region of the device so that the device can efficiently emit light. A substrate is also desirably transparent. A transparent electrode is formed by using any one of the above-mentioned conductive materials, and is set by a method such as vapor deposition or sputtering in such a manner that desired translucency is secured. The light transmittance of an electrode on a light emitting surface is desirably 10% or more. The substrate is not limited as long as it has mechanical strength, thermal strength, and transparency. Examples of the substrate include a glass substrate and a transparent resin film. Examples of the transparent resin film include polyethylene, an ethylene-vinyl acetate copolymer, an ethylene-vinyl alcohol copolymer, polypropylene, polystyrene, polymethyl methacrylate, polyvinyl chloride, polyvinyl alcohol, polyvinyl butyral, nylon, polyether ether ketone, polysulfone, polyether sulfone, a tetrafluoroethylene-perfluoroalkyl vinyl ether copolymer, polyvinyl fluoride, a tetrafluoroethylene-ethylene copolymer, a tetrafluoroethylene-hexafluoropropylene copolymer, polychlorotrifluoroethylene, polyvinylidene fluoride, polyester, polycarbonate, polyurethane, polyimide, polyetherimide, polyimide, and polypropylene.

Any one of dry film forming methods such as vacuum deposition, sputtering, plasma, and ion plating, and wet film forming methods such as spin coating, dipping, and flow coating is applicable to the formation of each layer of the organic EL device of the present invention. The thickness of each layer is not particularly limited, but must be set to an appropriate thickness. An excessively large thickness requires an increased applied voltage for obtaining certain optical output, resulting in poor efficiency. An excessively small thickness causes a pin hole or the like, with the result that sufficient luminous brightness cannot be obtained even when an electric field is applied. In general, the thickness is in the range of preferably 5 nm to 10 µm, more preferably 10 nm to 0.2 µm.

In the case of a wet film forming method, a material for forming each layer is dissolved or dispersed into an appropriate solvent such as ethanol, chloroform, tetrahydrofuran, or dioxane, to thereby form a thin film. In this case, any one of the above-mentioned solvents may be used.

An organic EL material-containing solution containing the aromatic amine derivative of the present invention as an organic EL material and a solvent can be used as a solution suitable for such wet film forming method. In addition, an appropriate resin or additive may be used in each of the organic thin film layers for, for example, improving film formability or preventing a pin hole in the layer.

Examples of an available resin include: insulating resins such as polystyrene, polycarbonate, polyarylate, polyester, polyamide, polyurethane, polysulfone, polymethyl methacrylate, polymethyl acrylate, and cellulose, and copolymers thereof; photoconductive resins such as poly-N-vinylcarbazole and polysilane; and conductive resins such as polythiophene and polypyrrole. In addition, examples of the additive include an antioxidant, a UV absorber, and a plasticizer.

<Method of Fabricating Organic EL Device>

An organic EL device can be fabricated by forming an anode, a light emitting layer, a hole injecting/transporting layer to be formed as required, an electron injecting/transporting layer to be formed as required, and a cathode by means of the various materials and layer formation methods given in the foregoing. Alternatively, the organic EL device can be fabricated in the order opposite to the foregoing commencing on the cathode and ending on the anode.

Hereinafter, an example of fabricating an organic EL device having a construction in which an anode, a hole injecting layer, a light emitting layer, an electron injecting layer, and a cathode are formed successively on a light-transmissive substrate is described.

First, on a suitable light-transmissive substrate, a thin film made of a material for the anode is formed in accordance with a method such as vapor deposition or sputtering so that the thickness of the formed thin film is 1 µm or less, preferably in the range of 10 to 200 nm. The formed thin film is used as the anode. Then, a hole injecting layer is formed on the anode. The hole injecting layer can be formed in accordance with such method as the vacuum vapor deposition method, the spin coating method, the casting method, the LB method, as described above. The vacuum vapor deposition method is preferred because a uniform film can be easily obtained and the possibility of formation of pin holes is small, for example. When the hole injecting layer is formed in accordance with the vacuum vapor deposition method, in general, it is preferred that the conditions be suitably selected from the following ranges: the temperature of a deposition source: 50 to 450° C.; the degree of vacuum: $10^{-7}$ to $10^{-3}$ Torr; the rate of deposition: 0.01 to 50 nm/s; the temperature of the substrate: −50 to 300° C.; and the thickness of the film: 5 nm to 5 µm, although the conditions of the vacuum vapor deposition are different depending on the compound to be used (material for the hole injecting layer) and the crystal structure and the recombination structure of the target hole injecting layer.

The organic EL device of the present invention can find use in applications including a flat luminous body such as the flat panel display of a wall hanging television, a light source for the backlight, meters, or the like of a copying machine, a printer, or a liquid crystal display, a display panel, and a signal lamp. In addition, the material of the present invention can be used in not only the field of an organic EL device but also the fields of an electrophotographic photosensitive member, a photoelectric conversion device, a solar cell, an image sensor, and the like.

EXAMPLES

Next, the present invention is described in more detail by way of examples. However, the present invention is by no means limited by these examples.

Synthesis Example 1

Synthesis of Intermediate 1

In a stream of argon, to a 1,000-mL three-necked flask, 47 g of 4-bromobiphenyl, 23 g of iodine, 9.4 g of periodic acid dihydrate, 42 mL of water, 360 mL of acetic acid, and 11 mL of sulfuric acid were charged, and the mixture was stirred at 65° C. for 30 minutes and was then subjected to a reaction at 90° C. for 6 hours. The reactant was poured into ice water, followed by filtering. The resultant was washed with water, and then washed with methanol. As a result, 67 g of a white powder were obtained. Main peaks having ratios m/z of 358 and 360 were obtained with respect to $C_{12}H_8BrI=359$ by a field desorption mass spectrometry (hereinafter, FD-MS) analysis, so the powder was identified as Intermediate 1

Synthesis Example 2

Synthesis of Intermediate 2

In a stream of argon, 16.8 g of diphenylamine, 36.0 g of Intermediate 1, 10 g of t-butoxysodium (manufactured by Hiroshima Wako Ltd.), 1.6 g of bis(triphenylphosphine) palladium (II) chloride (manufactured by TOKYO CHEMICAL INDUSTRY CO., LTD.), and 500 mL of xylene were added, and were then caused to react with each other at 130° C. for 24 hours.

After the resultant had been cooled, 1,000 mL of water were added to the resultant, and then the mixture was subjected to cerite filtration. The filtrate was extracted with toluene and dried with anhydrous magnesium sulfate. The dried product was concentrated under reduced pressure. The resultant crude product was subjected to column purification and recrystallized with toluene. The resultant was taken by filtration, and was then dried. As a result, 12.4 g of a pale yellow powder were obtained. FD-MS analysis identified the powder as Intermediate 2.

Synthesis Example 3

Synthesis of Intermediate 3

In a stream of argon, 17.0 g of benzamide, 68.8 g of 4-bromobiphenyl, 2.70 g of copper iodide, 40.8 g of potassium carbonate, and diethylbenzene were added, and were then caused to react with each other at 175° C. for 19 hours.

After the resultant had been cooled, clean water was added to the resultant, followed by filtration. The remainder was washed with acetone, methanol, and clean water three times each. As a result, 55.0 g of a benzamide body of Intermediate 3 were obtained.

55.0 grams of the benzamide body of Intermediate 3, 26.3 g of potassium hydroxide, 25 mL of clean water, and diethylbenzene were added, and were then caused to react with each other at 175° C. for 5.5 hours.

After the resultant had been cooled, clean water was added to the resultant, followed by filtration. The remainder was washed with acetone, methanol, and clean water three times each, and was then purified with a short column (toluene). The resultant solid was washed with n-hexane and dried under reduced pressure. As a result, 25.0 g of a white solid were obtained. FD-MS analysis identified the solid as Intermediate 3.

Synthesis Example 4

Synthesis of Intermediate 4

A reaction was performed in the same manner as in Synthesis Example 3 except that 4-bromo-p-terphenyl was used instead of 4-bromobiphenyl. As a result, 28.0 g of a white powder were obtained. The powder was identified as Intermediate 4 by FD-MS analysis.

Synthesis 5

Synthesis of Intermediate 5

150 grams (892 mmol) of dibenzofuran and 1 L of acetic acid were added into a flask. The air in the flask was replaced with nitrogen, and then the contents were dissolved under heating. 188 grams (1.18 mol) of bromine were dropped to the solution while the flask was sometimes cooled with water. After that, the mixture was stirred for 20 hours under air cooling. The precipitated crystal was separated by filtration, and was then sequentially washed with acetic acid and water. The washed crystal was dried under reduced pressure. The resultant crystal was purified by distillation under reduced pressure, and was then repeatedly recrystallized with methanol several times. Thus, 66.8 g of 2-bromodibenzofuran were obtained (in 31% yield). The resultant was identified as Intermediate 5 by FD-MS analysis.

Synthesis Example 6

Synthesis of Intermediate 6

Under an argon atmosphere, 400 mL of anhydrous THF were added to 24.7 g (100 mmol) of 2-bromodibenzofuran, and then 63 mL (100 mmol) of a solution of n-butyllithium in hexane having a concentration of 1.6 M were added to the mixture during the stirring of the mixture at −40° C. The reaction solution was stirred for 1 hour while being heated to 0° C. The reaction solution was cooled to −78° C. again, and then a solution of 26.0 g (250 mmol) of trimethyl borate in 50 mL of dry THF was dropped to the solution. The reaction solution was stirred at room temperature for 5 hours. 200 milliliters of 1N hydrochloric acid were added to the solution, and then the mixture was stirred for 1 hour. After that, the aqueous layer was removed. The organic layer was dried with magnesium sulfate, and then the solvent was removed by distillation under reduced pressure. The resultant solid was washed with toluene. Thus, 15.2 g of dibenzofuran-2-boronic acid were obtained (in 72% yield). The resultant was identified as Intermediate 6 by FD-MS analysis because a main peak having a ratio m/z of 212 was obtained with respect to $C_{12}H_9BO_3=212$.

Synthesis Example 7

Synthesis of Intermediate 7

Under an argon atmosphere, 300 mL of toluene and 150 mL of an aqueous solution of sodium carbonate having a concentration of 2 M were added to 28.3 g (100 mmol) of 4-iodobromobenzene, 22.3 g (105 mmol) of dibenzofuran-2-boronic acid (Intermediate 4), and 2.31 g (2.00 mmol) of tetrakis(triphenylphosphine) palladium (0), and then the mixture was heated while being refluxed for 10 hours.

Immediately after the completion of the reaction, the resultant was filtrated, and then the aqueous layer was removed. The organic layer was dried with sodium sulfate, and was then concentrated. The residue was purified by silica gel column chromatography. Thus, 26.2 g of a white crystal of 4-(4-bromophenyl)dibenzofuran were obtained (in 81% yield). The crystal was identified as Intermediate 7 by FD-MS analysis.

Synthesis Example 8

Synthesis of Intermediate 8

A reaction was performed in the same manner as in Synthesis Example 6 except that 32.3 g of Intermediate 7 were used instead of 2-bromodibenzofuran. As a result, 20.1 g of a white powder were obtained. The powder was identified as Intermediate 8 by FD-MS analysis.

Synthesis Example 9

Synthesis of Intermediate 9

A reaction was performed in the same manner as in Synthesis Example 6 except that 22.3 g of dibenzofuran-4-boronic acid were used instead of dibenzofuran-2-boronic acid. As a result, 23.1 g of a white powder were obtained. The powder was identified as Intermediate 9 by FD-MS analysis.

Synthesis Example 10

Synthesis of Intermediate 10

A reaction was performed in the same manner as in Synthesis Example 8 except that 32.3 g of Intermediate 9 were used instead of Intermediate 7. As a result, 18.6 g of a white powder were obtained. FD-MS analysis identified the powder as Intermediate 10.

Synthesis Example 11

Synthesis of Intermediate 11

Ina stream of argon, 670 g of carbazole, 850 kg of iodobenzene, 20 L of xylene, 460 g of t-BuONa, and palladium acetate (Pd(OAc)$_2$) were added, and then the mixture was refluxed for 8 hours. Impurities were filtrated, and then the filtrate was concentrated under reduced pressure and washed with hexane. After that, the washed product was dried. As a result, 820 g of phenylcarbazole were obtained as a white powder. In a stream of argon, 24 g of phenylcarbazole, 8.3 g of potassium iodide, 10.7 g of potassium iodate, 500 mL of ethanol, and 8 mL of sulfuric acid were added into a 1,000-mL three-necked flask, and then the mixture was stirred at 75° C. for 2 hours. After that, the reaction product was injected into ice water, and then the mixture was extracted with ethyl acetate and water. After having been washed with water, the extract was subjected to column chromatography with silica gel. As a result, 67 g of a white powder were obtained. A reaction was performed in the same manner as in the synthesis of Intermediate 1 except that 9-phenylcarbazole was used instead of 4-bromobiphenyl. As a result, 22.3 g of a white powder were obtained. FD-MS analysis identified the powder as Intermediate 11.

Synthesis Example 12

Synthesis of Intermediate 12

A reaction was performed in the same manner as in Synthesis Example 6 except that 36.9 g of Intermediate 11 were used instead of Intermediate 5. As a result, 14.5 g of a white powder were obtained. FD-MS analysis identified the powder as Intermediate 12.

Synthesis Example 13

Synthesis of Intermediate 13

A reaction was performed in the same manner as in Synthesis Example 7 except that 28.7 g of Intermediate 12 were used instead of Intermediate 6. As a result, 23.7 g of a white powder were obtained. FD-MS analysis identified the powder as Intermediate 13.

Synthesis Example 14

Synthesis of Intermediate 14

A reaction was performed in the same manner as in Synthesis Example 6 except that 39.8 g of Intermediate 13 were used instead of Intermediate 5. As a result, 18.2 g of a white powder were obtained. FD-MS analysis identified the powder as Intermediate 14.

Synthesis Example 15

Synthesis of Intermediate 15

In a stream of argon, 750 g of phenylboronic acid, 1,000 g of 2-bromothiophene, 142 g of tetrakis(triphenylphosphine) palladium ($Pd(PPh_3)_4$), 9 L of a 2-M solution of sodium carbonate ($Na_2CO_3$), and 15 L of dimethoxyethane were added into a 50-L reaction vessel, and were then caused to react with each other at 80° C. for 8 hours. The reaction liquid was extracted with toluene/water and dried with anhydrous sodium sulfate. The dried product was concentrated under reduced pressure, and then the resultant crude product was subjected to column purification. As a result, 786 g of a white powder were obtained.

In a stream of argon, 786 g of the compound obtained in the foregoing and 8 L of dimethylformamide (DMF) were added into a 20-L reaction vessel. After that, 960 g of N-bromosuccinimide (NBS) were slowly added to the mixture, and then the whole was subjected to a reaction at room temperature for 12 hours. The resultant was extracted with hexane/water and dried with anhydrous sodium sulfate. The dried product was concentrated under reduced pressure, and then the resultant crude product was subjected to column purification. As a result, 703 g of a white powder were obtained. FD-MS analysis identified the powder as Intermediate 15.

Synthesis Example 16

Synthesis of Intermediate 16

A reaction was performed in the same manner as in Synthesis Example 6 except that 23.9 g of Intermediate 15 were used instead of Intermediate 5. As a result, 14.2 g of a white powder were obtained. FD-MS analysis identified the powder as Intermediate 16.

Synthesis Example 17

Synthesis of Intermediate 17

A reaction was performed in the same manner as in Synthesis Example 7 except that 20.4 g of Intermediate 16 were used instead of Intermediate 6. As a result, 24.2 g of a white powder were obtained. FD-MS analysis identified the powder as Intermediate 17.

Synthesis Example 18

Synthesis of Intermediate 18

A reaction was performed in the same manner as in Synthesis Example 6 except that 31.5 g of Intermediate 17 were used instead of Intermediate 5. As a result, 18.8 g of a white powder were obtained. FD-MS analysis identified the powder as Intermediate 18.

Synthesis Example 19

Synthesis of Intermediate 19

Under an argon atmosphere, 2 ml of trans-1,2-cyclohexanediamine and 300 mL of 1,4-dioxane were added to 28.3 g (100 mmol) of 4-iodobromobenzene, 16.7 g (100 mmol) of carbazole, 0.2 g (1.00 mmol) of copper iodide (CuI), and 42.4 g (210 mmol) of tripotassium phosphate, and then the whole was subjected to a reaction at 100° C. for 20 hours.

After the completion of the reaction, 300 ml of water were added to the resultant before separation of layers, and the aqueous layer was removed. The organic layer was dried with sodium sulfate, and was then concentrated. The residue was purified by silica gel column chromatography. Thus, 18.3 g of a white crystal were obtained (in 57% yield). The crystal was identified as Intermediate 19 by FD-MS analysis.

Synthesis Example 20

Synthesis of Intermediate 20

A reaction was performed in the same manner as in Synthesis Example 6 except that 32.2 g of Intermediate 19 were used instead of Intermediate 5. As a result, 17.1 g of a white powder were obtained. FD-MS analysis identified the powder as Intermediate 20.

Synthesis Example 21

Synthesis of Intermediate 21

A reaction was performed in the same manner as in Synthesis Example 19 except that 35.9 g of Intermediate 1 were used instead of 4-iodobromobenzene. As a result, 24.1 g of a white powder were obtained. FD-MS analysis identified the powder as Intermediate 21.

Synthesis Example 22

Synthesis of Intermediate 22

A reaction was performed in the same manner as in Synthesis Example 11 except that 39.8 g of Intermediate 21 were used instead of phenylcarbazole. As a result, 25.1 g of a white powder were obtained. FD-MS analysis identified the powder as Intermediate 22.

Synthesis Example 23

Synthesis of Intermediate 23

A reaction was performed in the same manner as in Synthesis Example 9 except that 39.8 g of Intermediate 22 were used instead of 4-iodobromobenzene. As a result, 25.1 g of a white powder were obtained. FD-MS analysis identified the powder as Intermediate 23.

Synthesis Example 24

Synthesis of Intermediate 24

A reaction was performed in the same manner as in Synthesis Example 22 except that the usage of each of iodine and periodic acid dihydrate was increased by a factor of two. As a result, 26.1 g of a white powder were obtained. FD-MS analysis identified the powder as Intermediate 24.

Synthesis Example 25

Synthesis of Intermediate 25

A reaction was performed in the same manner as in Synthesis Example 23 except that: 65.0 g of Intermediate 24 were used instead of Intermediate 22; and the usage of dibenzofuran-4-boronic acid was increased by a factor of two. As a result, 29.2 g of a white powder were obtained. FD-MS analysis identified the powder as Intermediate 25.

Synthesis Example 26

Synthesis of Intermediate 26

A reaction was performed in the same manner as in Synthesis Example 22 except that 32.2 g of Intermediate 19 were used instead of Intermediate 21. As a result, 22.4 g of a white powder were obtained. FD-MS analysis identified the powder as Intermediate 26.

Synthesis Example 27

Synthesis of Intermediate 27

A reaction was performed in the same manner as in Synthesis Example 23 except that 44.8 g of Intermediate 26 were used instead of Intermediate 22. As a result, 18.1 g of a white powder were obtained. FD-MS analysis identified the powder as Intermediate 27.

Synthesis Example 28

Synthesis of Intermediate 28

A reaction was performed in the same manner as in Synthesis Example 27 except that: 32.3 g of Intermediate 10 were used instead of dibenzofuran-4-boronic acid; and 52.4 g of Intermediate 22 were used instead of Intermediate 26. As a result, 25.1 g of a white powder were obtained. FD-MS analysis identified the powder as Intermediate 28.

Synthesis Example 29

Synthesis of Intermediate 29

A reaction was performed in the same manner as in Synthesis Example 27 except that 32.3 g of Intermediate 8 were used instead of dibenzofuran-4-boronic acid. As a result, 20.6 g of a white powder were obtained. FD-MS analysis identified the powder as Intermediate 29.

Synthesis Example 30

Synthesis of Intermediate 30

A reaction was performed in the same manner as in Synthesis Example 25 except that 32.3 g of dibenzofuran-2-boronic acid were used instead of dibenzofuran-4-boronic acid. As a result, 27.1 g of a white powder were obtained. FD-MS analysis identified the powder as Intermediate 30.

Synthesis Example 31

Synthesis of Intermediate 31

A reaction was performed in the same manner as in Synthesis Example 25 except that 28.0 g of Intermediate 18 were used instead of dibenzofuran-4-boronic acid. As a result, 23.7 g of a white powder were obtained. FD-MS analysis identified the powder as Intermediate 31.

Synthesis Example 32

Synthesis of Intermediate 32

A reaction was performed in the same manner as in Synthesis Example 25 except that 28.7 g of Intermediate 12 were used instead of dibenzofuran-4-boronic acid. As a result, 28.1 g of a white powder were obtained. FD-MS analysis identified the powder as Intermediate 32.

Synthesis Example 33

Synthesis of Intermediate 33

A reaction was performed in the same manner as in Synthesis Example 25 except that 36.3 g of Intermediate 14 were used instead of dibenzofuran-4-boronic acid. As a result, 22.9 g of a white powder were obtained. FD-MS analysis identified the powder as Intermediate 33.

Synthesis Example 34

Synthesis of Intermediate 34

A reaction was performed in the same manner as in Synthesis Example 9 except that 16.5 g of 1,4-diiodobenzene were used instead of 4-iodobromobenzene. As a result, 11.3 g of a white powder were obtained. FD-MS analysis identified the powder as Intermediate 34.

Synthesis Example 35

Synthesis of Intermediate 35

A reaction was performed in the same manner as in Synthesis Example 11 except that 40.8 g of Intermediate 34 were used instead of phenylcarbazole. As a result, 32.1 g of a white powder were obtained. FD-MS analysis identified the powder as Intermediate 35.

Synthesis Example 36

Synthesis of Intermediate 36

A reaction was performed in the same manner as in Synthesis Example 12 except that 53.6 g of Intermediate 35 were used instead of Intermediate 11. As a result, 22.7 g of a white powder were obtained. FD-MS analysis identified the powder as Intermediate 36.

Synthesis Example 37

Synthesis of Intermediate 37

A reaction was performed in the same manner as in Synthesis Example 13 except that: Intermediate 36 was used instead of Intermediate 12; and Intermediate 1 was used instead of 4-iodobromobenzene. As a result, 25.6 g of a white powder were obtained. FD-MS analysis identified the powder as Intermediate 37.

Synthesis Example 38

Synthesis of Intermediate 38

A reaction was performed in the same manner as in Synthesis Example 11 except that the usage of each of iodine and periodic acid dihydrate was increased by a factor of two. As a result, 19.6 g of a white powder were obtained. FD-MS analysis identified the powder as Intermediate 38.

Synthesis Example 39

Synthesis of Intermediate 39

A reaction was performed in the same manner as in Synthesis Example 27 except that: 28.8 g of Intermediate 10 were used instead of dibenzofuran-4-boronic acid; and 49.5 g of Intermediate 38 were used instead of Intermediate 26. As a result, 21.3 g of a white powder were obtained. FD-MS analysis identified the powder as Intermediate 39.

Synthesis Example 40

Synthesis of Intermediate 40

A reaction was performed in the same manner as in Synthesis Example 12 except that 61.1 g of Intermediate 39 were used instead of Intermediate 11. As a result, 20.8 g of a white powder were obtained. FD-MS analysis identified the powder as Intermediate 40.

Synthesis Example 41

Synthesis of Intermediate 41

A reaction was performed in the same manner as in Synthesis Example 27 except that: 28.0 g of Intermediate 18 were used instead of dibenzofuran-4-boronic acid; and 49.5 g of Intermediate 38 were used instead of Intermediate 26. As a result, 24.3 g of a white powder were obtained. FD-MS analysis identified the powder as Intermediate 41.

Synthesis Example 42

Synthesis of Intermediate 42

A reaction was performed in the same manner as in Synthesis Example 12 except that 60.3 g of Intermediate 41 were used instead of Intermediate 11. As a result, 18.7 g of a white powder were obtained. FD-MS analysis identified the powder as Intermediate 42.

Synthesis Example 43

Synthesis of Intermediate 43

A reaction was performed in the same manner as in Synthesis Example 38 except that 16.6 g of dibenzofuran were used instead of phenylcarbazole. As a result, 20.3 g of a white powder were obtained. FD-MS analysis identified the powder as Intermediate 43.

Synthesis Example 44

Synthesis of Intermediate 44

A reaction was performed in the same manner as in Synthesis Example 39 except that: 42.0 g of Intermediate 43 were used instead of Intermediate 38; and 28.7 g of Intermediate 20 were used instead of Intermediate 10. As a result, 21.3 g of a white powder were obtained. FD-MS analysis identified the powder as Intermediate 44.

Synthesis Example 45

Synthesis of Intermediate 45

A reaction was performed in the same manner as in Synthesis Example 7 except that: 20.0 g of 4-bromophenyl boronic acid were used instead of dibenzofuran-2-boronic acid; and 53.5 g of Intermediate 44 were used instead of 4-iodobromobenzene. As a result, 18.2 g of a white powder were obtained. FD-MS analysis identified the powder as Intermediate 45.

Synthesis Example 46

Synthesis of Intermediate 46

A reaction was performed in the same manner as in Synthesis Example 44 except that 28.7 g of Intermediate 12 were used instead of Intermediate 20. As a result, 16.5 g of a white powder were obtained. FD-MS analysis identified the powder as Intermediate 46.

Synthesis Example 47

Synthesis of Intermediate 47

A reaction was performed in the same manner as in Synthesis Example 45 except that 53.5 g of Intermediate 46 were used instead of Intermediate 44. As a result, 22.4 g of a white powder were obtained. FD-MS analysis identified the powder as Intermediate 47.

Synthesis Example 48

Synthesis of Intermediate 48

A reaction was performed in the same manner as in Synthesis Example 44 except that 36.3 g of Intermediate 14 were used instead of Intermediate 20. As a result, 19.2 g of a white powder were obtained. FD-MS analysis identified the powder as Intermediate 48.

Synthesis Example 49

Synthesis of Intermediate 49

A reaction was performed in the same manner as in Synthesis Example 45 except that 53.5 g of Intermediate 48 were used instead of Intermediate 44. As a result, 23.1 g of a white powder were obtained. FD-MS analysis identified the powder as Intermediate 49.

Synthesis Example 50

Synthesis of 50

A reaction was performed in the same manner as in Synthesis Example 15 except that 12.0 g of Intermediate 10 were used instead of phenylboronic acid. As a result, 14.7 g of a white powder were obtained. FD-MS analysis identified the powder as Intermediate 50.

Synthesis Example 51

Synthesis of Intermediate 51

A reaction was performed in the same manner as in Synthesis Example 16 except that 40.5 g of Intermediate 50 were used instead of Intermediate 15. As a result, 18.5 g of a white powder were obtained. FD-MS analysis identified the powder as Intermediate 51.

Synthesis Example 52

Synthesis of Intermediate 52

A reaction was performed in the same manner as in Synthesis Example 17 except that 37.2 g of Intermediate 51 were used instead of Intermediate 16. As a result, 19.2 g of a white powder were obtained. FD-MS analysis identified the powder as Intermediate 52.

Synthesis Example 53

Synthesis of Intermediate 53

A reaction was performed in the same manner as in Synthesis Example 13 except that: 52.9 g of Intermediate 40 were used instead of Intermediate 12; and 35.9 g of Intermediate 1 were used instead of 4-iodobromobenzene. As a result, 35.5 g of a white powder were obtained. FD-MS analysis identified the powder as Intermediate 53.

Synthesis Example 54

Synthesis of Intermediate 54

In a stream of argon, 185 g of 1-acetamide (manufactured by TOKYO CHEMICAL INDUSTRY CO., LTD.), 716 g of Intermediate 53 (manufactured by Wako Pure Chemical Industries, Ltd.), 544 g of potassium carbonate (manufactured by Wako Pure Chemical Industries, Ltd.), 12.5 g of a copper powder (manufactured by Wako Pure Chemical Industries, Ltd.), and 2 L of decalin were added, and were then caused to react with each other at 190° C. for 4 days. After the reaction, the resultant was cooled. 2 liters of toluene were added to the cooled product, and then insoluble matter was taken by filtration. The product taken by filtration was dissolved in 4.5 L of chloroform, and then insoluble matter was removed. After that, the remainder was subjected to an activated carbon treatment and concentrated. 3 liters of acetone were added to the concentrate, and then 511 g of the precipitated crystal were taken by filtration. As a result, an acetamide body of Intermediate 54 was obtained.

Further, in a stream of argon, the above-mentioned acetamide body was suspended in 5 L of ethylene glycol (manufactured by Wako Pure Chemical Industries, Ltd.) and 50 mL of water, and then 210 g of an 85% aqueous solution of potassium hydroxide were added to the suspension. After that, the mixture was subjected to a reaction at 120° C. for 8 hours. After the reaction, the reaction liquid was poured into 10 L of water. The precipitated crystal was taken by filtration, and was then washed with water and methanol. The resultant crystal was dissolved in 3 L of tetrahydrofuran under heating, and then the solution was subjected to an activated carbon treatment, followed by concentration. Acetone was added to the concentrate so that a crystal was precipitated. The crystal was taken by filtration, and as a result, 325 g of a white powder were obtained. FD-MS analysis identified the powder as Intermediate 54.

Synthesis Example 55

Synthesis of Intermediate 55

In a stream of argon, 9.2 g of aniline, 48.1 g of Intermediate 52, 13.6 g of t-butoxysodium (manufactured by Hiroshima Wako Ltd.), 0.92 g of tris(dibenzylideneacetone)dipalladium (0) (manufactured by Aldrich), and 600 mL of dry toluene were added, and were then caused to react with each other at 80° C. for 8 hours.

After the resultant had been cooled, 500 mL of water were added to the resultant, and then the mixture was subjected to cerite filtration. The filtrate was extracted with toluene and dried with anhydrous magnesium sulfate. The dried product was concentrated under reduced pressure. The resultant crude product was subjected to column purification and recrystallized with toluene. The resultant was taken by filtration, and was then dried. As a result, 30.5 g of an amine derivative (pale yellow powder) were obtained. FD-MS analysis identified the derivative as Intermediate 55.

Synthesis Example 56

Synthesis of Intermediate 56

A reaction was performed in the same manner as in Synthesis Example 55 except that 64.0 g of Intermediate 49 were used instead of Intermediate 52. As a result, 39.1 g of a white powder were obtained. FD-MS analysis identified the powder as Intermediate 56.

Synthesis Example 57

Synthesis of Intermediate 57

A reaction was performed in the same manner as in Synthesis Example 2 except that 65.2 g of Intermediate 54 were used instead of diphenylamine. As a result, 45.5 g of a white powder were obtained. FD-MS analysis identified the powder as Intermediate 57.

Synthesis Example 58

Synthesis of Intermediate 58

A reaction was performed in the same manner as in Synthesis Example 53 except that 52.1 g of Intermediate 42 were used instead of Intermediate 40. As a result, 35.5 g of a white powder were obtained. FD-MS analysis identified the powder as Intermediate 58.

Synthesis Example 59

Synthesis of Intermediate 59

A reaction was performed in the same manner as in Synthesis Example 15 except that 42.4 g of dibenzofuran-4-boronic acid were used instead of phenylboronic acid. As a result, 55.5 g of a white powder were obtained. FD-MS analysis identified the powder as Intermediate 59.

Synthesis Example 60

Synthesis of Intermediate 60

A reaction was performed in the same manner as in Synthesis Example 16 except that 55.5 g of Intermediate 59 were used instead of Intermediate 15. As a result, 24.6 g of a white powder were obtained. FD-MS analysis identified the powder as Intermediate 60.

Synthesis Example 61

Synthesis of Intermediate 61

A reaction was performed in the same manner as in Synthesis Example 17 except that 24.0 g of Intermediate 60 were used instead of Intermediate 16. As a result, 25.5 g of a white powder were obtained. FD-MS analysis identified the powder as Intermediate 61.

Synthesis Example 62

Synthesis of Intermediate 62

A reaction was performed in the same manner as in Synthesis Example 15 except that 42.4 g of Intermediate 6 were used instead of phenylboronic acid. As a result, 54.0 g of a white powder were obtained. FD-MS analysis identified the powder as Intermediate 62.

Synthesis Example 63

Synthesis of Intermediate 63

A reaction was performed in the same manner as in Synthesis Example 16 except that 54.0 g of Intermediate 62 were used instead of Intermediate 15. As a result, 28.6 g of a white powder were obtained. FD-MS analysis identified the powder as Intermediate 63.

Synthesis Example 64

Synthesis of Intermediate 64

A reaction was performed in the same manner as in Synthesis Example 17 except that 24.0 g of Intermediate 63 were used instead of Intermediate 16. As a result, 24.2 g of a white powder were obtained. FD-MS analysis identified the powder as Intermediate 64.

Synthesis Example 65

Synthesis of Intermediate 65

A reaction was performed in the same manner as in Synthesis Example 54 except that 100.0 g of Intermediate 61 were used instead of Intermediate 53. As a result, 24.8 g of a white powder were obtained. FD-MS analysis identified the powder as Intermediate 65.

Synthesis Example 66

Synthesis of Intermediate 66

A reaction was performed in the same manner as in Synthesis Example 54 except that 100.0 g of Intermediate 64 were used instead of Intermediate 53. As a result, 22.3 g of a white powder were obtained. FD-MS analysis identified the powder as Intermediate 66.

Example-of-Synthesis 1

Synthesis of Compound H1

In a stream of argon, 3.2 g of Intermediate 3, 5.6 g of Intermediate 23, 1.3 g of t-butoxysodium (manufactured by Hiroshima Wako Ltd.), 46 mg of tris(dibenzylideneacetone)dipalladium(0) (manufactured by Aldrich), 21 mg of tri-t-butylphosphine, and 50 mL of dry toluene were added, and were then caused to react with each other at 80° C. for 8 hours.

After the resultant had been cooled, 500 mL of water were added to the resultant, and then the mixture was subjected to cerite filtration. The filtrate was extracted with toluene and dried with anhydrous magnesium sulfate. The dried product was concentrated under reduced pressure. The resultant crude product was subjected to column purification and recrystallized with toluene. The resultant was taken by filtration, and was then dried. As a result, 4.4 g of a pale yellow powder were obtained. FD-MS analysis identified the powder as Compound H1.

Example-of-Synthesis 2

Synthesis of Compound H2

A reaction was performed in the same manner as in Example-of-Synthesis 1 Except that 7.3 g of Intermediate 25 were used instead of Intermediate 23. As a result, 4.2 g of a pale yellow powder were obtained. FD-MS analysis identified the powder as Compound H2.

Example-of-Synthesis 3

Synthesis of Compound H3

A reaction was performed in the same manner as in Example-of-Synthesis 1 except that: 7.3 g of Intermediate 25 were used instead of Intermediate 23; and 4.7 g of Intermediate 4 were used instead of Intermediate 3. As a result, 4.9 g of a pale yellow powder were obtained. FD-MS analysis identified the powder as Compound H3.

Example-of-Synthesis 4

Synthesis of Compound H4

A reaction was performed in the same manner as in Example-of-Synthesis 1 except that: 7.3 g of Intermediate 28 were used instead of Intermediate 23; and 4.7 g of Intermediate 4 were used instead of Intermediate 3. As a result, 4.3 g of a pale yellow powder were obtained. FD-MS analysis identified the powder as Compound H4.

Example-of-Synthesis 5

Synthesis of Compound H5

A reaction was performed in the same manner as in Example-of-Synthesis 1 except that 5.6 g of Intermediate 29 were used instead of Intermediate 23. As a result, 4.2 g of a pale yellow powder were obtained. FD-MS analysis identified the powder as Compound H5.

Example-of-Synthesis 6

Synthesis of Compound H6

A reaction was performed in the same manner as in Example-of-Synthesis 1 except that: 7.3 g of Intermediate 30 were used instead of Intermediate 23; and 2.2 g of N-phenyl-1-naphthylamine were used instead of Intermediate 3. As a result, 4.1 g of a pale yellow powder were obtained. FD-MS analysis identified the powder as Compound H6.

Example-of-Synthesis 7

Synthesis of Compound H7

A reaction was performed in the same manner as in Example-of-Synthesis 1 except that: 6.3 g of Intermediate 31 were used instead of Intermediate 23; and 4.7 g of Intermediate 4 were used instead of Intermediate 3. As a result, 5.1 g of a pale yellow powder were obtained. FD-MS analysis identified the powder as Compound H7.

Example-of-Synthesis 8

Synthesis of Compound H8

A reaction was performed in the same manner as in Example-of-Synthesis 1 except that 6.4 g of Intermediate 32 were used instead of Intermediate 23. As a result, 4.6 g of a pale yellow powder were obtained. FD-MS analysis identified the powder as Compound H8.

Example-of-Synthesis 9

Synthesis of Compound H9

A reaction was performed in the same manner as in Example-of-Synthesis 1 except that: 7.2 g of Intermediate 33 were used instead of Intermediate 23; and 6.1 g of Intermediate 4 were used instead of Intermediate 3. As a result, 5.1 g of a pale yellow powder were obtained. FD-MS analysis identified the powder as Compound H9.

Example-of-Synthesis 10

Synthesis of Compound H10

A reaction was performed in the same manner as in Example-of-Synthesis 1 except that 6.4 g of Intermediate 37 were used instead of Intermediate 23. As a result, 3.9 g of a pale yellow powder were obtained. FD-MS analysis identified the powder as Compound H10.

Example-of-Synthesis 11

Synthesis of Compound H11

A reaction was performed in the same manner as in Example-of-Synthesis 1 except that 7.2 g of Intermediate 53 were used instead of Intermediate 23. As a result, 4.7 g of a pale yellow powder were obtained. FD-MS analysis identified the powder as Compound H11.

Example-of-Synthesis 12

Synthesis of Compound H12

A reaction was performed in the same manner as in Example-of-Synthesis 1 except that 7.1 g of Intermediate 58 were used instead of Intermediate 23. As a result, 4.2 g of a pale yellow powder were obtained. FD-MS analysis identified the powder as Compound H12.

Example-of-Synthesis 13

Synthesis of Compound H13

A reaction was performed in the same manner as in Example-of-Synthesis 1 except that 5.6 g of Intermediate 45 were used instead of Intermediate 23. As a result, 3.3 g of a pale yellow powder were obtained. FD-MS analysis identified the powder as Compound H13.

Example-of-Synthesis 14

Synthesis of Compound H14

A reaction was performed in the same manner as in Example-of-Synthesis 1 except that 5.6 g of Intermediate 47 were used instead of Intermediate 23. As a result, 3.6 g of a pale yellow powder were obtained. FD-MS analysis identified the powder as Compound H14.

Example-of-Synthesis 15

Synthesis of Compound H15

A reaction was performed in the same manner as in Example-of-Synthesis 1 except that: 6.4 g of Intermediate 49 were used instead of Intermediate 23; and 4.7 g of Intermediate 4 were used instead of Intermediate 3. As a result, 5.2 g of a pale yellow powder were obtained. FD-MS analysis identified the powder as Compound H15.

Example-of-Synthesis 16

Synthesis of Compound H16

A reaction was performed in the same manner as in Example-of-Synthesis 1 except that 4.8 g of Intermediate 52 were used instead of Intermediate 23. As a result, 3.2 g of a pale yellow powder were obtained. FD-MS analysis identified the powder as Compound H16.

Example-of-Synthesis 17

Synthesis of Compound H17

A reaction was performed in the same manner as in Example-of-Synthesis 1 except that: 7.2 g of Intermediate 53 were used instead of Intermediate 23; and 1.6 g of N,N'-diphenylbenzidine were used instead of Intermediate 3. As a result, 3.1 g of a pale yellow powder were obtained. FD-MS analysis identified the powder as Compound H17.

Example-of-Synthesis 18

Synthesis of Compound H18

A reaction was performed in the same manner as in Example-of-Synthesis 1 except that: 4.0 g of Intermediate 2 were used instead of Intermediate 23; and 3.2 g of Intermediate 54 were used instead of Intermediate 3. As a result, 2.7 g of a pale yellow powder were obtained. FD-MS analysis identified the powder as Compound H18.

Example-of-Synthesis 19

Synthesis of Compound H19

A reaction was performed in the same manner as in Example-of-Synthesis 1 except that: 1.6 g of tris (4-bromophenyl) amine were used instead of Intermediate 23; and 4.9 g of Intermediate 55 were used instead of Intermediate 3. As a result, 2.3 g of a pale yellow powder were obtained. FD-MS analysis identified the powder as Compound H19.

Example-of-Synthesis 20

Synthesis of Compound H20

A reaction was performed in the same manner as in Example-of-Synthesis 1 except that: 8.8 g of Intermediate 57 were used instead of Intermediate 23; and 5.1 g of N,N'-diphenylbenzidine were used instead of Intermediate 3. As a result, 3.1 g of a pale yellow powder were obtained. FD-MS analysis identified the powder as Compound H20.

Example-of-Synthesis 21

Synthesis of Compound H21

A reaction was performed in the same manner as in Example-of-Synthesis 1 except that: 6.4 g of Intermediate 37 were used instead of Intermediate 23; and 4.7 g of Intermediate 4 were used instead of Intermediate 3. As a result, 4.1 g of a pale yellow powder were obtained. FD-MS analysis identified the powder as Compound H21.

Example-of-Synthesis 22

Synthesis of Compound H22

A reaction was performed in the same manner as in Example-of-Synthesis 1 except that: 5.6 g of Intermediate 45 were used instead of Intermediate 23; and 4.7 g of Intermediate 4 were used instead of Intermediate 3. As a result, 4.3 g of a pale yellow powder were obtained. FD-MS analysis identified the powder as Compound H22.

Example-of-Synthesis 23

Synthesis of Compound H23

A reaction was performed in the same manner as in Example-of-Synthesis 1 except that: 4.1 g of Intermediate 61 were used instead of Intermediate 23; and 4.7 g of Intermediate 4 were used instead of Intermediate 3. As a result, 4.7 g of a pale yellow powder were obtained. FD-MS analysis identified the powder as Compound H23.

Example-of-Synthesis 24

Synthesis of Compound H24

A reaction was performed in the same manner as in Example-of-Synthesis 1 except that: 4.1 g of Intermediate 64 were used instead of Intermediate 23; and 4.7 g of Intermediate 4 were used instead of Intermediate 3. As a result, 4.2 g of a pale yellow powder were obtained. FD-MS analysis identified the powder as Compound H24.

Example-of-Synthesis 25

Synthesis of Compound H25

A reaction was performed in the same manner as in Example-of-Synthesis 1 except that 4.1 g of Intermediate 61 were used instead of Intermediate 23. As a result, 3.7 g of a pale yellow powder were obtained. FD-MS analysis identified the powder as Compound H25.

Example-of-Synthesis 26

Synthesis of Compound H26

A reaction was performed in the same manner as in Example-of-Synthesis 1 except that 4.1 g of Intermediate 64 were used instead of Intermediate 23. As a result, 3.3 g of a pale yellow powder were obtained. FD-MS analysis identified the powder as Compound H26.

Example-of-Synthesis 27

Synthesis of Compound H27

A reaction was performed in the same manner as in Example-of-Synthesis 1 except that: 2.1 g of 4-bromobiphenyl were used instead of Intermediate 23; and 6.7 g of Intermediate 65 were used instead of Intermediate 3. As a result, 3.7 g of a pale yellow powder were obtained. FD-MS analysis identified the powder as Compound H27.

Example-of-Synthesis 28

Synthesis of Compound H28

A reaction was performed in the same manner as in Example-of-Synthesis 1 except that: 2.1 g of 4-bromobiphenyl were used instead of Intermediate 23; and 6.7 g of Intermediate 66 were used instead of Intermediate 3. As a result, 3.1 g of a pale yellow powder were obtained. FD-MS analysis identified the powder as Compound H28.

The structural formulae of Intermediates 1 to 66 synthesized in Synthesis Examples 1 to 66 and Compounds H1 to H28 synthesized in Examples-of-Synthesis 1 to 28 each serving as the aromatic amine derivative of the present invention described in the foregoing, and Comparative Compounds 1 to 7 are as shown below.

[Chem. 15]

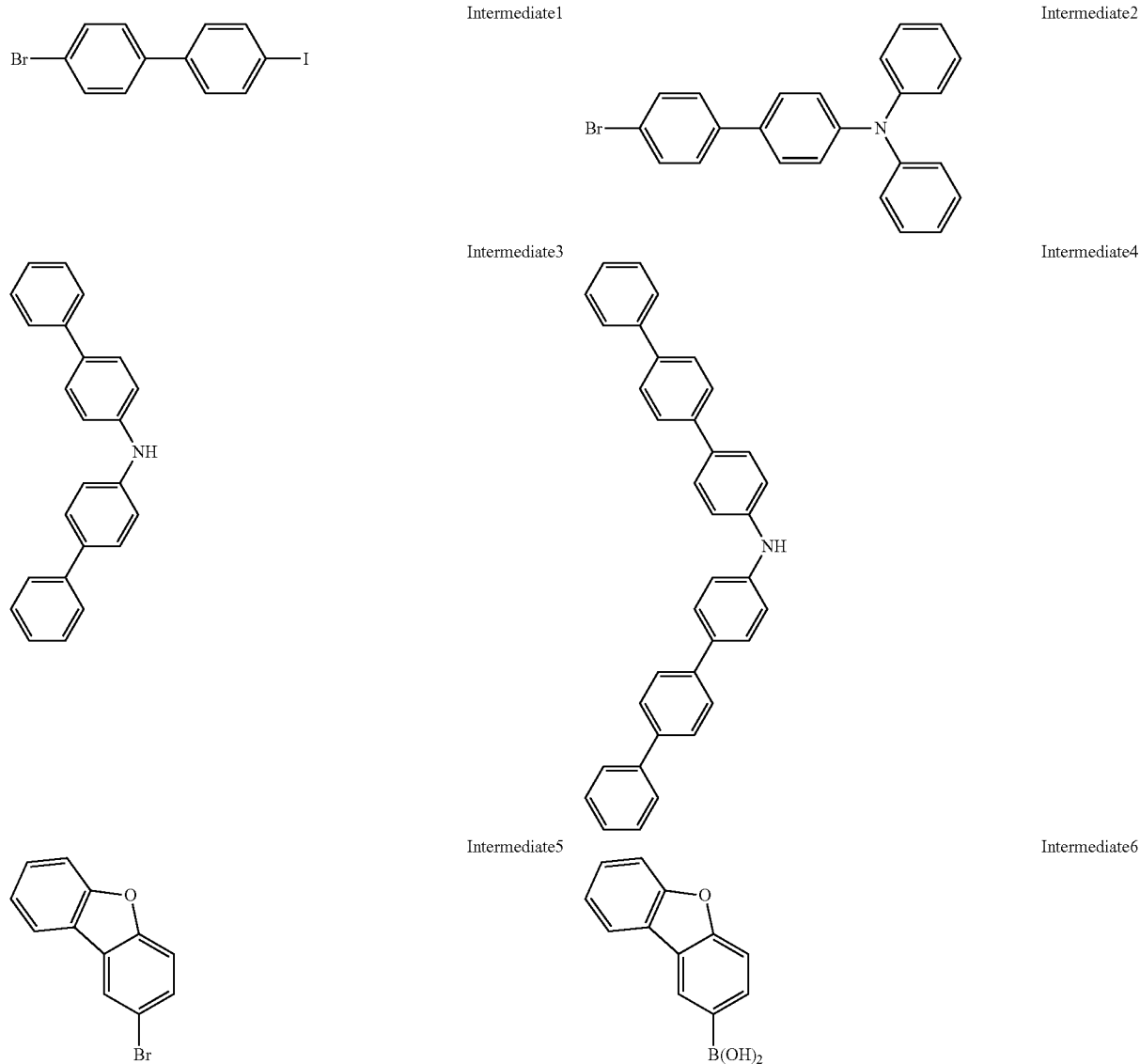

-continued
Intermediate7
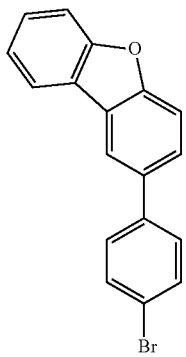
Intermediate8
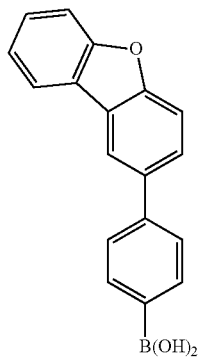
Intermediate9
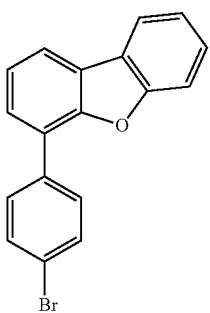
Intermediate10
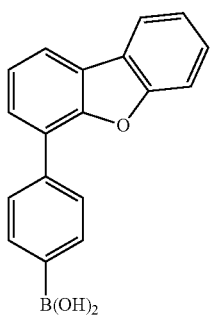
Intermediate11
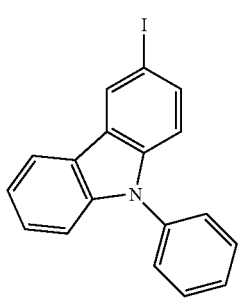
Intermediate12
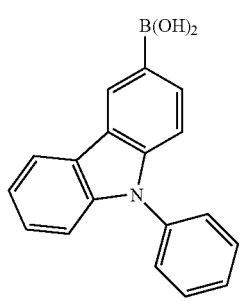
Intermediate13
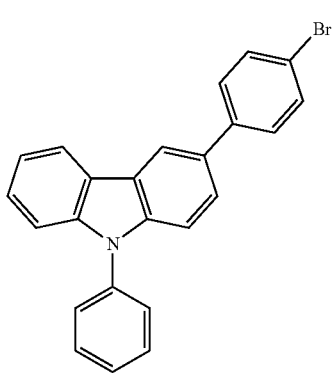
Intermediate14
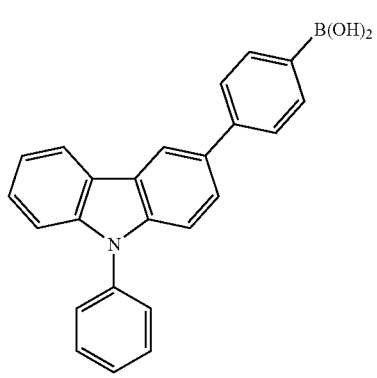
Intermediate15
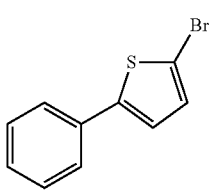

[Chem. 16]
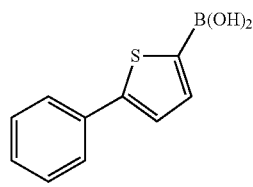
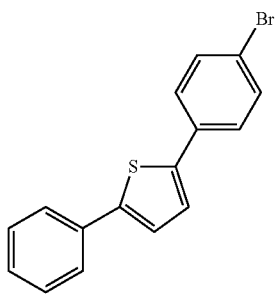
Intermediate16
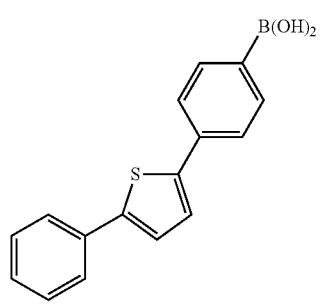
Intermediate18
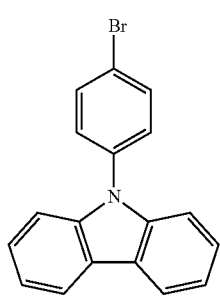
Intermediate19
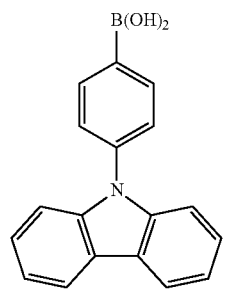
Intermediate20
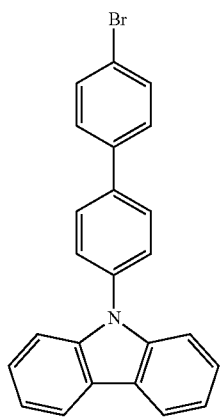
Intermediate21
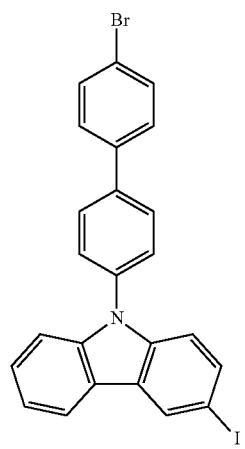
Intermediate22
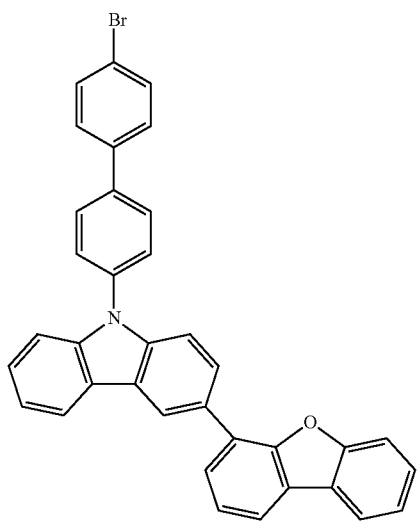
Intermediate23

-continued
Intermediate24
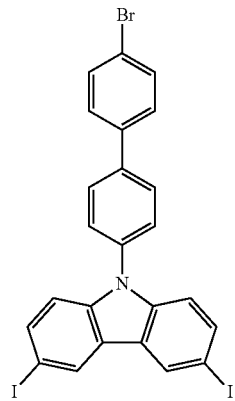
Intermediate25
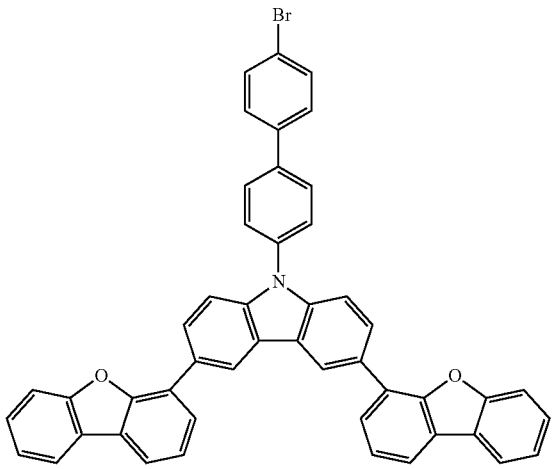
Intermediate26
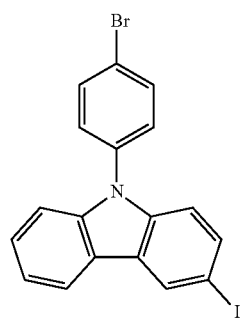
Intermediate27
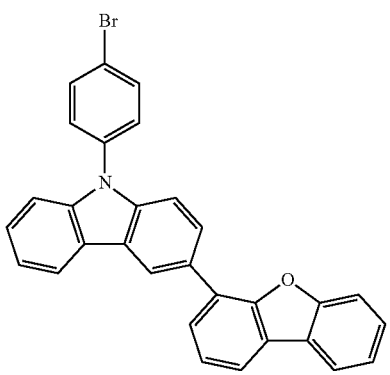
Intermediate28
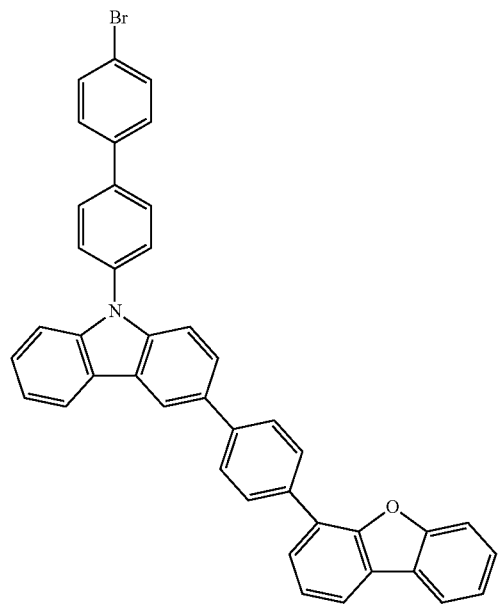
Intermediate29
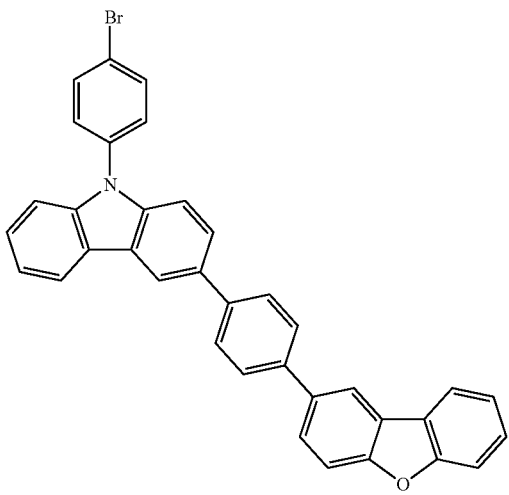

-continued
Intermediate30
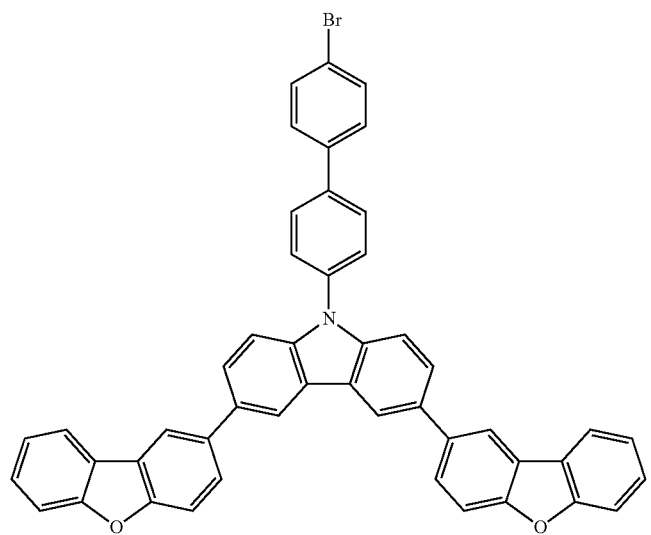
[Chem. 17]
Intermediate31
Intermediate32
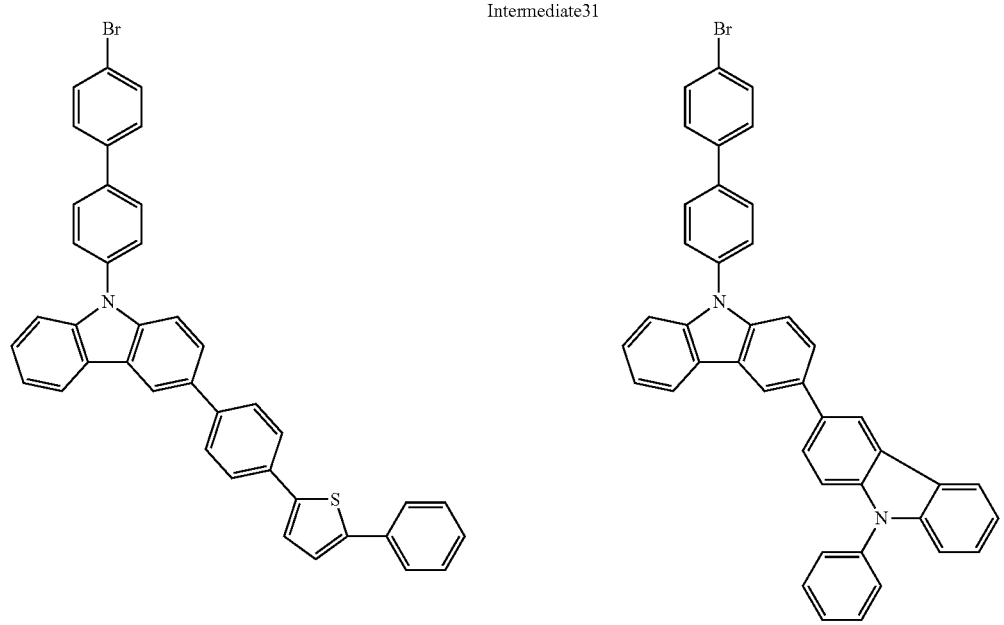

-continued
Intermediate33
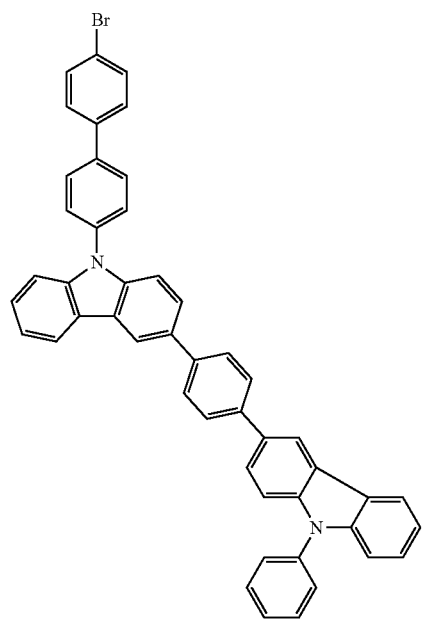
Intermediate34
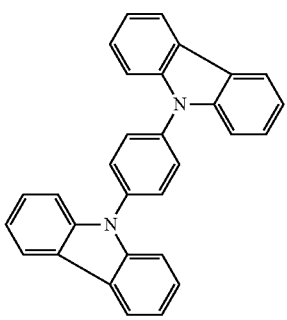
Intermediate35
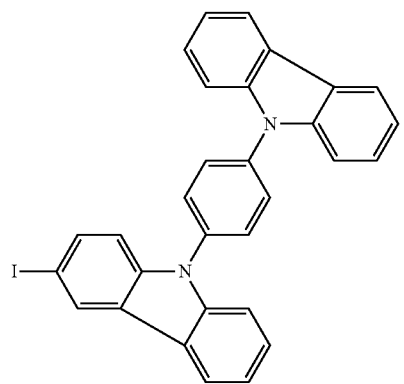
Intermediate36
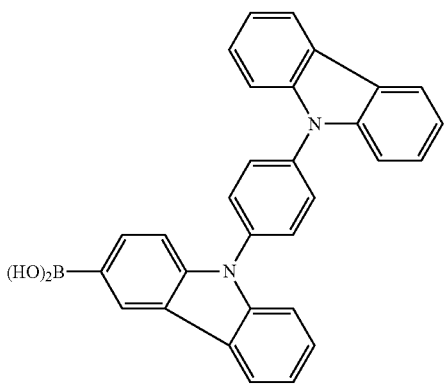
Intermediate37
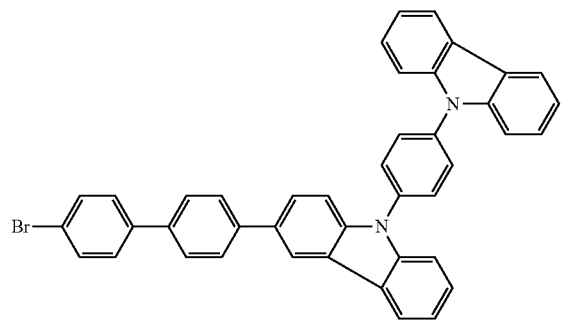
Intermediate38
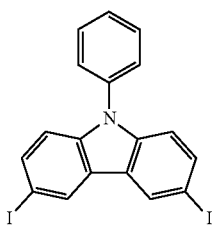

-continued
Intermediate39
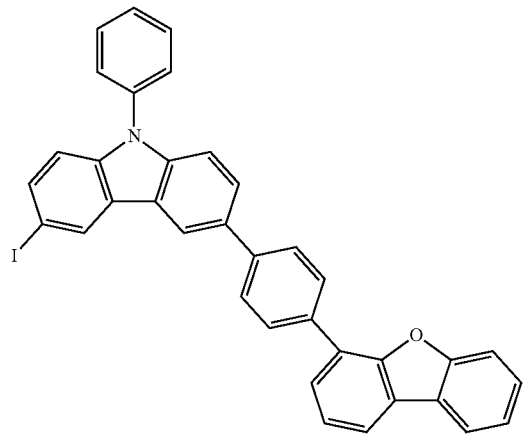
Intermediate41
Intermediate40
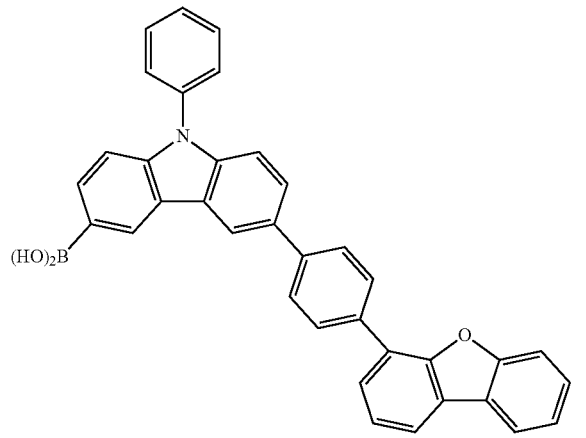
Intermediate42
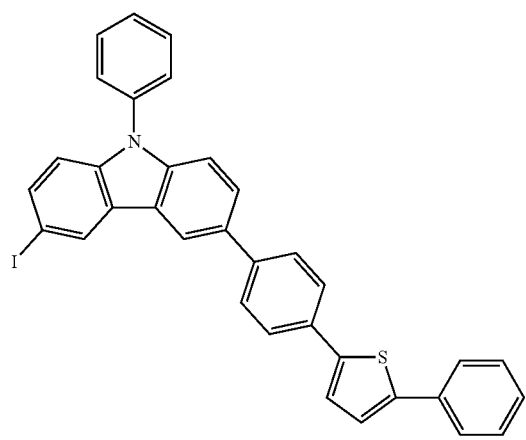
Intermediate43
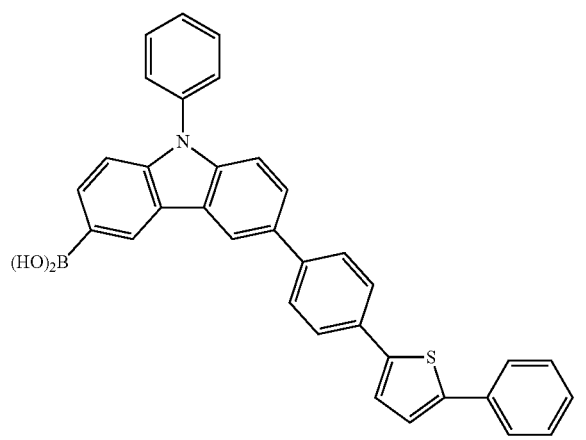
Intermediate44
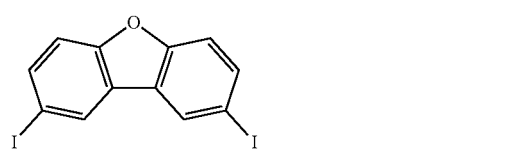
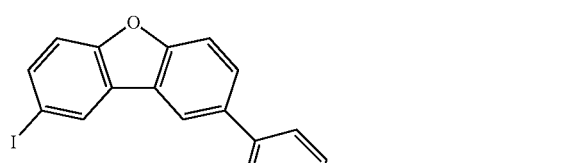
Intermediate45
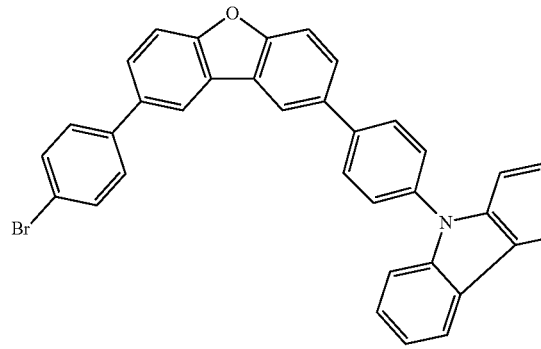

-continued
[Chem. 18]
Intermediate46
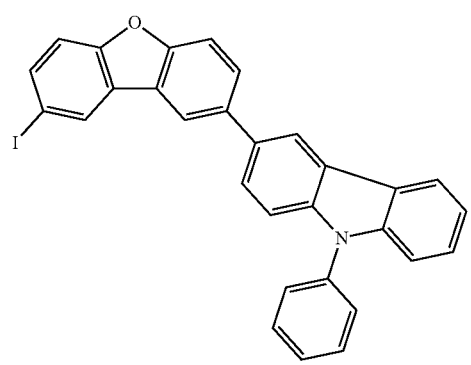
Intermediate47
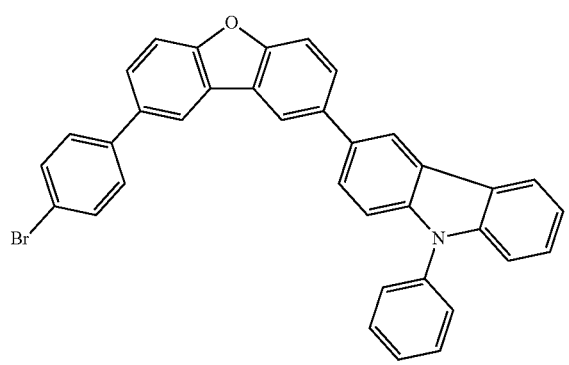
Intermediate48
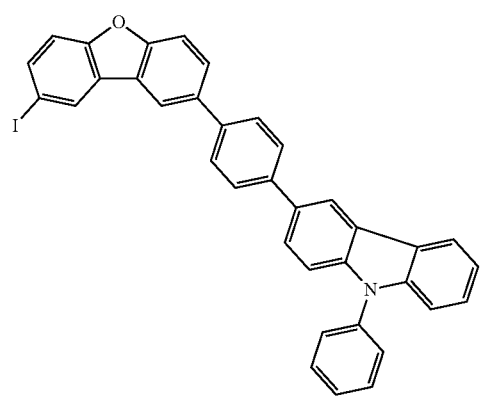
Intermediate49
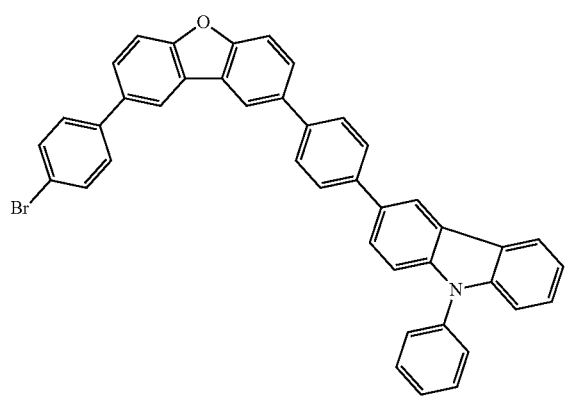
Intermediate50
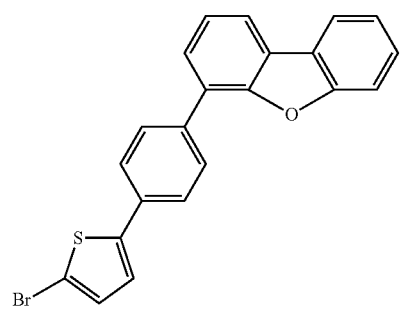
Intermediate51
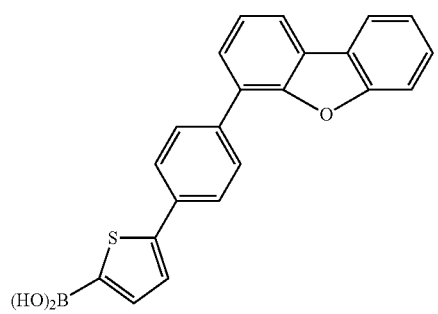
Intermediate52
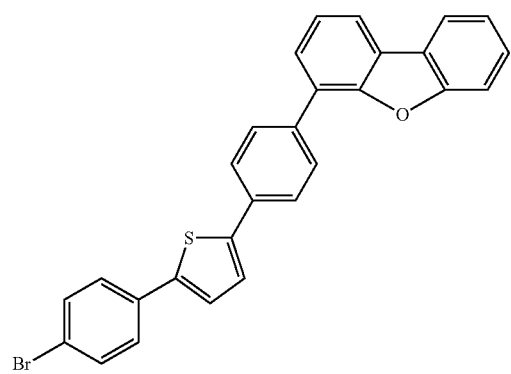

Intermediate53
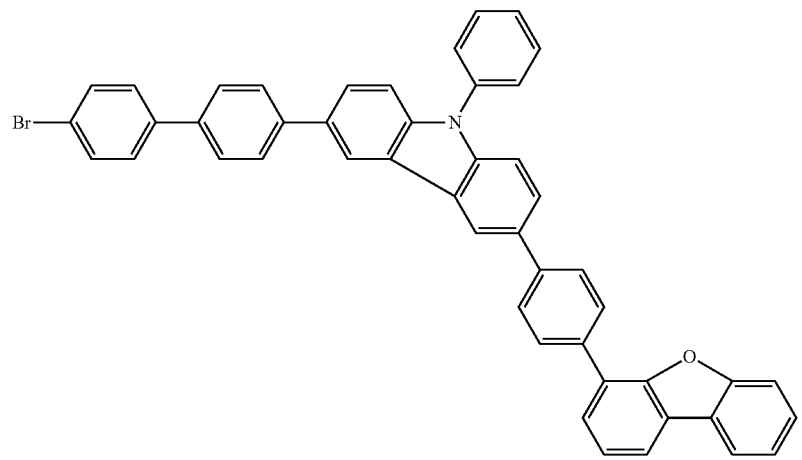
Intermediate54
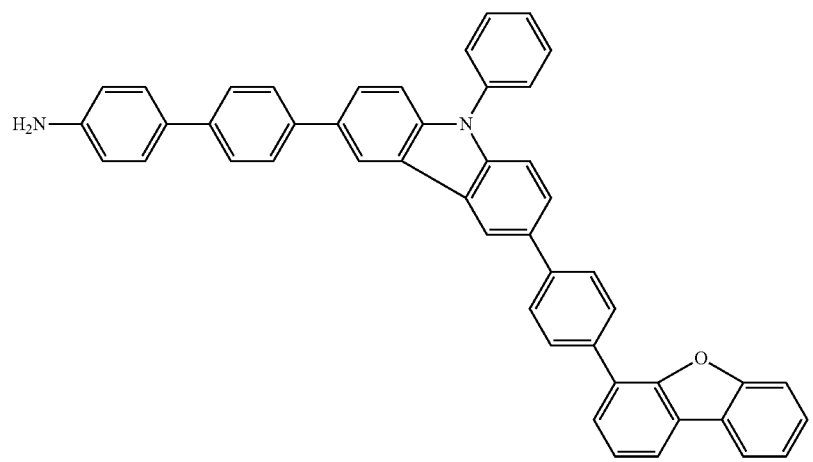
Intermediate55
Intermediate56
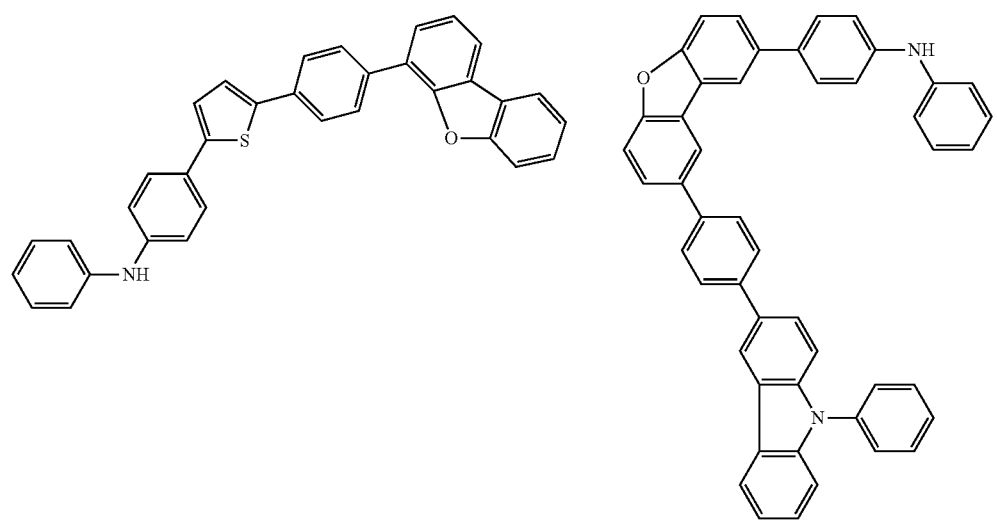

-continued
Intermediate57
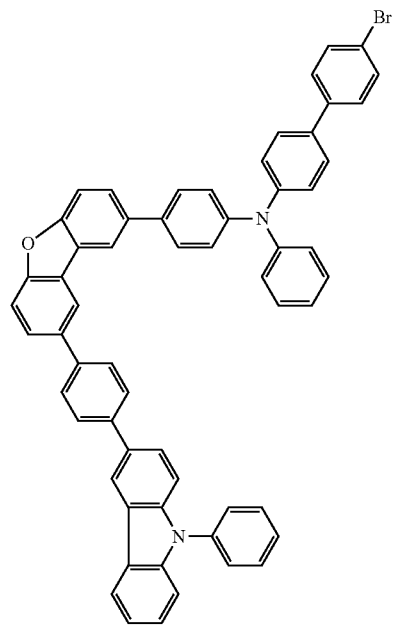
Intermediate58
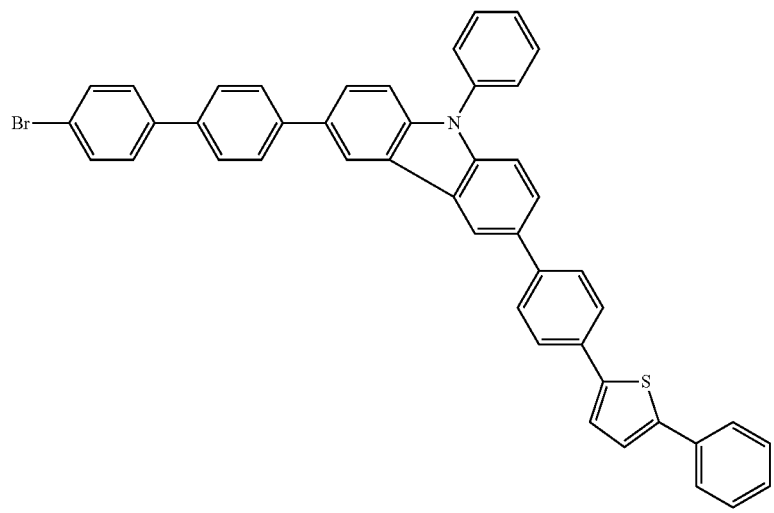
[Chem. 19]
Intermediate59
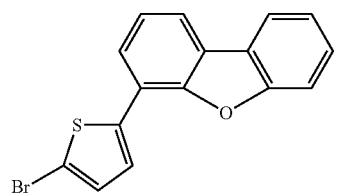
Intermediate60
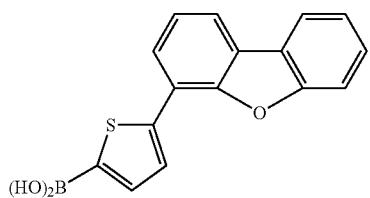
Intermediate61
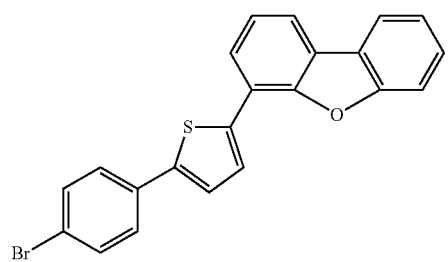
Intermediate62
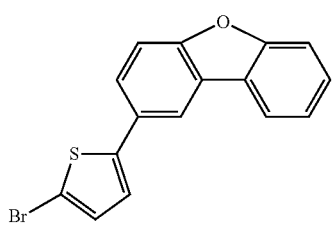

169
Intermediate63
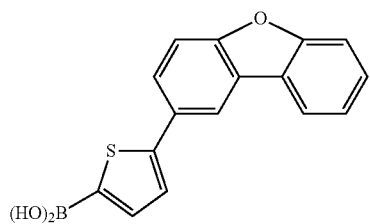
170
Intermediate64
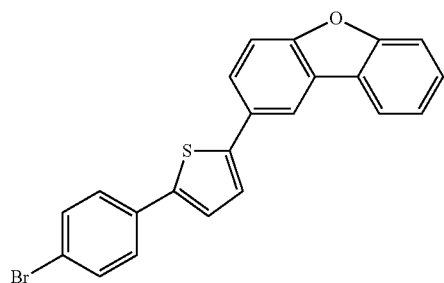
Intermediate65
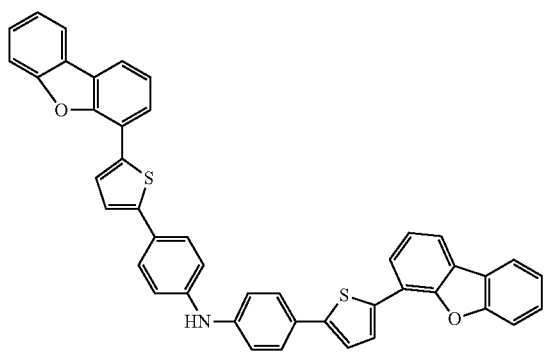
Intermediate66
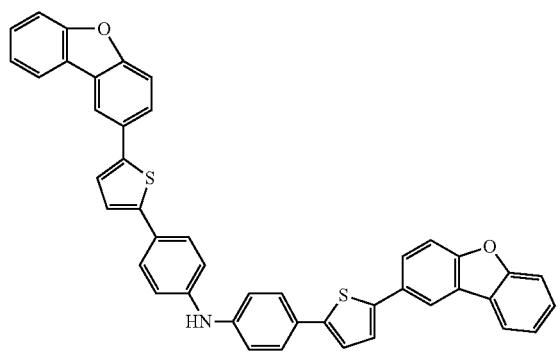
[Chem. 20]
H1
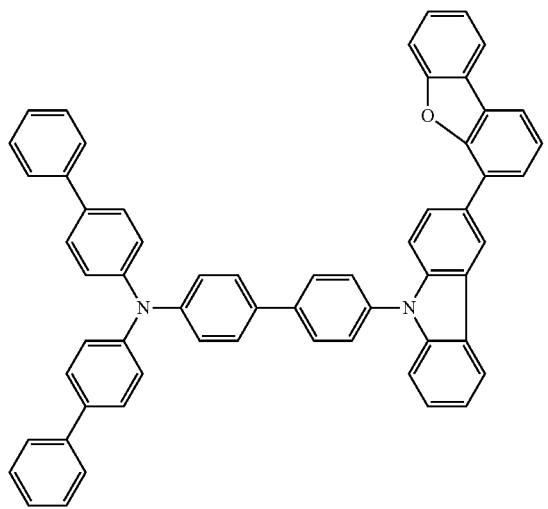
H2
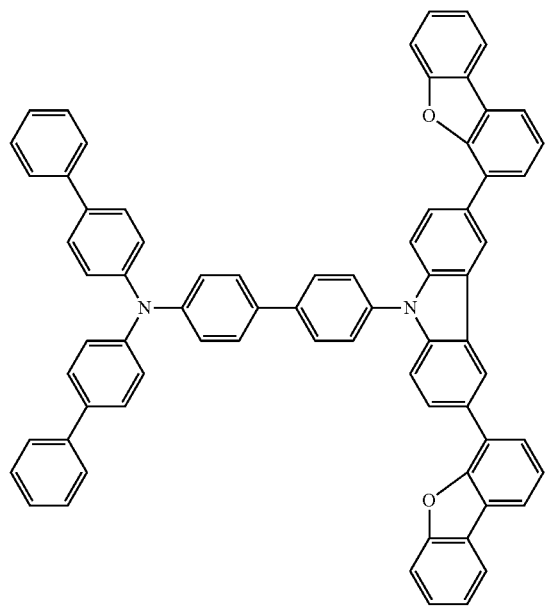

-continued
H3
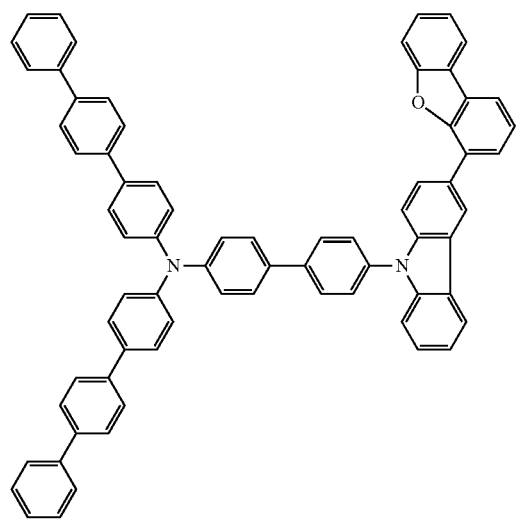
H4
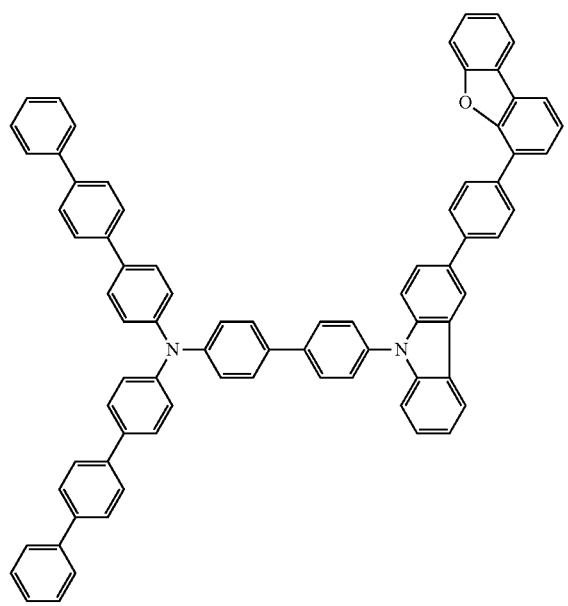
H5
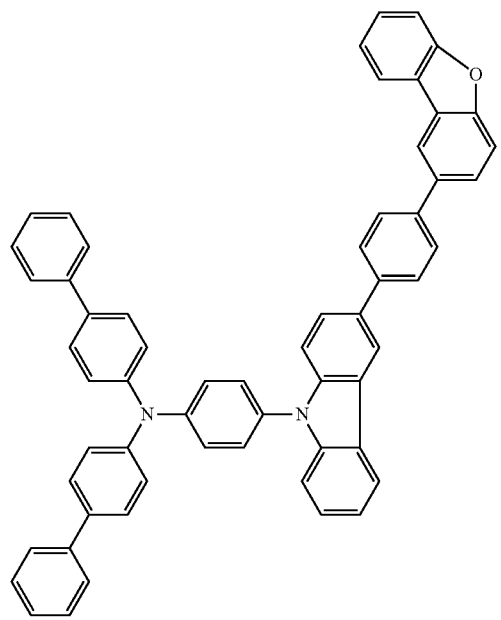
H6
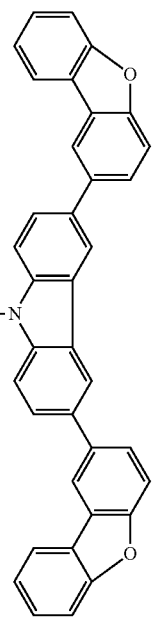

-continued
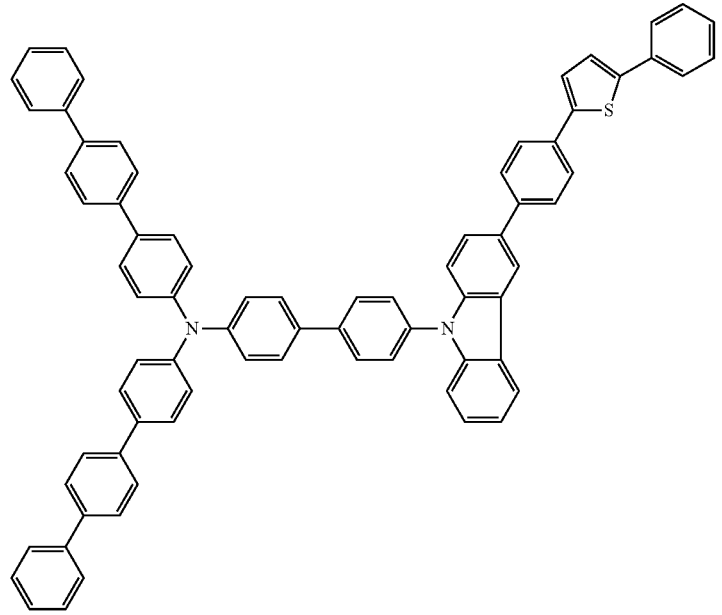
H7
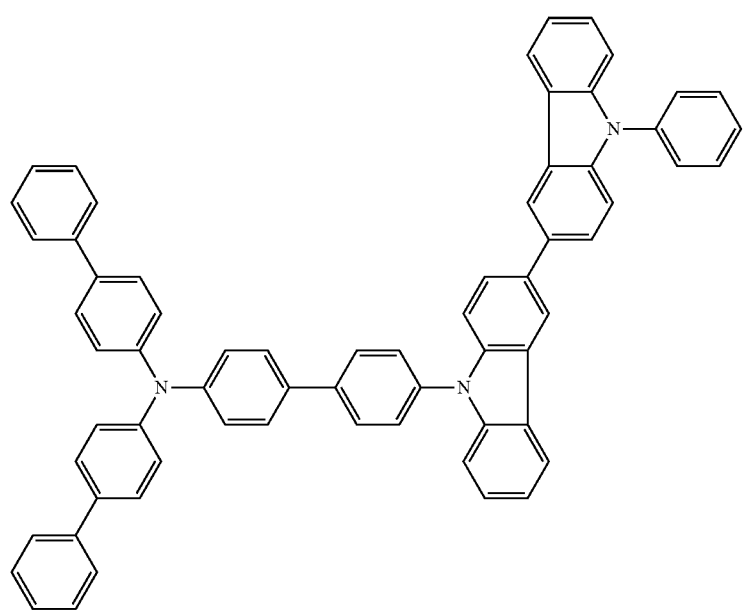
H8

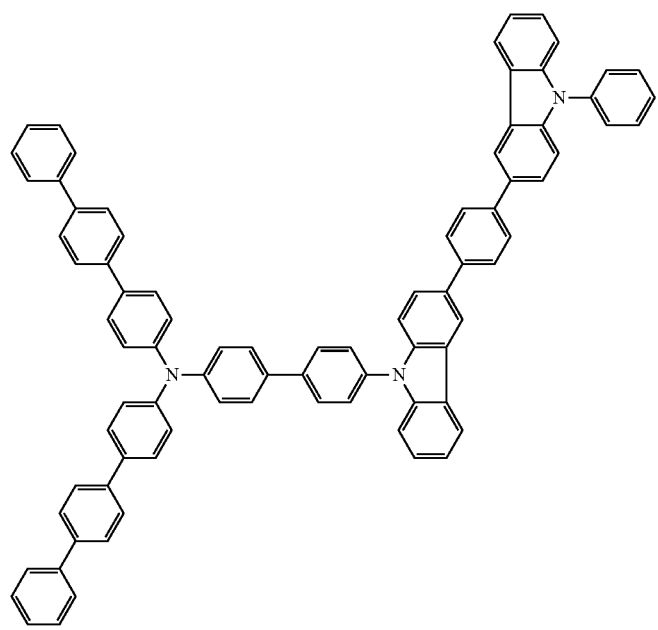
H9
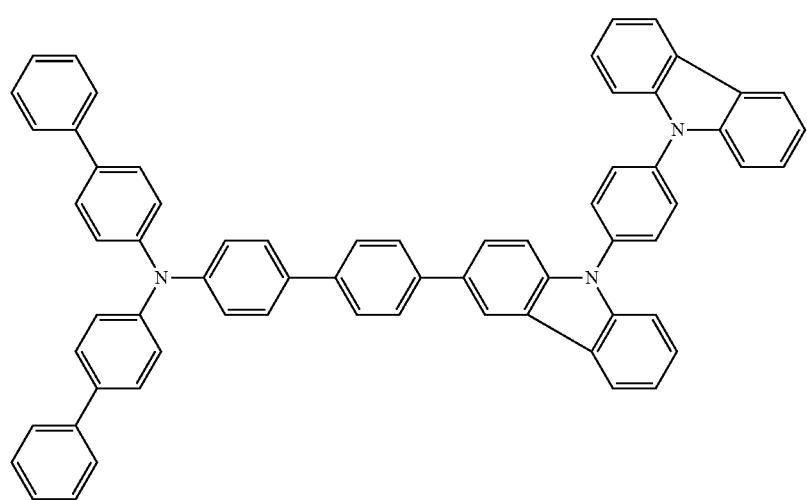
H10

H11
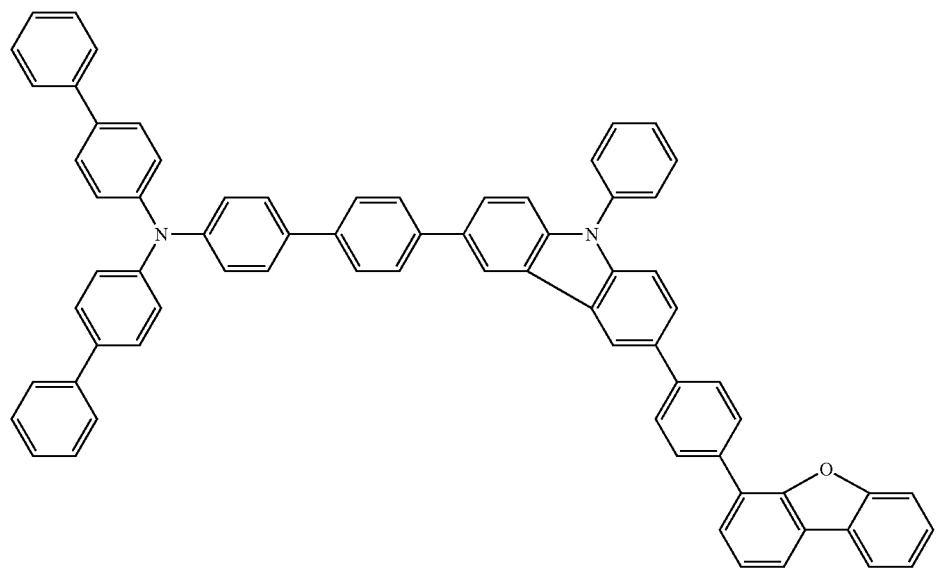
H12
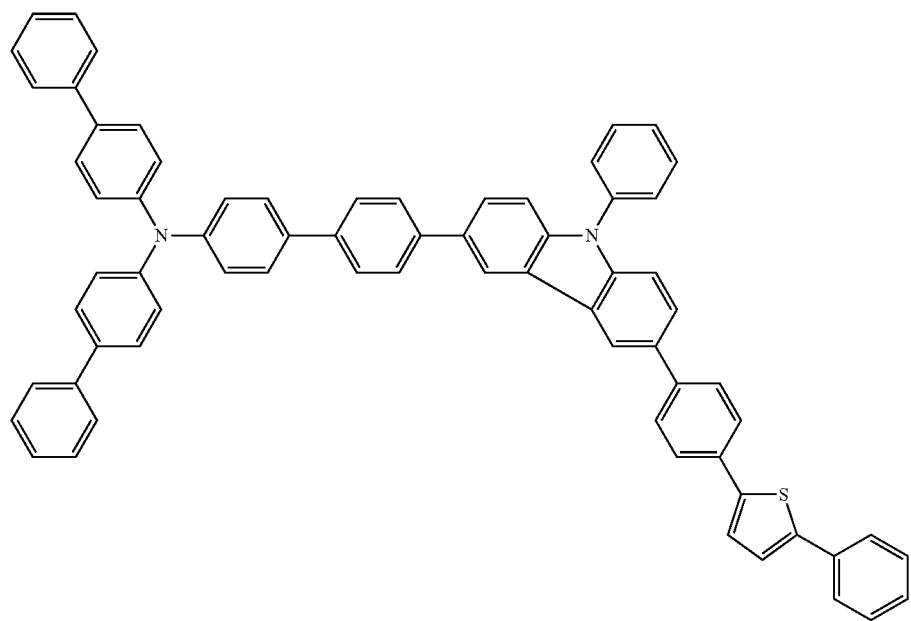

-continued
H13
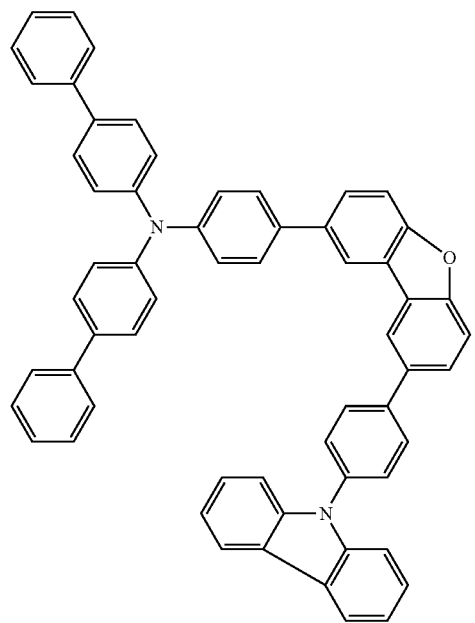
H14
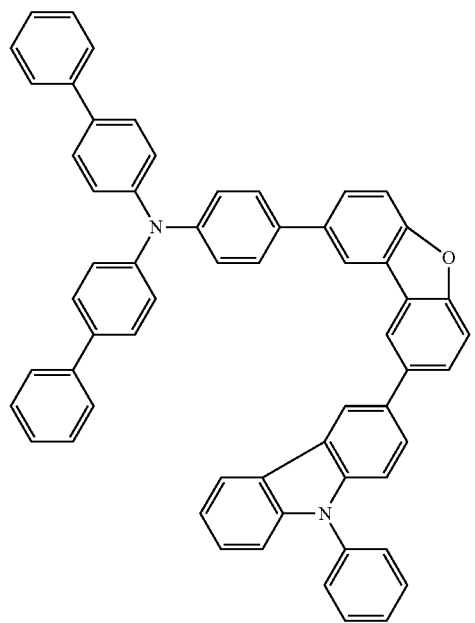
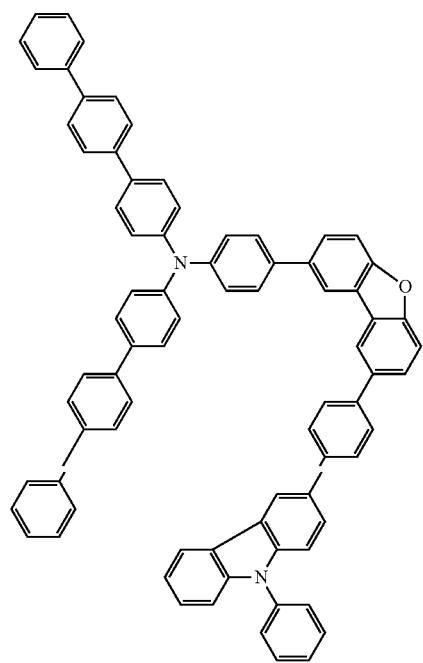
H16
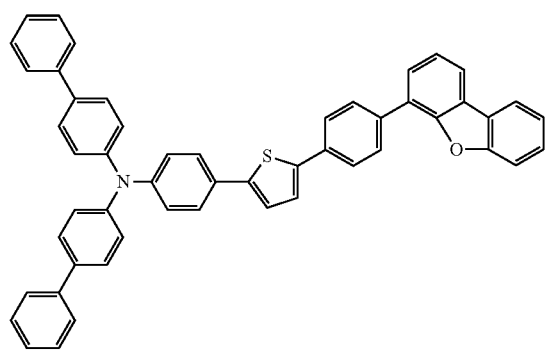

-continued
[Chem. 21]
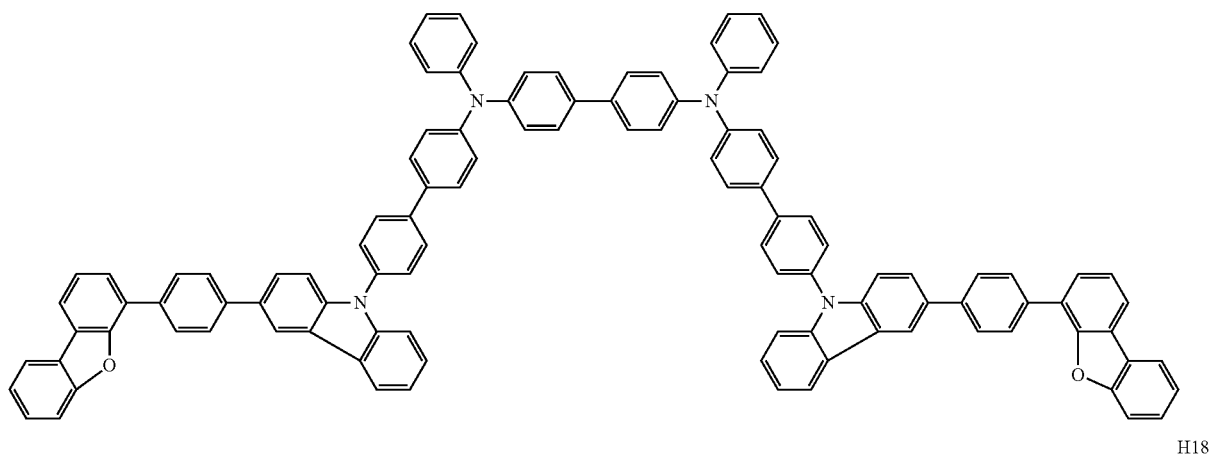
H17
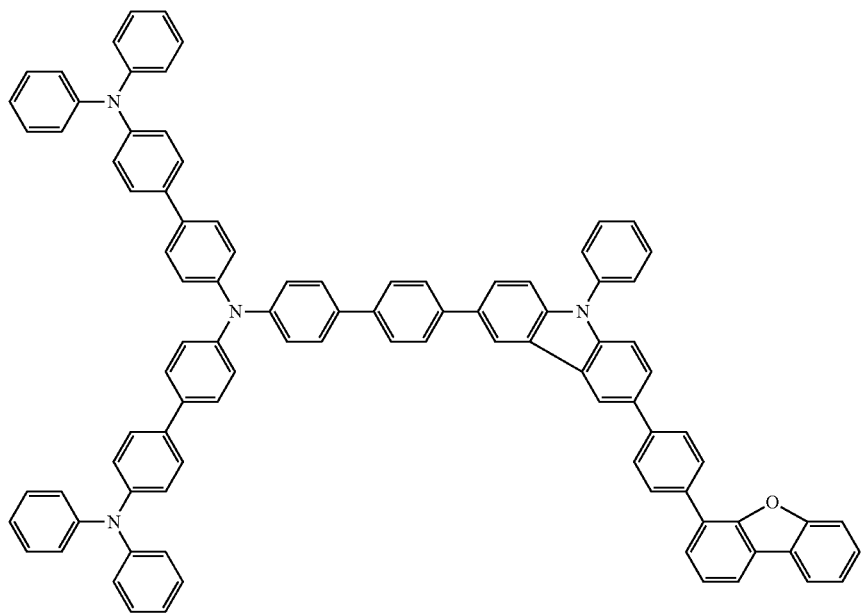
H18
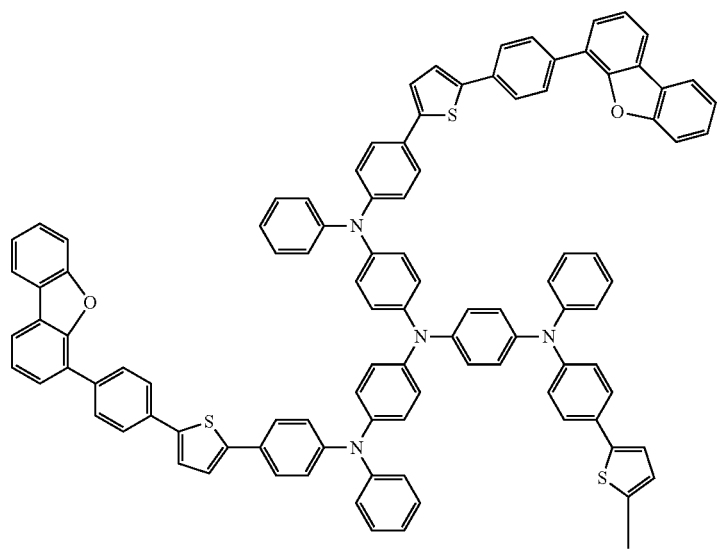
H19

183
-continued
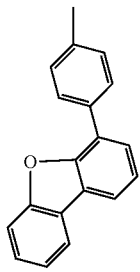
184
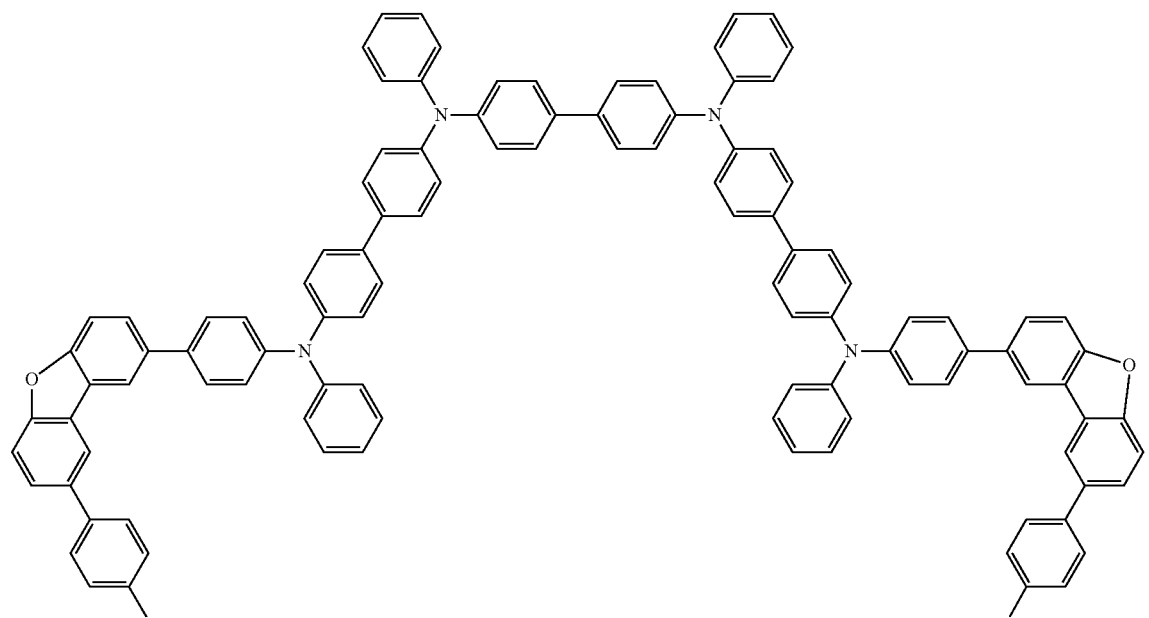
H20
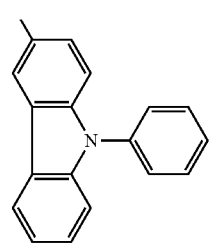

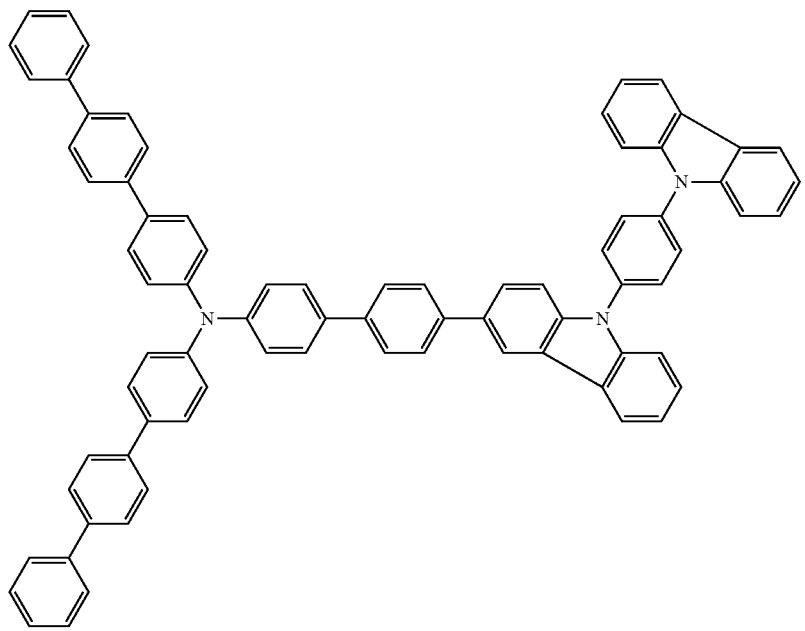
H21
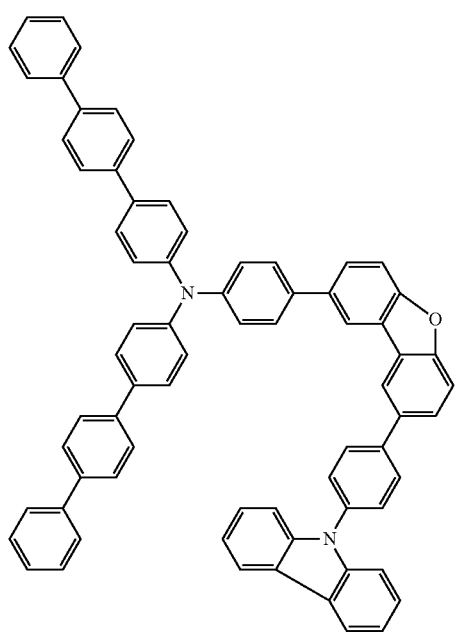
H22

[Chem. 22]
H23
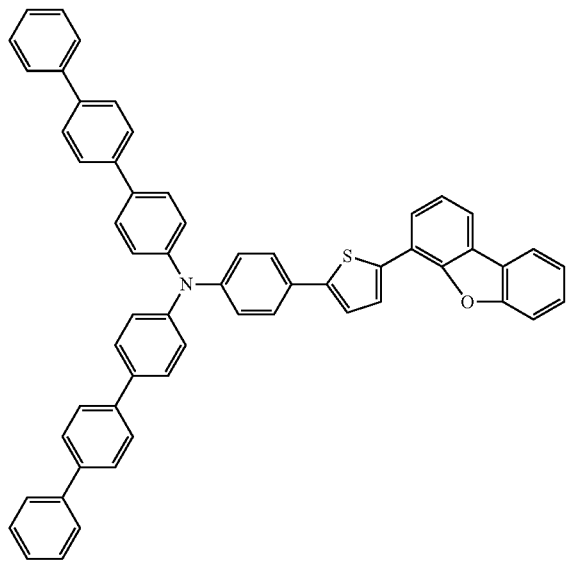
H24
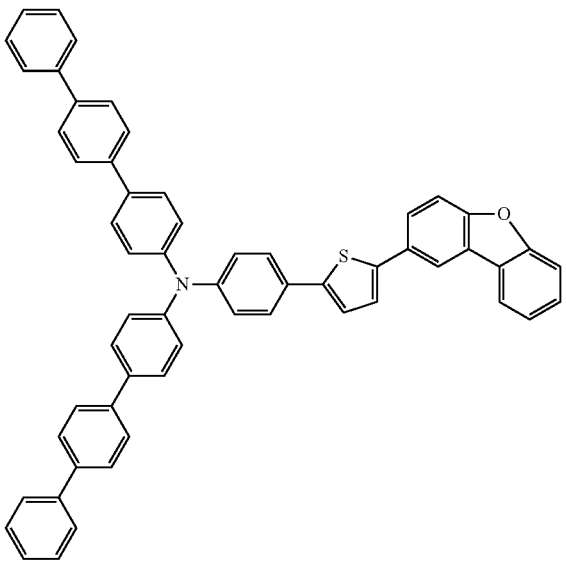
H25
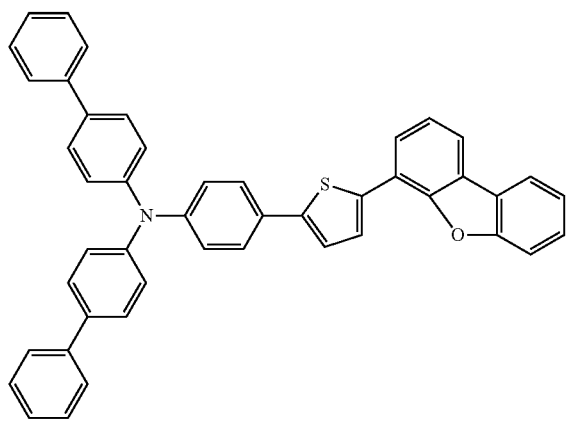
H26
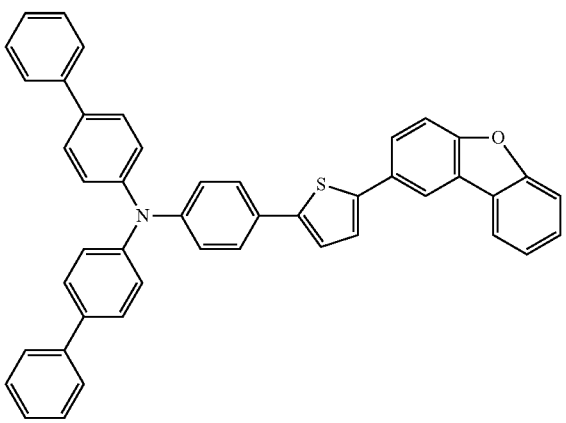
H27
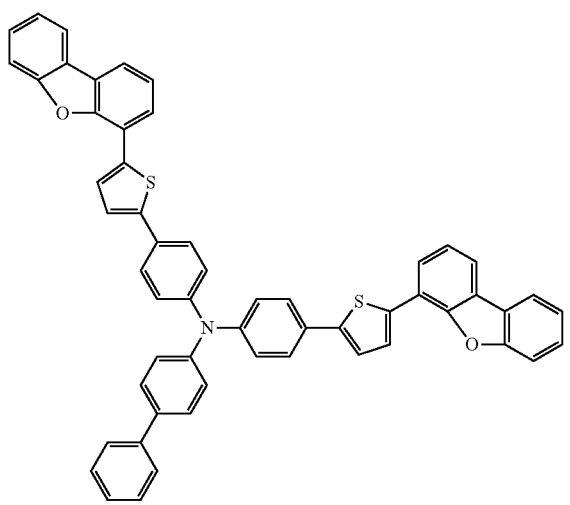
H28
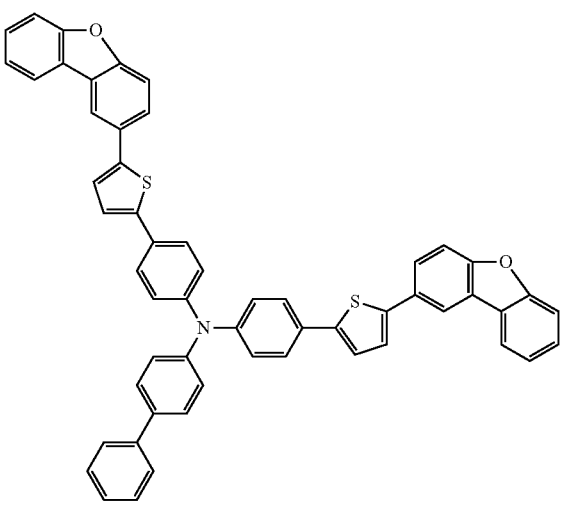

-continued
[Chem. 23]
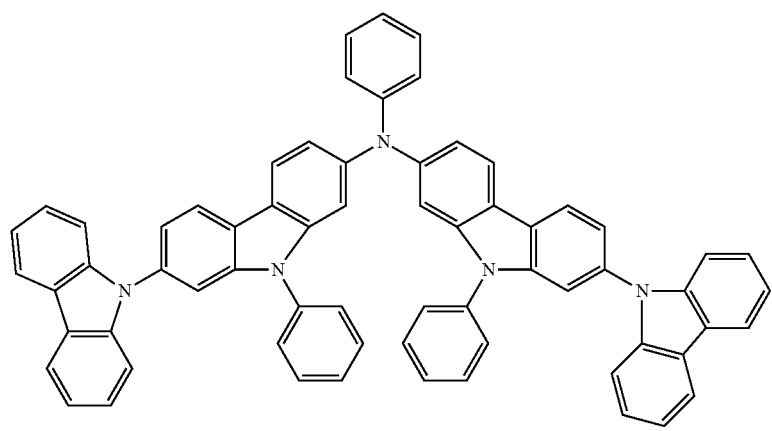
Comparative Compound 1
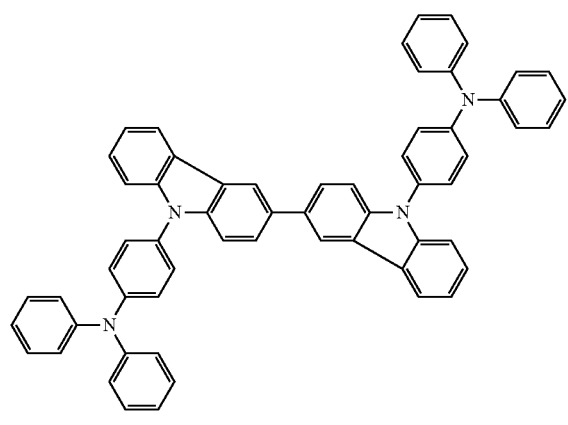
Comparative Compound 2
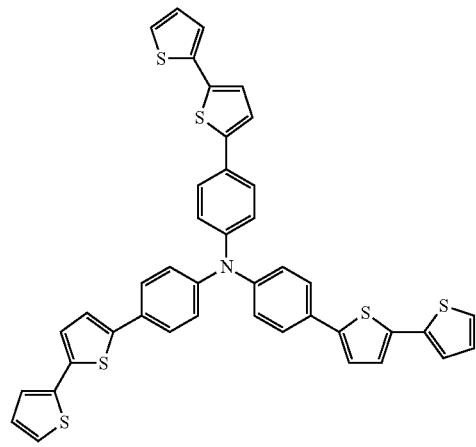
Comparative Compound 3
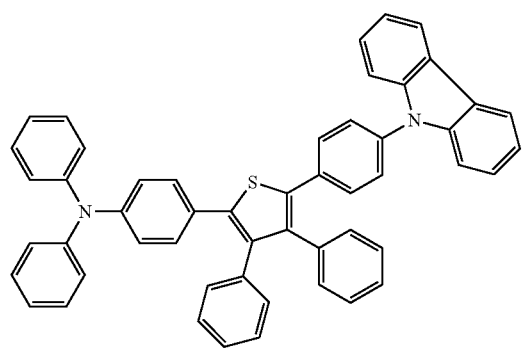
Comparative Compound 4
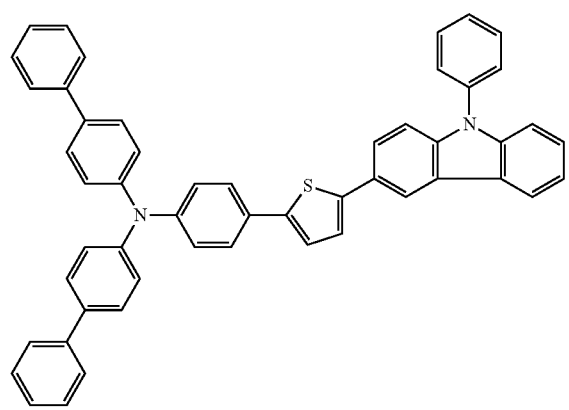
Comparative Compound 5

Comparative Compound 6

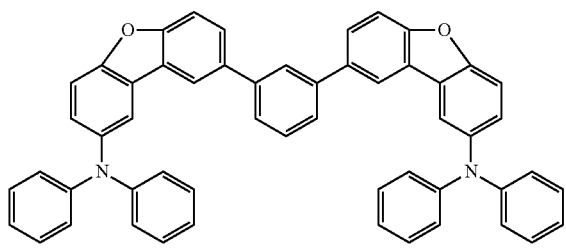

Comparative Compound 7

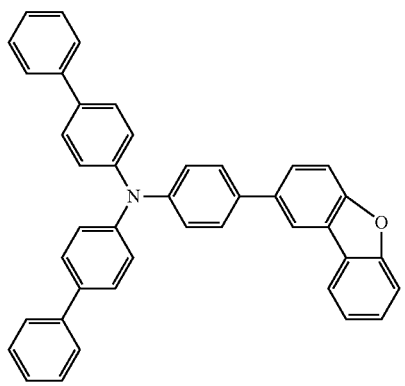

Example 1

Fabrication of Organic EL Device

A glass substrate with an ITO transparent electrode measuring 25 mm wide by 75 mm long by 1.1 mm thick (manufactured by GEOMATEC Co., Ltd.) was subjected to ultrasonic cleaning in isopropyl alcohol for 5 minutes. After that, the substrate was subjected to UV ozone cleaning for 30 minutes.

The glass substrate with the transparent electrode line after the cleaning was mounted on a substrate holder of a vacuum vapor deposition device. First, the following compound H232 was deposited from vapor on the surface on the side where the transparent electrode line was formed so as to cover the transparent electrode. Then, the H232 film having a thickness of 60 nm was formed as the hole injecting layer. Compound H4 described above was deposited from vapor and formed into a hole transporting layer having a thickness of 20 nm on the H232 film. Further, the following compound EM1 was deposited from vapor and formed into a light emitting layer having a thickness of 40 nm. Simultaneously with this formation, the following amine compound D1 having a styryl group, as a light emitting molecule, was deposited from vapor in such a manner that a weight ratio between the compound EM1 and the amine compound D1 was 40:2.

The following Alq was formed into a film having a thickness of 10 nm on the resultant film. The film functions as an electron injecting layer. After that, Li serving as a reduction-causing dopant (Li source: manufactured by SAES Getters) and Alq were subjected to co-vapor deposition. Thus, an Alq:Li film (having a thickness of 10 nm) was formed as an electron injecting layer (cathode). Metal Al was deposited from vapor onto the Alq:Li film to form a metal cathode. Thus, an organic EL device was formed.

Next, after the resultant organic EL device had been stored at 105° C. for 8 hours, the luminescent color of the device was observed. A luminous efficiency at 10 mA/cm$^2$ was calculated by measuring a luminance by using a CS1000 manufactured by Minolta. Further, the half lifetime of emitted light in DC constant current driving at an initial luminance of 5,000 cd/m$^2$ and room temperature was measured. Table 1 shows the results.

[Chem. 24]

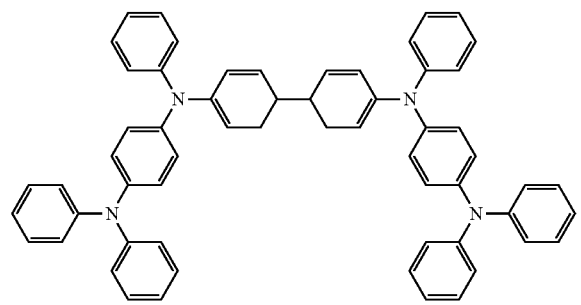

H232

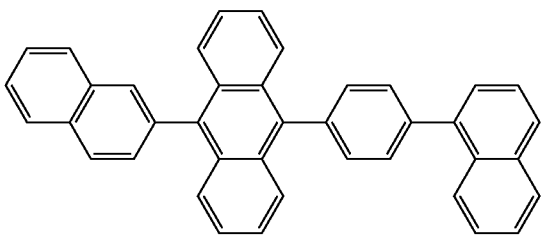

EM1

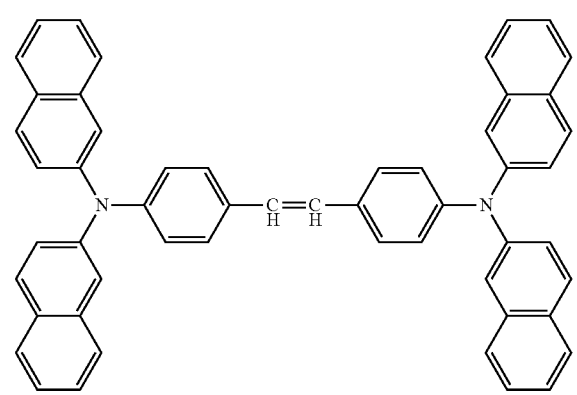

D1

-continued

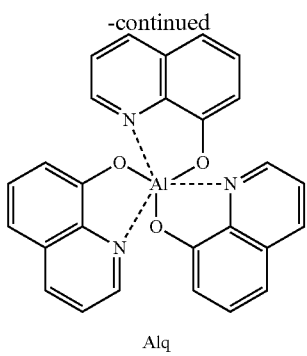

Alq

Examples 2 to 7

Fabrication of Organic EL Device

Each organic EL device was fabricated in the same manner as in Example 1 except that the respective compounds shown in Table 1 were used as hole transporting materials instead of Compound H4.

Further, for the resultant organic EL device, the half lifetime of emitted light in DC constant current driving at an initial luminance of 5,000 cd/m² and room temperature was measured in the same manner as in Example 1. Table 1 shows the results.

Comparative Examples 1 to 7

Each organic EL device was fabricated in the same manner as in Example 1 except that respective Comparative Compounds 1 to 7 were used as hole transporting materials instead of Compound H4.

Further, for the resultant organic EL device, the luminescent color of the device was observed, and the half lifetime of emitted light in DC constant current driving at an initial luminance of 5,000 cd/m² and room temperature was measured in the same manner as in Example 1. Table 1 shows the results.

Example 8

Fabrication of Organic EL Device

An organic EL device was fabricated in the same manner as in Example 1 except that the following arylamine compound D2 was used instead of the amine compound D1 having a styryl group. Me represents a methyl group.

Further, for the resultant organic EL device, the luminescent color of the device was observed, and the half lifetime of emitted light in DC constant current driving at an initial luminance of 5,000 cd/m² and room temperature was measured in the same manner as in Example 1. Table 1 shows the results.

[Chem. 25]

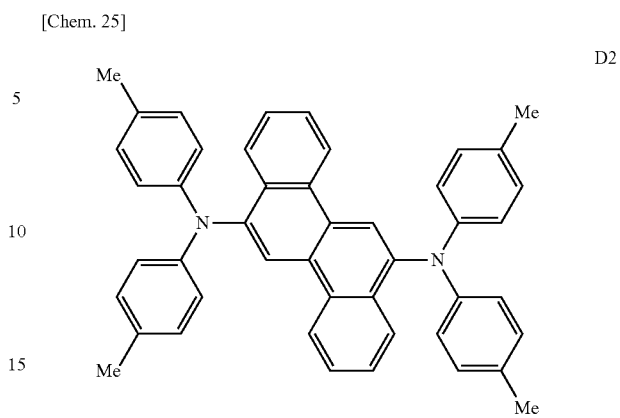

D2

Comparative Example 8

An organic EL device was fabricated in the same manner as in Example 8 except that Comparative Compound 1 described in the foregoing was used as a hole transporting material instead of Compound H4.

Further, for the resultant organic EL device, the luminescent color of the device was observed, and the half lifetime of emitted light in DC constant current driving at an initial luminance of 5,000 cd/m² and room temperature was measured in the same manner as in Example 1. Table 1 shows the results.

Example 9

Fabrication of Organic EL Device

An organic EL device was fabricated in the same manner as in Example 1 except that the following imidazole compound (ET1) was used as a hole transporting material instead of Alq.

Further, for the resultant organic EL device, the luminescent color of the device was observed, and the half lifetime of emitted light in DC constant current driving at an initial luminance of 5,000 cd/m² and room temperature was measured in the same manner as in Example 1. Table 1 shows the results.

[Chem. 26]

Imidazole Compound (ET1)

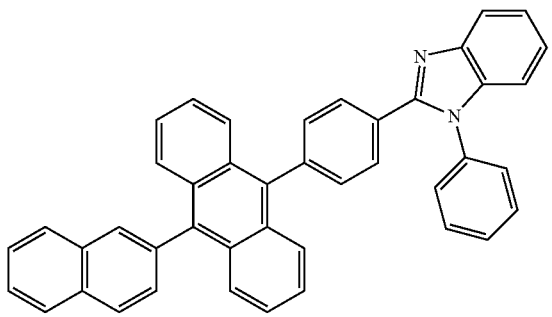

Comparative Example 9

An organic EL device was fabricated in the same manner as in Example 9 except that Comparative Compound 1 described in the foregoing was used as a hole transporting material instead of Compound H4.

Further, for the resultant organic EL device, the luminescent color of the device was observed, and the half lifetime of emitted light in DC constant current driving at an initial luminance of 5,000 cd/m² and room temperature was measured in the same manner as in Example 1. Table 1 shows the results.

Example 10

Fabrication of Organic EL Device

An organic EL device was fabricated in the same manner as in Example 1 except the following. The following acceptor compound (C-1) was formed into a film having a thickness of 10 nm instead of the compound H232, and then Compound 4 was formed into a film having a thickness of 70 nm.

Further, for the resultant organic EL device, the luminescent color of the device was observed, and the half lifetime of emitted light in DC constant current driving at an initial luminance of 5,000 cd/m² and room temperature was measured in the same manner as in Example 1. Table 1 shows the results.

[Chem. 27]

Acceptor Compound (C-1)

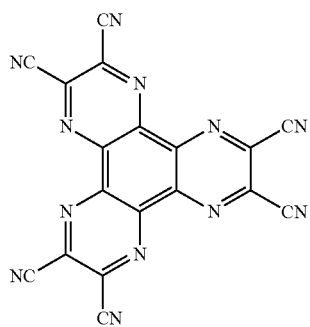

Comparative Example 10

An organic EL device was fabricated in the same manner as in Example 10 except that Comparative Compound 1 described in the foregoing was used as a hole transporting material instead of Compound H4.

Further, for the resultant organic EL device, the luminescent color of the device was observed, and the half lifetime of emitted light in DC constant current driving at an initial luminance of 5,000 cd/m² and room temperature was measured in the same manner as in Example 1. Table 1 shows the results.

Example 11

Fabrication of Organic EL Device

An organic EL device was fabricated in the same manner as in Example 1 except that: Compound H11 was used as a hole injecting material instead of the compound H232; and two layers of hole transporting materials were laminated.

Further, for the resultant organic EL device, the luminescent color of the device was observed, and the half lifetime of emitted light in DC constant current driving at an initial luminance of 5,000 cd/m² and room temperature was measured in the same manner as in Example 1. Table 1 shows the results.

Example 12

Fabrication of Organic EL Device

An organic EL device was fabricated in the same manner as in Example 11 except that Compound H16 was used as a hole transporting material instead of Compound H11.

Further, for the resultant organic EL device, the luminescent color of the device was observed, and the half lifetime of emitted light in DC constant current driving at an initial luminance of 5,000 cd/m² and room temperature was measured in the same manner as in Example 1. Table 1 shows the results.

Comparative Example 11

An organic EL device was fabricated in the same manner as in Example 11 except that Comparative Compound 1 described in the foregoing was used instead of Compound H11.

Further, for the resultant organic EL device, the luminescent color of the device was observed, and the half lifetime of emitted light in DC constant current driving at an initial luminance of 5,000 cd/m² and room temperature was measured in the same manner as in Example 1. Table 1 shows the results.

Examples 13 to 18

Fabrication of Organic EL Device

Each organic EL device was fabricated in the same manner as in Example 1 except that the respective compounds shown in Table 1 were used as hole transporting materials instead of Compound H4.

Further, for the resultant organic EL device, the half lifetime of emitted light in DC constant current driving at an initial luminance of 5,000 cd/m² and room temperature was measured in the same manner as in Example 1. Table 1 shows the results.

TABLE 1

| Example | Hole transporting material | Luminescent color | Half lifetime (hour(s)) |
|---|---|---|---|
| 1 | H4 | Blue | 370 |
| 2 | H9 | Blue | 310 |
| 3 | H11 | Blue | 340 |
| 4 | H13 | Blue | 280 |
| 5 | H15 | Blue | 310 |
| 6 | H21 | Blue | 340 |
| 7 | H22 | Blue | 360 |
| 8 | H4 | Blue | 360 |
| 9 | H4 | Blue | 310 |
| 10 | H4 | Blue | 250 |
| 11 | H11/H4 | Blue | 410 |
| 12 | H16/H4 | Blue | 420 |
| 13 | H23 | Blue | 340 |
| 14 | H24 | Blue | 310 |
| 15 | H25 | Blue | 300 |
| 16 | H26 | Blue | 280 |
| 17 | H27 | Blue | 330 |
| 18 | H28 | Blue | 300 |

TABLE 1-continued

| Example | Hole transporting material | Luminescent color | Half lifetime (hour(s)) |
|---|---|---|---|
| Comparative Example 1 | Comparative Compound 1 | Blue | 170 |
| 2 | 2 | Blue | 120 |
| 3 | 3 | Blue | 40 |
| 4 | 4 | Blue | 80 |
| 5 | 5 | Blue | 90 |
| 6 | 6 | Blue | 140 |
| 7 | 7 | Blue | 120 |
| 8 | Comparative Compound 1 | Blue | 130 |
| 9 | Comparative Compound 1 | Blue | 160 |
| 10 | Comparative Compound 1 | Blue | 110 |
| 11 | Comparative Compound 5/H4 | Blue | 150 |

As is apparent from the results of Table 1, an organic EL device using the aromatic amine derivative of the present invention provides high luminous efficiency even at high temperatures and has a long half lifetime as compared with an organic EL device using an aromatic amine derivative for comparison.

INDUSTRIAL APPLICABILITY

As described above in detail, the molecules of the aromatic amine derivative of the present invention hardly crystallize, and the incorporation of the derivative into an organic thin film layer improves a yield upon fabrication of an organic EL device and can realize an organic EL device having a long lifetime. Accordingly, the derivative is extremely useful as a material for an organic EL device having high practicality.

The invention claimed is:

1. An aromatic amine derivative represented by any one of formulae (13) to (17):

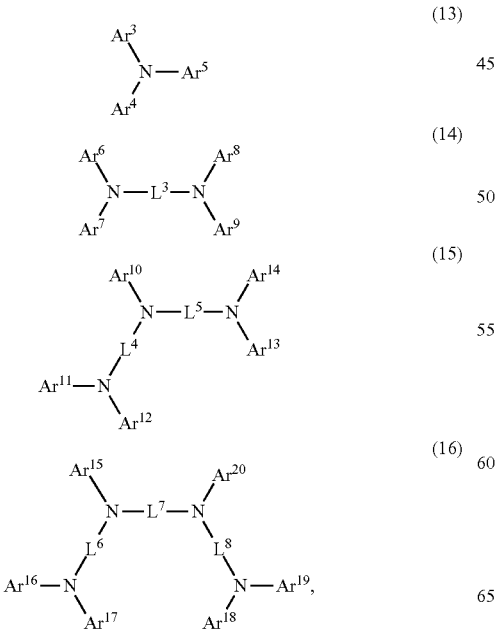

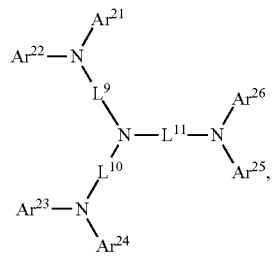

wherein $Ar^3$ to $Ar^{26}$ are substituted or unsubstituted aryl groups having 6 to 50 ring carbon atoms except that at least one of $Ar^3$ to $Ar^5$, at least one of $Ar^6$ to $Ar^9$, at least one of $Ar^{10}$ to $Ar^{14}$, at least one of $Ar^{15}$ to $Ar^{20}$, and at least one of $Ar^{21}$ to $Ar^{26}$ are each represented by formula (1) below, and $L^3$ to $L^{11}$ each represent the same linking group as the linking group represented by $L^2$ in formula (1) below:

wherein
(i) $L^1$ represents a substituted or unsubstituted arylene group having 6 to 50 ring carbon atoms,
(ii) $L^2$ represents a single bond, or a substituted or unsubstituted arylene group having 6 to 50 ring carbon atoms,
provided that an arbitrary substituent for each of $L^1$ and $L^2$ comprises a linear or branched alkyl group having 1 to 10 carbon atoms, a cycloalkyl group having 3 to 10 ring carbon atoms, a trialkylsilyl group having 3 to 30 carbon atoms, a triarylsilyl group whose aryl groups each have 6 to 10 ring carbon atoms, an alkylarylsilyl group having 8 to 24 carbon atoms whose aryl portion has 6 to 14 ring carbon atoms, an unsubstituted aryl group having 6 to 30 ring carbon atoms, a halogen atom, or a cyano group, and a plurality of substituents are identical to or different from each other,
(iii) A represents a linking group represented by any one of formulae (2) to (4):

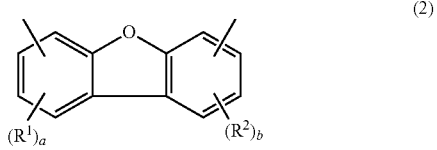

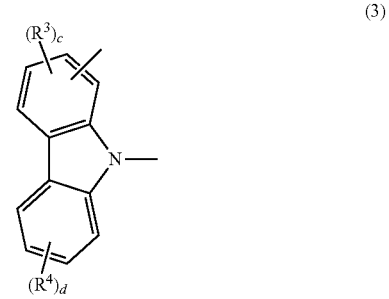

-continued (4)

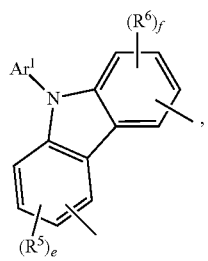

wherein
$R^1$ to $R^6$ each independently represent the same substituent as the arbitrary substituent for each of $L^1$ and $L^2$, or a formula -$L^2$-B, wherein B has the same meaning as meaning of B to be described below, and a plurality of $R^1$'s, $R^2$'s, $R^3$'s, $R^4$'s, $R^5$'s or $R^6$'s adjacent to each other are optionally bonded to each other to form a saturated or unsaturated ring, d represents an integer of 0 to 4, a, b, c, e, and f each independently represent an integer of 0 to 3, and $Ar^1$ represents a substituted or unsubstituted aryl group having 6 to 14 ring carbon atoms, provided that substituents for $Ar^1$ each independently comprise the same substituent as the arbitrary substituent for each of $L^1$ and $L^2$, and (iv) B represents a substituent represented by any one of formulae (6) and (8):

(6)

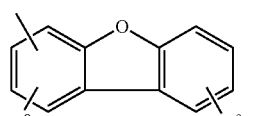

(8)

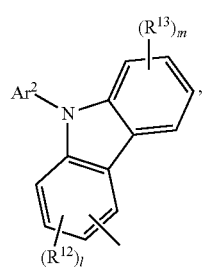

wherein
$R^8$, $R^9$, $R^{12}$ and $R^{13}$ each independently represent the same substituent as the arbitrary substituent for each of $L^1$ and $L^2$, or a formula -$L^2$-B, and a plurality of $R^8$'s, $R^9$'s, $R^{12}$'s or $R^{13}$'s adjacent to each other are optionally bonded to each other to form a saturated or unsaturated ring, i, j, k, and m each independently represent an integer of 0 to 4, h, l, and n each independently represent an integer of 0 to 3, and $Ar^2$ represents a substituted or unsubstituted aryl group having 6 to 14 ring carbon atoms, provided that substituents for $Ar^2$ each independently comprise any one of the same substituent as the arbitrary substituent for each of $L^1$ and $L^2$ except an aryl group, and a phenyl group, a biphenyl group, a naphthyl group, and a phenanthryl group.

2. The derivative of claim 1, wherein A represents a linking group represented by any one of formulae (2) to (4), and B represents a substituent represented by any one of formulae (6) and (8).

3. The derivative of claim 1, wherein $L^1$ represents a linking group represented by any one of formulae (10) to (12):

(10)

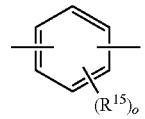

(11)

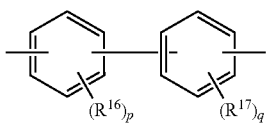

(12)

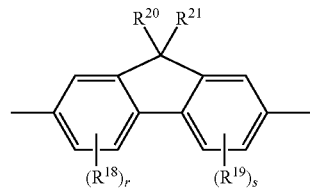

wherein
$R^{15}$ to $R^{19}$ each independently represent the same substituent as the arbitrary substituent for each of $L^1$ and $L^2$, $R^{20}$ and $R^{21}$ each independently represent a linear or branched alkyl group formed of a hydrocarbon having 1 to 10 carbon atoms, or a cycloalkyl group having 3 to 10 ring carbon atoms, a plurality of $R^{15}$'s, $R^{16}$'s, $R^{17}$'s, $R^{18}$'s, or $R^{19}$'s adjacent to each other are optionally bonded to each other to form a saturated or unsaturated ring;

o, p, and q each independently represent an integer of 0 to 4, and r and s each independently represent an integer of 0 to 3, and $L^2$ represents a single bond, or a linking group represented by any one of formulae (10) to (12).

4. The derivative of claim 3, wherein
$L^1$ represents a linking group represented by any one of formulae (10) to (12), and $L^2$ represents a single bond.

5. The derivative of claim 1, wherein
$L^1$ is at least one selected from the group consisting of a phenylene group, a biphenylene group, and a 9,9-dimethylfluorenylene group, and
$L^2$ represents a single bond.

6. The derivative of claim 1, wherein A represents a linking group of formula (2).

7. The derivative of claim 1, wherein A represents a linking group of formula (3).

8. The derivative of claim 1, wherein A represents a linking group of formula (4).

9. The derivative of claim 1, wherein B represents a substituent of formula (6).

10. The derivative of claim 1, wherein B represents a substituent of formula (8).

11. The derivative of claim 1, wherein the aromatic amine derivative is of formula (13).

12. The derivative of claim 11, wherein at least one selected from the group consisting of $Ar^3$, $Ar^4$, and $Ar^5$ is of formula (1), and the others each represent a substituted or unsubstituted aryl group having 6 to 50 ring carbon atoms.

13. The derivative of claim 1, wherein the substituted or unsubstituted aryl group having 6 to 50 ring carbon atoms comprises at least one selected from the group consisting of a naphthyl group, a biphenyl group, and a terphenyl group.

14. A material, comprising the derivative of claim 1, wherein the material is suitable for an organic electroluminescence device.

15. A hole transporting material, comprising the derivative of claim 1, which is suitable for an organic electroluminescence device.

16. An organic electroluminescence device, comprising an organic thin film layer comprising one or more layers comprising a light emitting layer,
   wherein the organic thin film layer is interposed between a cathode and an anode,
   wherein at least one layer of the organic thin film layer comprises the derivative of claim 1.

17. The device of claim 16, wherein the organic thin film layer comprises at least one member selected from the group consisting of a hole transporting layer and a hole injecting layer, and
   the derivative of claim 1 is incorporated into the at least one member.

18. The device of claim 17, wherein the organic thin film layer comprises a hole transporting zone comprising at least one selected from the group consisting of a hole transporting layer and a hole injecting layer, and
   the derivative of claim 1 is incorporated into a layer out of direct contact with the light emitting layer in the hole transporting zone.

19. The device of claim 17, wherein the derivative of claim 1 is incorporated as a main component into the at least one member.

20. The device of claim 16, wherein the light emitting layer comprises at least one selected from the group consisting of a styrylamine compound and an arylamine compound.

21. The device of claim 16, wherein a layer in contact with the anode out of layers comprised in at least one selected from the group consisting of a hole injecting layer and a hole transporting layer, comprises a layer comprising an acceptor material.

22. The device of claim 16, which emits blue light.

23. A compound of the formula H4:

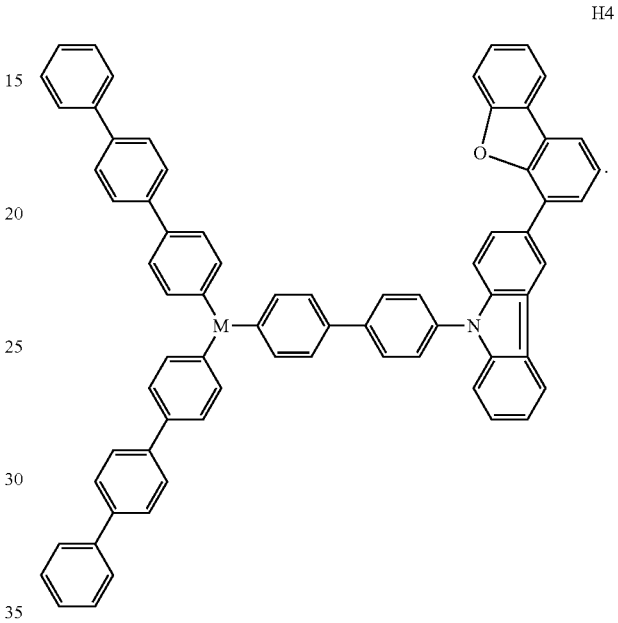

H4